US009840532B2

(12) United States Patent
Cortez et al.

(10) Patent No.: US 9,840,532 B2
(45) Date of Patent: Dec. 12, 2017

(54) 5'-SUBSTITUTED NUCLEOSIDE COMPOUNDS

(71) Applicant: Eli Lilly and Company, Indianapolis, IN (US)

(72) Inventors: Guillermo S Cortez, Indianapolis, IN (US); Zahid Quyoom Bonday, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/139,370

(22) Filed: Apr. 27, 2016

(65) Prior Publication Data

US 2016/0326208 A1 Nov. 10, 2016

(30) Foreign Application Priority Data

May 4, 2015 (EP) .................................... 15382225

(51) Int. Cl.

| | |
|---|---|
| ***A01N 43/04*** | (2006.01) |
| ***A61K 31/70*** | (2006.01) |
| ***C07H 19/14*** | (2006.01) |
| ***C07D 487/04*** | (2006.01) |
| *A61K 31/7068* | (2006.01) |
| *A61K 31/706* | (2006.01) |
| *A61K 31/7076* | (2006.01) |

(52) U.S. Cl.

CPC ........... *C07H 19/14* (2013.01); *C07D 487/04* (2013.01); *A61K 31/706* (2013.01); *A61K 31/7068* (2013.01); *A61K 31/7076* (2013.01)

(58) Field of Classification Search

None

See application file for complete search history.

(56) References Cited

FOREIGN PATENT DOCUMENTS

| | | |
|---|---|---|
| WO | 01/27114 | 4/2001 |
| WO | 2007/069923 | 6/2007 |
| WO | 2011/079236 | 6/2011 |
| WO | 2013/009735 | 1/2013 |
| WO | 2014/100695 | 6/2014 |
| WO | 2014/100716 | 6/2014 |
| WO | 2014/100719 | 6/2014 |
| WO | 2014/100730 | 6/2014 |
| WO | 2014/100734 | 6/2014 |
| WO | 2014/100764 | 6/2014 |
| WO | 2016/135582 A1 | 9/2016 |

OTHER PUBLICATIONS

Sato et al. Chemistry Letters (1978), pp. 1297-1300.*

* cited by examiner

*Primary Examiner* — Patrick T Lewis

(74) *Attorney, Agent, or Firm* — Tina M. Tucker

(57) ABSTRACT

The present invention relates to novel 5'-substituted nucleoside compounds, pharmaceutical compositions comprising the compounds, and methods of using the compounds to treat cancer, more particularly for the treatment of cancer, in particular glioblastomas, melanoma, sarcomas, gastric cancer, pancreatic cancer, cholangiocarcinoma, bladder cancer, breast cancer, non-small cell lung cancer, leukemias including acute myeloid leukemia, and lymphomas.

7 Claims, No Drawings

SEQUENCE LISTING

```
<160> NUMBER OF SEQ ID NOS: 3

<210> SEQ ID NO 1
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (26)..(26)
<223> OTHER INFORMATION: Lysine at position 26 is Biotinylated

<400> SEQUENCE: 1

His Ser Gly Arg Gly Lys Gly Gly Lys Gly Leu Gly Lys Gly Gly Ala
1               5                   10                  15

Lys Arg His Arg Lys Val Leu Arg Asp Lys
            20                  25


<210> SEQ ID NO 2
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (8)..(8)
<223> OTHER INFORMATION: Arg at position 8 is symmetric dimethyl-Arg
<220> FEATURE:
<221> NAME/KEY: MOD_RES
<222> LOCATION: (10)..(10)
<223> OTHER INFORMATION: Arg at position 10 is symmetric dimethyl-Arg
<220> FEATURE:
<221> NAME/KEY: MOD_RES
<222> LOCATION: (12)..(12)
<223> OTHER INFORMATION: Arg at position 12 is symmetric dimethyl-Arg
<220> FEATURE:
<221> NAME/KEY: MOD_RES
<222> LOCATION: (14)..(14)
<223> OTHER INFORMATION: Arg at position 14 is symmetric dimethyl-Arg
<220> FEATURE:
<221> NAME/KEY: MOD_RES
<222> LOCATION: (16)..(16)
<223> OTHER INFORMATION: Arg at position 16 is symmetric dimethyl-Arg

<400> SEQUENCE: 2

Cys Arg Glu Ala Val Ala Gly Arg Gly Arg Gly Arg Gly Arg Gly Arg
1               5                   10                  15

Gly Gly Pro Arg Arg
            20


<210> SEQ ID NO 3
<211> LENGTH: 21
```

-continued

```
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: Arg at position 7 is symmetric dimethyl-Arg
<220> FEATURE:
<221> NAME/KEY: MOD_RES
<222> LOCATION: (9)..(9)
<223> OTHER INFORMATION: Arg at position 9 is symmetric dimethyl-Arg
<220> FEATURE:
<221> NAME/KEY: MOD_RES
<222> LOCATION: (11)..(11)
<223> OTHER INFORMATION: Arg at position 11 is symmetric dimethyl-Arg
<220> FEATURE:
<221> NAME/KEY: MOD_RES
<222> LOCATION: (13)..(13)
<223> OTHER INFORMATION: Arg at position 13 is symmetric dimethyl-Arg
<220> FEATURE:
<221> NAME/KEY: MOD_RES
<222> LOCATION: (15)..(15)
<223> OTHER INFORMATION: Arg at position 15 is symmetric dimethyl-Arg

<400> SEQUENCE: 3

Arg Glu Ala Val Ala Gly Arg Gly Arg Gly Arg Gly Arg Gly Arg Gly
1               5                   10                  15

Gly Pro Arg Arg Cys
            20
```

5'-SUBSTITUTED NUCLEOSIDE COMPOUNDS

The present invention relates to novel 5'-substituted nucleoside compounds that inhibit activity of protein arginine methyltransferase 5 (PRMT5), pharmaceutical compositions comprising the compounds, and methods of using the compounds to treat physiological disorders, more particularly for the treatment of cancer.

Protein arginine methyltransferases (PRMTs) area family of enzymes that can add one or two methyl groups to the guanidine nitrogen atoms of arginine residues on histones and non-histone proteins. The abundant epigenetic modifications brought about by PRMTs allow for regulation of a wide variety of cellular functions, including, for example, RNA metabolism, transcriptional regulation, signal transduction, embryonic development, and DNA damage repair, Overexpression of different PRMTs has been frequently associated with many human cancers. Recently, increasing evidence suggests that PRMT5, an important member of the PRMT family, is a potential oncoprotein and is involved in tumorigenesis. PRMT5 is overexpressed in a number of tumors, has important oncogenes and cancer survival genes as substrates, and regulates alternative splicing and RNA maturation, a novel mechanism which is central to protein expression. Additionally, it was shown that mantle cell lymphoma is exquisitely sensitive to PRMT5 inhibition.

Potential inhibitors of PRMT5 are already known in the literature. See for example, WO2011/079236, WO2014/100764, WO2014/100716, WO2014/100695, WO2014/100730, WO2014/100734, and WO2014/100719. In addition, certain 5'-substituted nucleosides are known in the literature. See for example, WO2001/27114 and WO2013/009735.

There is a need for new cancer treatments. In particular there is a need for new cancer treatments for glioblastomas, gastric cancer, pancreatic cancer, bladder cancer, lung cancers, leukemias, and lymphomas. There remains a need to provide alternative PRMT5 inhibitors useful in the treatment of cancer. Preferably such compounds have properties that enable optimal dosing required for maximal inhibition of tumor cell growth while having acceptable tolerability for the patient. Preferably such compounds would also be orally bioavailable.

The present invention provides certain novel 5'-substituted nucleoside compounds that are inhibitors of PRMT5 and may have clinical utility as a single agent or in combination with other anti-cancer agents for treatment of different types of cancers and in particular glioblastomas, melanoma, sarcomas, gastric cancer, pancreatic cancer, cholangiocarcinoma, bladder cancer, breast cancer, non-small cell lung cancer, leukemias including acute myeloid leukemia, and lymphomas.

The present invention provides a compound of the formula:

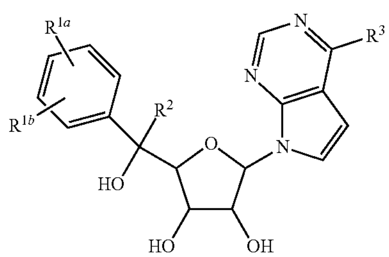

wherein:

$R^{1a}$ is hydrogen, $C_1$-$C_2$ alkyl, trifluoromethyl, cyano, chloro or fluoro;

$R^{1b}$ is hydrogen, chloro or fluoro;

$R^2$ is hydrogen or $C_1$-$C_3$ alkyl; and $R^3$ is hydrogen, methyl or amino;

or a pharmaceutically acceptable salt thereof.

The present invention provides a compound of the formula:

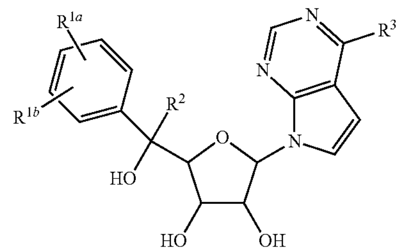

wherein:

$R^{1a}$ is hydrogen, $C_1$-$C_2$ alkyl, $C_3$-$C_6$ cycloalkoxy, trifluoromethyl, cyano, chloro or fluoro;

$R^{1b}$ is hydrogen, chloro or fluoro;

$R^2$ is hydrogen or $C_1$-$C_3$ alkyl; and $R^3$ is hydrogen, methyl or amino;

or a pharmaceutically acceptable salt thereof.

The present invention further provides a compound of the formula:

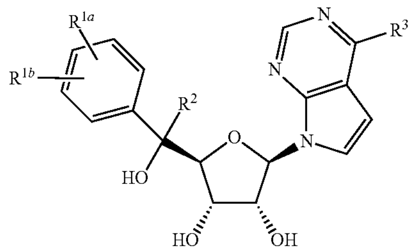

wherein:

$R^{1a}$ is hydrogen, $C_1$-$C_2$ alkyl, trifluoromethyl, cyano, chloro or fluoro;

$R^{1b}$ is hydrogen, chloro or fluoro;

$R^2$ is hydrogen or $C_1$-$C_3$ alkyl; and $R^3$ is hydrogen, methyl or amino;

or a pharmaceutically acceptable salt thereof.

The present invention further provides a compound of the formula:

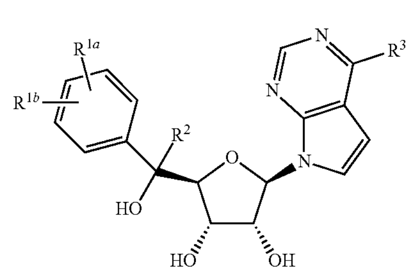

wherein:

$R^{1a}$ is hydrogen, $C_1$-$C_2$ alkyl, $C_3$-$C_6$ cycloalkoxy, trifluoromethyl, cyano, chloro or fluoro;

$R^{1b}$ is hydrogen, chloro or fluoro;

$R^2$ is hydrogen or $C_1$-$C_3$ alkyl; and $R^3$ is hydrogen, methyl or amino;

or a pharmaceutically acceptable salt thereof.

The present invention further provides a compound of the formula:

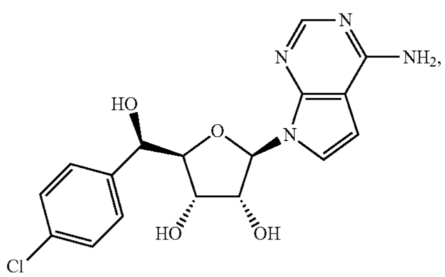 [SMILES: Nc1ncnc2c1ccn2[C@@H]1O[C@H]([C@H](O)c2ccc(Cl)cc2)[C@@H](O)[C@H]1O]

or a pharmaceutically acceptable salt thereof.

The present invention also provides a compound of the formula:

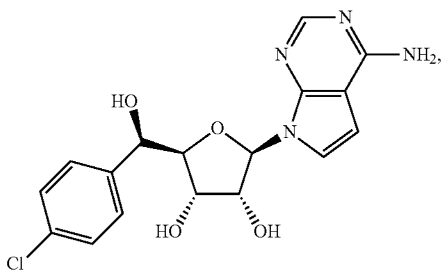 [SMILES: Nc1ncnc2c1ccn2[C@@H]1O[C@H]([C@H](O)c2ccc(Cl)cc2)[C@@H](O)[C@H]1O]

which is crystalline and characterized by an X-ray powder diffraction pattern (Cu radiation, λ=1.54060 Å) comprising a peak at 25.1° in combination with one or more of the peaks selected from the group consisting of 17.1°, 13.6°, 20.5°, 24.0°, and 14.5° (2θ+/−0.2°).

The present invention further provides a compound of the formula:

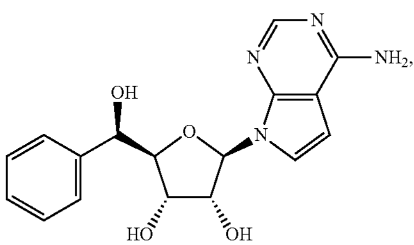 [SMILES: Nc1ncnc2c1ccn2[C@@H]1O[C@H]([C@H](O)c2ccccc2)[C@@H](O)[C@H]1O]

or a pharmaceutically acceptable salt thereof.

The present invention further provides a compound of the formula:

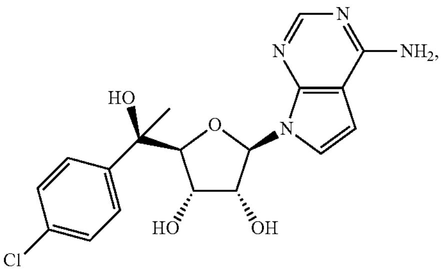 [SMILES: C[C@@](O)(c1ccc(Cl)cc1)[C@H]1O[C@@H](n2ccc3c(N)ncnc32)[C@H](O)[C@@H]1O]

or a pharmaceutically acceptable salt thereof.

The present invention further provides a compound of the formula:

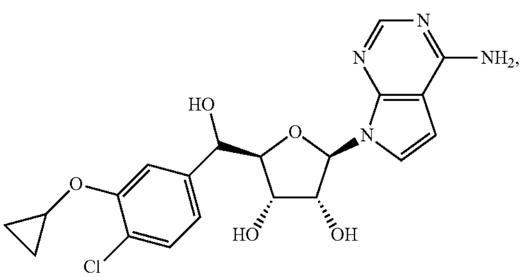 [SMILES: Nc1ncnc2c1ccn2[C@@H]1O[C@H](C(O)c2ccc(Cl)c(OC3CC3)c2)[C@@H](O)[C@H]1O]

or a pharmaceutically acceptable salt thereof.

The present invention further provides a compound of the formula:

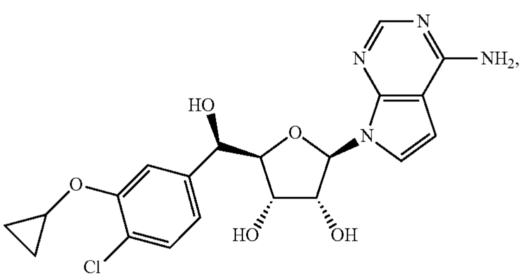 [SMILES: Nc1ncnc2c1ccn2[C@@H]1O[C@H]([C@H](O)c2ccc(Cl)c(OC3CC3)c2)[C@@H](O)[C@H]1O]

or a pharmaceutically acceptable salt thereof.

The present invention also provides a pharmaceutical composition comprising a compound of the present invention or a pharmaceutically acceptable salt thereof, with a pharmaceutically acceptable excipient, carrier, or diluent.

The present invention provides a method of treating cancer, in particular glioblastomas, melanoma, sarcomas, gastric cancer, pancreatic cancer, cholangiocarcinoma, bladder cancer, breast cancer, non-small cell lung cancer, leukemias including acute myeloid leukemia, and lymphomas in a patient in need of such treatment comprising administering the patient an effective amount of a compound of the present invention or a pharmaceutically acceptable salt thereof.

This invention also provides a compound of the present invention or a pharmaceutically acceptable salt thereof for use in therapy. Additionally, this invention provides a compound of the present invention or a pharmaceutically acceptable salt thereof for use in the treatment of cancer, in particular glioblastomas, melanoma, sarcomas, gastric cancer, pancreatic cancer, cholangiocarcinoma, bladder cancer, breast cancer, non-small cell lung cancer, leukemias including acute myeloid leukemia, and lymphomas. Furthermore, this invention provides the use of a compound of the present invention or a pharmaceutically acceptable salt thereof for the manufacture of a medicament for the treatment of cancer, in particular glioblastomas, melanoma, sarcomas, gastric cancer, pancreatic cancer, cholangiocarcinoma, bladder cancer, breast cancer, non-small cell lung cancer, leukemias, including acute myeloid leukemia, and lymphomas.

In particular, the compound is

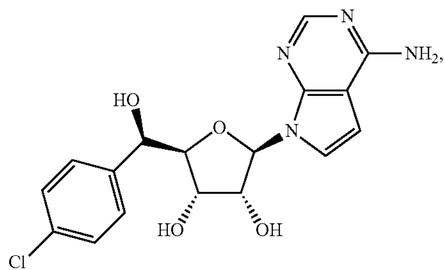 [SMILES: Nc1ncnc2c1ccn2[C@@H]1O[C@H]([C@H](O)c2ccc(Cl)cc2)[C@@H](O)[C@H]1O]

or a pharmaceutically acceptable salt thereof.

In particular the compound is

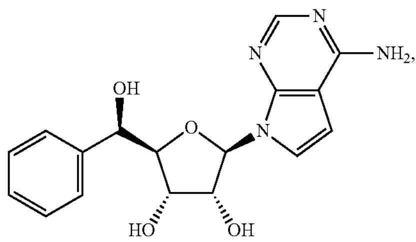 [SMILES: Nc1ncnc2c1ccn2[C@@H]1O[C@H]([C@H](O)c2ccccc2)[C@@H](O)[C@H]1O]

or a pharmaceutically acceptable salt thereof.

In particular the compound is

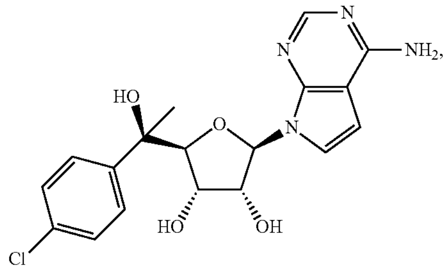 [SMILES: C[C@@](O)(c1ccc(Cl)cc1)[C@H]1O[C@@H](n2ccc3c(N)ncnc32)[C@H](O)[C@@H]1O]

or a pharmaceutically acceptable salt thereof.

In particular the compound is

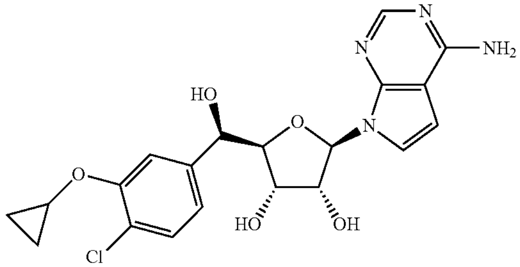 [SMILES: Nc1ncnc2c1ccn2[C@@H]1O[C@H]([C@H](O)c2ccc(Cl)c(OC3CC3)c2)[C@@H](O)[C@H]1O]

or a pharmaceutically acceptable salt thereof.

As used herein, "treat", "treating" or "treatment" refers to restraining, slowing, stopping, or reversing the progression or severity of an existing symptom or disorder.

As used herein, the term "patient" refers to a warm blooded animal such as a mammal, in particular a human, which is afflicted with a particular disease, disorder, or condition.

The following paragraphs describe preferred classes of the present invention.

a) $R^{1a}$ is hydrogen, chloro or cyclopropoxy;

b) $R^{1b}$ is hydrogen or chloro;

c) $R^2$ is hydrogen or methyl;

d) $R^3$ is amino;

e) $R^{1a}$ is chloro, $R^{1b}$ is hydrogen, and $R^2$ is hydrogen;

f) $R^{1a}$ is chloro, $R^{1b}$ is hydrogen, and $R^2$ is methyl;

g) $R^{1a}$ is hydrogen, $R^{1b}$ is hydrogen, and $R^2$ is hydrogen;

h) $R^{1a}$ is cyclopropoxy, $R^{1b}$ is chloro, and $R^2$ is hydrogen;

i) $R^{1a}$ is chloro, $R^{1b}$ is hydrogen, and $R^3$ is amino;

j) $R^{1a}$ is hydrogen, $R^{1b}$ is hydrogen, and $R^3$ is amino;

k) $R^{1a}$ is cyclopropoxy, $R^{1b}$ is chloro, and $R^3$ is amino;

l) $R^2$ is hydrogen and $R^3$ is amino;

m) $R^2$ is methyl and $R^3$ is amino;

n) $R^{1a}$ is chloro, $R^{1b}$ is hydrogen, $R^2$ is hydrogen, and $R^3$ is amino;

o) $R^{1a}$ is hydrogen, $R^{1b}$ is hydrogen, $R^2$ is hydrogen, and $R^3$ is amino;

p) $R^{1a}$ is chloro, $R^{1b}$ is hydrogen, $R^2$ is methyl, and $R^3$ is amino; and q) $R^{1a}$ is cyclopropoxy, $R^{1b}$ is chloro, $R^2$ is hydrogen, and $R^3$ is amino.

It will be understood by the skilled reader that the compounds of the present invention are capable of forming salts. The compounds of the present invention contain basic heteroatoms, specifically an amine, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts," *Journal of Pharmaceutical Sciences*, Vol 66, No. 1, January 1977.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from the schemes, to prepare compounds or salts of the present invention. The products of each step in the Schemes below can be recovered by conventional methods well known in the art, including extraction, evaporation, precipitation, chromatography, filtration, trituration, and crystallization.

Some intermediates or compounds of the present invention may have one or more chiral or stereogenic centers. The present invention contemplates all individual stereoisomers, enantiomers, and diastereomers, as well as mixtures of the enantiomers and diastereomers of said compounds including racemates. It is preferred that compounds of the present invention containing at least one chiral center exist as single enantiomers or diastereomers. The single enantiomer or diastereomer may be prepared beginning with chiral reagents (as illustrated in Scheme I below) or by stereoselective or stereospecific synthetic techniques (as illustrated in Scheme II below). Alternatively, the single enantiomer or diastereomers may be isolated from mixtures by standard chiral chromatographic or crystallization techniques.

Additionally, certain intermediates described in the following schemes may contain one or more oxygen or nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain abbreviations are defined as follows: "A375" refers to a human melanoma tumor derived cell line; "ACN" refers to acetonitrile; "ATCC" refers to American Type Culture Collection; "BID" refers to twice daily dosing; "cat. #" refers to catalogue number; "CDI" refers to 1,1'-carbonyldiimidazole; "CDKN1A" refers to cyclin-dependent kinase inhibitor 1, p21, p21$^{Cip1}$, or p21$^{Waf1}$; "CPD" refers to the value from compound-treated samples; "$[Cp^*IrCl_2]_2$" refers to dichloro(pentamethylcyclo-pentadienyl)iridium (III) dimer; "CPM" refers to counts per minute; "CT" refers to cyclic threshold; "DCC" refers to N,N'-dicyclohexylcarbodiimide; "DCM" refers to dichloromethane; "DIAD" refers to diisopropyl azodicarboxylate; "DIC" refers to N,N'-diisopropylcarbodiimide; "DIPEA" refers to N,N-diisopropylethylamine; "DLBCL" refers to diffuse large B-cell lymphoma; "DMEM" refers to Dulbecco's Modified Eagle's (tissue culture) medium; "DMSO" refers to dimethyl sulfoxide; "DNA" refers to deoxyribonucleic acid; "DNAse" refers to a deoxyribonuclease; "cDNA" refers to complementary DNA; "dNTP" refers to deoxynucleotide triphosphate; "DTT" refers to dithiothreitol; "EDCI" refers to 1-ethyl-3-(3-dimethylaminopropyl)carbodiimide hydrochloride; "EDTA" refers to ethylenediaminetetraacetic acid; "EGTA" refers to ethylene glycol-bis(2-aminoethylether)-N,N,N',N'-tetraacetic acid; "EtOAc" refers to ethyl acetate; "EtOH" refers to ethanol or ethyl alcohol; "FBS" refers to fetal bovine serum; "GAPDH" refers to glyceraldehyde-3-phosphate dehydrogenase; "GC" refers to gas chromatography; "$^3$H-SAM" refers to S-[methyl-$^3$H]-adenosyl-L-methionine; "HAT" refers to hypoxanthine-aminopterin-thymidine; "HATU" refers to [dimethylamino(triazolo[4,5-b]pyridin-3-yloxy)methylidene]-dimethylazanium hexafluorophosphate; "HBTU" refers to O-(benzotriazol-1-yl)-N,N,N',N'-tetramethyluronium hexafluorophosphate; "HOBt" refers to hydroxybenzotriazole; "HEC" refers to hydroxyethyl cellulose; "HEPES" refers to 4-(2-hydroxyethyl)piperazine-1-ethanesulfonic acid; "hr" refers to hour or hours; "HOAt" refers to 1-hydroxy-7-azabenzotriazole; "$IC_{50}$" refers to the concentration of an agent which produces 50% of the maximal inhibitory response possible for that agent; "IVTI" refers to in vivo target inhibition; "KLH" refers to keyhole limpet hemocyanin; "Lithium tri-sec-butylborohydride solution" refers to lithium tri(sec-butyl) borohydride; "MDM4" refers to mouse double minute 4; "MeOH" refers to methanol; "MEP50" refers to methylosome protein 50; "min" refers to minute or minutes; "MTBE" refers to methyl t-butyl ether; "OD" refers to optical density; "o.d." refers to outside diameter; "PAGE" refers to polyacrylamide gel electrophoresis; "PBS" refers to phosphate-buffered saline; "PCR" refers to polymerase chain reaction; "PEG" refers to polyethylene glycol; "pNPP" refers to 4-nitrophenyl phosphate; "PO" refers to per os or oral administration; "ppm" refers to parts per million; "PRMT5" refers to Protein Arginine Methyl Transferase 5; "PyBOP" refers to (benzotriazol-1-yl-oxytrispyrrolidinophosphonium hexafluorophosphate); "psig" refers to pound-force per square inch gauge; "PTFE" refers to polytetrafluoroethylene; "PyBROP" refers to bromo-trispyrrolidinophosphonium hexafluorophosphate; "QD" refers to quaque die or once daily administration; "qPCR" refers to quantitative polymerase chain reaction; "RNA" refers to ribonucleic acid; "RPMI" refers to Roswell Park Memorial Institute; "(R,R)-Ts-DENEB™" refers to N-[(1R,2R)-1,2-diphenyl-2-(2-(4-methylbenzyloxy)ethylamino)-ethyl]-4-methylbenzene sulfonamide(chloro)ruthenium(II); "(R,R)-Ts-DEPEN" refers to (1R,2R)-(−)-N-(4-toluenesulfonyl)-1,2-diphenylethylenediamine; "RT" refers to reverse transcriptase; "SAH" refers to S-adenosyl-homocysteine; "SAM" refers to S-adenosyl-methionine; "(S)-CBS catalyst" refers to (S)-Corey-Bakshi-Shibata catalyst or (S)-1-butyl-3,3-diphenylhexahydropyrrolo[1,2-c][1,3,2]oxazaborole; "sf9" refers to clonally derived *Spodoptera frugiperda* insect cells; "SmD1" refers to Small Nuclear Ribonucleoprotein D1; "SPA" refers to scintillation proximity assay; "SS" refers to stainless steel; "SWFI" refers to sterile water for injection; "TEA" refers to triethylamine; "Tris" and "TRIZMA®" refer to 2-amino-2-(hydroxymethyl)-1,3-propanediol or tris(hydroxymethyl)aminomethane; "TBS" refers to Tris-buffered saline; "TEMPO" refers to 2,2,6,6-tetramethylpiperidine 1-oxyl; "THF" refers to tetrahydrofuran, "TAME" refers to N-alpha-p-tosyl-L-arginine ester hydrochloride; "TPCK" refers to tosylphenylalanylchloromethane; "wt." refers to weight; "YSI" refers to yttrium silicate, and "*" refers to the mathematical operation of multiplication.

In the Schemes below, all substituents, unless otherwise indicated, are as previously defined. The reagents and starting materials are readily available to one of ordinary skill in the art. Others may be made by standard techniques of organic and heterocyclic chemistry or by the procedures described in the Preparations and Examples which follow including any novel procedures herein.

Scheme 1
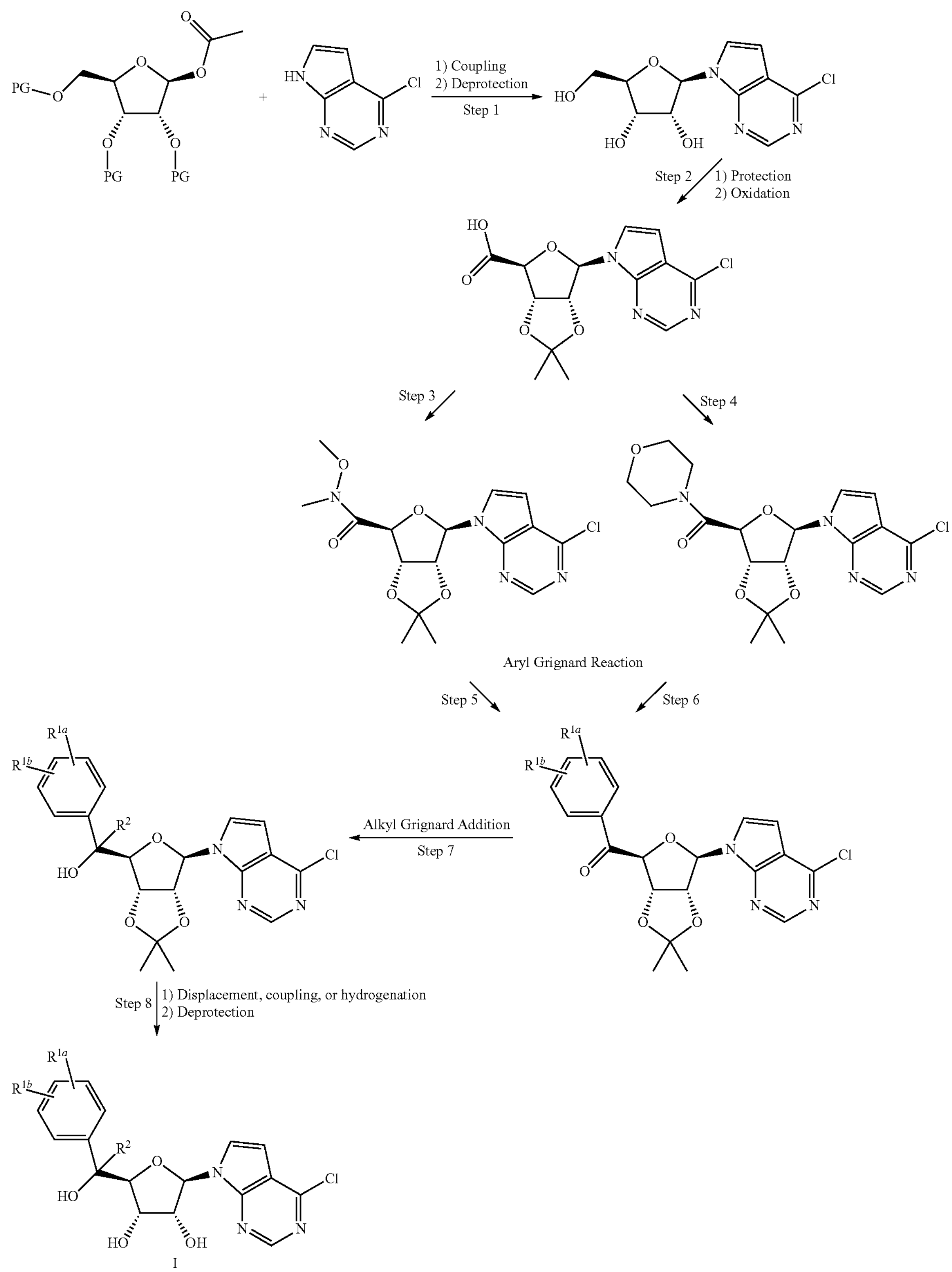
PG = Protecting Group

Scheme 1 depicts the formation of compounds of Formula I. "PG" is a protecting group developed for hydroxy groups. Such protecting groups are well known and appreciated in the art.

A tris-protected 1-acetylated ribofuranose is coupled with 4-chloro-7H-pyrrolo(2,3-d)pyrimidine at the pyrrolo nitrogen in Scheme 1, Step 1, substep 1 to give the protected product of Step 1. Trimethylsilyl trifluoromethanesulfonate combined with ethanimidic acid, N-(trimethylsilyl)-, trimethylsilyl ester can be used as an activating agent to couple the 4-chloro-7H-pyrrolo(2,3-d)pyrimidine to the protected ribofuranose using a solvent such as ACN. In a one pot 2 step procedure, the hydroxyl groups are deprotected under basic conditions using an inorganic base such as sodium methoxide in MeOH, and the 2,3-hydroxy substitutions of the ribose backbone are then selectively protected as a ketal using 2,2-dimethoxypropane with p-toluenesulfonic acid monohydrate as an activating agent in a solvent such as acetone to give the product of Scheme 1, Step 1, substep 2 followed by the product of Step 2, substep 1. The 5' alcohol is oxidized to the carboxylic acid using iodobenzene diacetate and a catalyst such as TEMPO in a solvent such as ACN at a temperature of from 0° C. to room temperature for about 1 hr to give the ketal carboxylic acid product of Scheme 1, Step 2, substep 2. The Weinreb amide product of Scheme 1, Step 3 can be prepared with N,O-dimethylhydroxylamine hydrochloride in a suitable solvent, such as EtOAc, using a peptide coupling agent such as 2,4,6-tripropyl-1,3,5,2,4,6-trioxatriphosphorinane-2,4,6-trioxide. An alternate amide, such as a morpholine amide, can be prepared with the carboxylic acid product of Scheme 1, Step 2 and an appropriate nucleophilic amine such as morpholine in a solvent such as DCM using a coupling reagent such as CDI. One skilled in the art will recognize that there are a number of methods and reagents for amide formation resulting from the reaction of carboxylic acids and amines. For example, the reaction of an appropriate amine with the carboxylic acid product of Scheme 1, Step 2 in the presence of a coupling reagent with or without an organic base such as DIPEA or triethylamine can provide a compound of Scheme 1, Step 3 or Scheme 1, Step 4. Coupling reagents include carbodiimides, such as DCC, DIC, and EDCI or a carbonyldiimidazole such as CDI. Amide coupling additives, such as HOBt and HOAt can also be used to enhance the reaction. Additionally, uronium or phosphonium salts of non-nucleophilic anions, such as HBTU, HATU, PyBOP, and PyBrOP could be used in place of the more traditional coupling reagents.

The Weinreb amide product of Scheme 1, Step 3 or the morpholine amide product of Scheme 1, Step 4 can be treated with a Grignard reagent to form the products of Scheme 1, Step 5 and Scheme 1, Step 6, respectively. One skilled in the art will recognize that an appropriate Grignard reagent can be reacted with the amide or a Grignard reagent can be generated in situ from a commercial Grignard reagent such as isopropylmagnesium chloride-lithium chloride complex with the appropriate bromo- or iodo-substituted benzene compound to give the products of Scheme 1, Step 5 and Scheme 1, Step 6. Or, alternatively the Grignard reagent can be generated in situ with the appropriate bromo- or chloro-substituted benzene compound with magnesium turnings and iodine to give the products of Scheme 1, Step 5.

The ketone product of Scheme 1, Step 5 and Scheme 1, Step 6 can be reacted in a second Grignard reaction to give the hydroxy product of Scheme 1, Step 7 where $R^2$ is not hydrogen and $R^2$ is as previously defined. The product of Scheme 1, Step 5 or Scheme 1, Step 6 is treated with the appropriate alkyl Grignard reagent in a solvent such as THF at a temperature of about 0° C. and upon quenching with 1 N HCl or aqueous ammonium chloride gives the product of Scheme 1, Step 7.

In Scheme 1, Step 8, substep 1, displacement, for products of Formula I where $R^3$=$NH_2$, a displacement of the 4-chloro of the pyrrolo pyrimidine to an amine can be accomplished with $NH_3$ such as 7 N $NH_3$ in MeOH. The reaction can be carried out in a sealed vessel and heating in a microwave at about 100° C. Alternatively, aqueous ammonium hydroxide (about 28-30% wt % in water) can be used to displace the chloride in a sealed vessel with heating at about 80-110° C. for about 8-24 hr.

In Scheme 1, Step 8, substep 1, coupling, for $R^3$=$CH_3$, the 4-chloro of the pyrrolo pyrimidine can be converted to the methyl under Pd coupling conditions using a palladium source such as tetrakis(triphenylphosphine)palladium(0) with $Al(CH_3)_3$ in a solvent such as THF or 1,4-dioxane under an inert atmosphere at a temperature of about 70-80° C.

In Scheme 1, Step 8, substep 1, hydrogenation, for $R^3$=H, the 4-chloro of the pyrrolopyrimidine can be removed under hydrogenation conditions. Hydrogenation of such compounds is well known and appreciated in the art.

In Scheme 1, Step 8, substep 2, the protected ketal can be deprotected under acidic conditions such as TFA in water or HCl, such as 4 N in dioxane and MeOH or 4.99 M in 2-propanol, and water to give compounds of Formula I. The deprotection of such compounds is well known and appreciated in the art.

Scheme 2

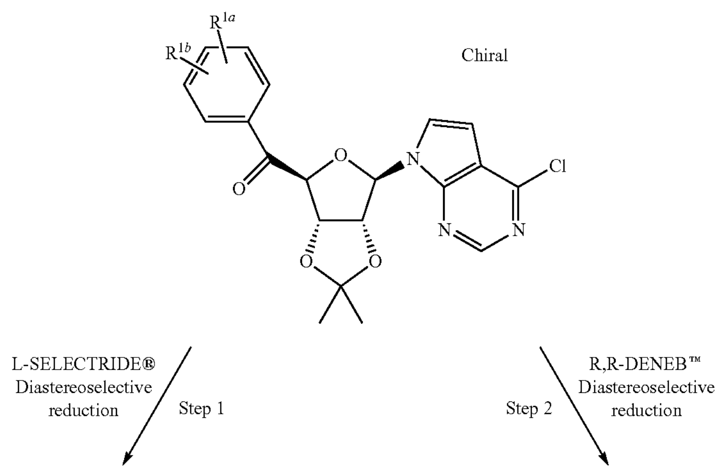

-continued

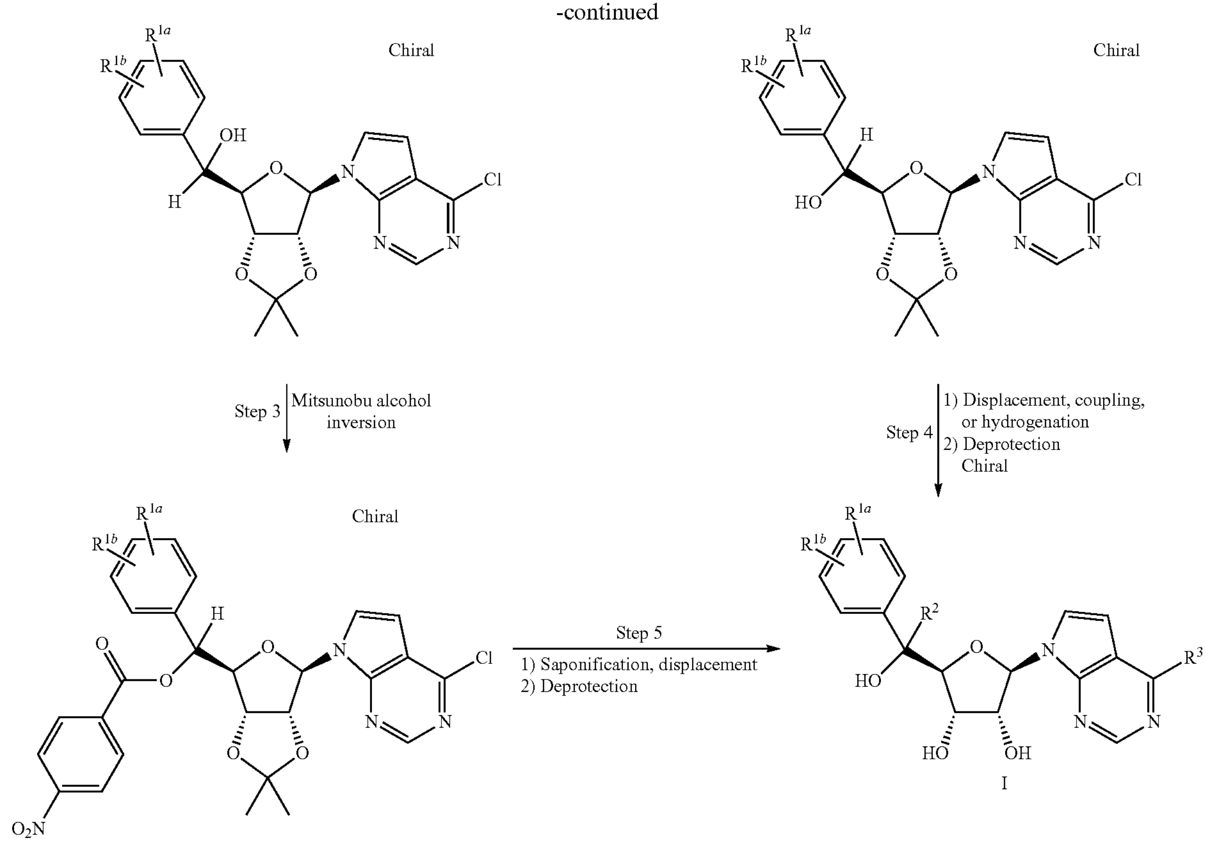

Alternatively in Scheme 2, the ketone product of Scheme 1, Step 5 or Step 6, for $R^2$=H, can be reduced in a diastereo-controlled manner using achiral or chiral reducing agents to give a hydroxy product enriched for one diastereomer. As an example, ketone reduction with lithium tri-sec-butylborohydride solution (L-SELECTRIDE®) in a solvent such as THF at a temperature of about −78° C. yields the hydroxyl product of Scheme 2, Step 1 as a diastereomerically enriched or major product. Alternatively in Scheme 2, Step 2, chiral reduction catalysts can selectively produce the hydroxyl product as an enriched or major diastereomer with hydroxyl stereoconfiguration opposite that produced with the Lithium tri-sec-butylborohydride solution conditions. Examples of such chiral catalysts that can be used include (S)-CBS-catalyst with borane-THF complex in a solvent such as THF at a temperature of about −15° C., or, alternatively, with an oxo-tethered ruthenium (II) complex catalyst such as (R,R)-Ts-DENEB™ with formic acid/triethylamine complex at about room temperature, or, alternatively, with an iridium (III) complex in a solvent mixture such as two-phase water/DCM system at about room temperature. One skilled in the art will recognize that the appropriate iridium (III) complex can be can be generated in situ from commercial $[Cp^*IrCl_2]_2$ and (R,R)-Ts-DEPEN to give the products of Scheme 2, Step 2.

The major or enriched diastereomers from the product of Scheme 2, Step 2 using the above chiral reduction catalysts, the (S)-CBS or (R,R)-DENEB™ or iridium(III) complex, generally are found to be the diastereo configuration of the formed hydroxyl center in the Examples described in this invention.

An alternative synthetic method to produce the compounds of the present invention uses a Mitsunobu reaction (Scheme 2, Step 3) involving a nucleophile such as 4-nitrobenzoic acid to react with the alcohol to form an ester. Mitsunobu reactions are well known in the art and involve converting an alcohol into an ester using an acid such as 4-nitrobenzoic acid, triphenylphosphine, and an azodicarboxylate such as diethyl azodicarboxylate (DEAD) or diisopropyl azodicarboxylate (DIAD) in a polar aprotic solvent such as THF at a temperature of about 0° C. to room temperature. During the Mitsunobu alcohol activation and displacement with the nucleophile, the alcohol stereocenter undergoes an inversion of stereochemistry. By this method using the Mitsunobu reaction, the enriched diastereomers produced from the Lithium tri-sec-butylborohydride solution reduction in Scheme 2, Step 1, can be converted to products with alcohol stereoconfiguration enriched for the same major diastereomer as produced with the (S)-CBS or (R,R)-Ts-DENEB™ or iridium (III) complex catalysts in Scheme 2, Step 2.

In Scheme 2, Step 5, substep 1, for products of Formula I where $R^3$=$NH_2$, the ester may then be saponified to the alcohol and the 4-chloro of the pyrrolo pyrimidine displaced with an amine in a one-pot reaction in the same manner as discussed for Scheme 1, Step 8. In Scheme 2, Step 5, substep 2, the protected ketal can be deprotected under acidic conditions as discussed in Scheme 1, Step 8, substep 2 to give compounds of Formula I.

In Scheme 2, Step 4, the product of Scheme 2, Step 2 for $R^3$=$NH_2$, $CH_3$, or H can be accomplished as discussed in Scheme 1, Step 8, substep 1, or, alternatively, aqueous ammonium hydroxide (about 28-30% wt % in water) and dioxane can be used to displace the chloride using continuous flow chemistry with heating at about 200° C. and a flow rate of 10 mL/min (30 min residence time) or, alternatively at about 200° C. and a flow rate 0.251 mL/min (30 min residence time). In Scheme 2, Step 4, substep 2, the protected ketal can be deprotected as discussed in Scheme 1, Step 8, substep 2, or, alternatively, protected ketal can be deprotected with aqueous HCl (about 6 N in water) in a EtOH/MeOH/EtOAc mixture using continuous flow chemistry with heating at about 55° C. and a flow rate of 1.5 mL/min (20 min residence time) or with aqueous HCl (about 4 N in water) in a EtOH at about 82° C. and a flow rate 0.288 mL/min (10 min residence time) to give compounds of Formula I.

One skilled in the art will realize that generally the $^{1}H$ NMR spectra of the compounds exemplified can be used to determine the identity as well as the extent of diastereomeric enrichment or purity of the produced single diastereomers.

In an optional step, a pharmaceutically acceptable salt of a compound of Formula I can be formed by reaction of an appropriate free base of Formula I with an appropriate pharmaceutically acceptable acid in a suitable solvent under standard conditions. The formation of such salts is well known and appreciated in the art.

The compounds of the present invention are prepared as illustrated in the Examples below. The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The diastereomeric configurations of the compound of the invention may be determined by standard techniques such as X-ray analysis, $^{1}H$ nmr, and correlation with chiral-HPLC retention time.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.0 μm; gradient: 5-100% B in 3 mM, then 100% B for 0.75 mM column temperature: 50° C.+/−10° C.; flow rate: 1.2 ml/min; Solvent A: deionized water with 0.1% HCOOH; Solvent B: ACN with 0.1% formic acid; wavlength 214 nm Alternate LC-MS conditions (high pH): column: XTERRA® MS C18 columns 2.1×50 mm, 3.5 μm; gradient: 5% of solvent A for 0.25 mM, gradient from 5% to 100% of solvent B in 3 mM and 100% of solvent B for 0.5 min or 10% to 100% of solvent B in 3 mM and at 100% of solvent B for 0.75 mM; column temperature: 50° C.+/−10° C.; flow rate: 1.2 mL/min; Solvent A: 10 mM $NH_4HCO_3$ pH~9-10; Solvent B: ACN; wavelength: 214 nm.

NMR spectra are performed on a Bruker AVIII HD 400 MHz NMR Spectrometer, obtained as $CDCl_3$ or $(CD_3)_2SO$ solutions reported in ppm (chemical shift 6), using residual solvent [$CDCl_3$, 7.26 ppm; $(CD_3)_250$, 2.05 ppm] as reference standard. When peak multiplicities are reported, the following abbreviations may be used: s (singlet), t (triplet), q (quartet), m (multiplet), br-s or bs (broad singlet), dd (doublet of doublets), dt (doublet of triplets), and td (triplet of doublets). Coupling constants (J), when reported, are reported in hertz (Hz).

PREPARATION 1

[(2R,3R,4R,5R)-3,4-Dibenzoyloxy-5-(4-chloropyrrolo[2,3-d]pyrimidin-7-yl)tetrahydrofuran-2-yl]methyl benzoate Suspend 4-chloro-7H-pyrrolo-(2,3-d)pyrimidine (55.3 g, 0.36 mol) in ACN (1.8 L) and stir at room temperature. Add ethanimidic acid, N-(trimethylsilyl)-, trimethylsilyl ester (110.8 mL, 0.45 mol) drop wise and stir the mixture for 20 min at room temperature under $N_2$. Add trimethylsilyl trifluoromethanesulfonate (1.0 L, 0.54 mol) drop wise followed by the portion wise addition of [(2R,3R,4R,5S)-5-acetoxy-3,4-dibenzoyloxy-tetrahydrofuran-2-yl]methyl benzoate (272.4 g, 0.54 mol). Heat the mixture for 4 hr at 85° C. (internal). Cool the mixture to 40° C. (internal) and add additional [(2R,3R,4R,5S)-5-acetoxy-3,4-dibenzoyloxy-tetrahydrofuran-2-yl]methyl benzoate (45.40 g, 90.0 mmol) portion wise to the mixture. Heat the reaction mixture for 2 hr at 85° C. (internal). Stir the mixture for a further 18 hr under $N_2$ at room temperature. Add water (500 mL) and EtOAc (500 mL) to the reaction. Separate the resulting organic layer. Extract the aqueous layer with EtOAc (3×250 mL). Combine the organic extracts and wash with saturated aqueous $NaHCO_3$ (500 mL) and saturated aqueous sodium chloride (500 mL). Dry the organic layer over sodium sulfate, filter, and remove the solvents under reduced pressure. Purify via silica gel chromatography eluting with a gradient of 10-30% EtOAc/hexanes to give the title compound (98.0 g, 41% yield) as a colorless oil. ES/MS m/z ($^{35}Cl/^{37}Cl$) 598.0/600.0 $[M+H]^+$.

PREPARATION 2

[(3aR,4R,6R,6aR)-4-(4-Chloropyrrolo[2,3-d]pyrimidin-7-yl)-2,2-dimethyl-3a,4,6,6a-tetrahydrofuro[3,4-d][1,3]dioxol-6-yl]methanol Suspend [(2R,3R,4R,5R)-3,4-dibenzoyloxy-5-(4-chloropyrrolo[2,3-d]pyrimidin-7-yl)tetrahydrofuran-2-yl]methyl benzoate (80.5 g, 134.61 mmol) in MeOH (805 mL) and treat with a solution of 0.5 M sodium methoxide in MeOH (53.8 mL, 26.92 mmol) at room temperature for 3 hr. Cool to 0° C. and treat the mixture with DOWEX® 50WX2 resin (up to pH<5). Filter and concentrate in vacuo to give a residue. Triturate from MTBE (100 mL). Decant the mixture and dry the resulting residue to give a white solid. Suspend the solid in acetone (1100 mL) and add 2,2-dimethoxypropane (41.5 mL, 336.5 mmol) and p-toluenesulfonic acid monohydrate (25.6 g, 134.6 mmol) to the mixture. Stir the reaction mixture for 3 hr at room temperature. Remove up to ~⅓ of the solvent under reduced pressure and add DCM (250 mL) and water (100 mL). Separate the organic layer and extract the aqueous layer with DCM (2×100 mL). Combine the organic extracts and wash with saturated aqueous $NaHCO_3$ (150 mL; pH-9) and saturated aqueous sodium chloride (100 mL). Dry the organic layer over sodium sulfate. Filter and remove the solvents under reduced pressure to give a crude mixture. Purify via silica gel chromatography eluting with 30% EtOAc in DCM to give the title compound (26.5 g, 60% yield) as colorless oil. ES/MS m/z ($^{35}Cl/^{37}Cl$) 326.0/328.0 $[M+H]^+$.

PREPARATION 3

(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxole-6-carboxylic acid Dissolve [(3aR,4R,6R,6aR)-4-(4-chloropyrrolo[2,3-d]pyrimidin-7-yl)-2,2-dimethyl-3a,4,6,6a-tetrahydrofuro[3,4-d]

[1,3]dioxol-6-yl]methanol (60.0 g, 184.2 mmol) in ACN (250 mL). Add water (180 mL) and cool the mixture to 0° C. Add iodobenzene diacetate (160 g, 496.8 mmol) portion wise at 0° C. followed by the portion wise addition of TEMPO (14 g, 89.6 mmol). Stir the mixture for 1 hr at room temperature. Remove the solvent under reduced pressure and dissolve the crude residue in EtOAc (300 mL). Add water (100 mL) at 0° C. and separate the resulting organic layer. Extract the aqueous with EtOAc (3×100 mL). Combine the organic extracts and wash with a 10% aqueous solution of thiosulfate (2×100 mL) and water (2×100 mL). Dry the organic layer over sodium sulfate, filter, and remove the solvents under reduced pressure to give a pale yellow solid. Mix the crude material with hexanes (400 mL) and stir the mixture for 1 hr at room temperature. Filter the resulting solid, wash with hexanes (100 mL), and dry to give the title compound (66.7 g, 89% purity, 100% crude) as a yellow solid. ES/MS m/z ($^{35}$Cl/$^{37}$Cl) 340.00/342.00 [M+H]$^+$.

PREPARATION 4

(3aR,4R,6S,6 aS)-4-(4-Chloropyrrolo[2,3-d]pyrimidin-7-yl)-N-methoxy-N,2,2-trimethyl-3a,4,6,6a-tetrahydrofuro[3,4-d][1,3]dioxole-6-carboxamide Dissolve [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (45.0 g, 138.1 mmol) in ACN (175 mL). Add water (133 mL) and cool the mixture to 0° C. Add iodobenzene diacetate (122.3 g, 379.7 mmol) portion wise at 0° C. followed by the portion wise addition of TEMPO (10.5 g, 67.0 mmol). Stir the mixture for 1 hr at room temperature. Add water (100 mL) and EtOAc (250 mL) at 0° C. and separate the resulting organic layer. Extract the aqueous layer with EtOAc (3×100 mL). Combine the organic extracts and wash with water (100 mL), 20% w/v aqueous solution of sodium bisulphite (100 mL), and water (100 mL). Dry the organic layer over sodium sulfate, filter, and remove the solvents under reduced pressure to give a brown solid (53.0 g). Dissolve this solid in EtOAc (400 mL) at room temperature and add N,O-dimethylhydroxylamine hydrochloride (18.8 g, 193.0 mmol) portion wise. Stir the mixture for 5 min at room temperature and drop wise add a 1.67 M solution of 2,4,6-tripropyl-1,3,5,2,4,6-trioxatriphosphorinane-2,4,6-trioxide in EtOAc (176.3 mL, 294 mmol). Stir the reaction mixture at room temperature for 3 days under $N_2$. Cool the reaction mixture to 0° C. and add water (150 mL) and EtOAc (150 mL). Separate the resulting organic layer and extract the aqueous layer with EtOAc (3×150 mL). Combine the organic extracts and wash with water (200 mL). Dry the organic layer over sodium sulfate, filter, and concentrate to give a crude mixture. Purify by filtration through a silica plug eluting with a gradient of 0-30% EtOAc/DCM to give the title compound as a white vitreous solid (31.0 g, 60% over two steps). ES/MS m/z ($^{35}$Cl/$^{37}$Cl) 383.0/385.0 [M+H].

PREPARATION 5

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-morpholino-methanone Suspend (3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxole-6-carboxylic acid (63.7 g, 166 mmol) in DCM (320 mL) and stir at 0° C. Add 1,1'-carbonyldiimidazole (37.7 g, 232 mmol) portion wise and stir the mixture at room temperature for 45 min Add morpholine (21.7 g, 249 mmol) drop wise to the mixture and stir at room temperature for 3 days. Dilute the reaction mixture with DCM and water (150 mL). Separate the resulting organic layer and extract the aqueous layer with DCM (3×100 mL). Combine the organic extracts and wash with water (100 mL) and saturated aqueous sodium chloride (100 mL). Dry the organic layer over sodium sulfate, filter, and remove the solvents under reduced pressure. Purify via silica gel chromatography eluting with a gradient of 20-60% EtOAc/hexanes to give the title compound (34 g, 50% yield) as a brown foam. ES/MS m/z ($^{35}$Cl/$^{37}$Cl) 409.00/411.00 [M+H]$^+$.

PREPARATION 6

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-phenyl-methanone Add drop wise a 3.0 M solution of phenylmagnesium bromide in diethyl ether (1.79 ml, 5.38 mmol) to a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-morpholino-methanone (1.00 g, 2.45 mmol) in THF (15 mL) over 2 min at 0° C. Stir at 0° C. for 30 min, and add 1 N aqueous HCl (7.3 mL). After 3 min, extract the aqueous layer with DCM. Separate the layers and evaporate the organic layer under reduced pressure. Purify via silica gel chromatography eluting with a gradient of 35-75% of a 10% mixture of MTBE/DCM in hexanes over 25 min to give the title compound (893 mg, 91% yield). ES/MS m/z ($^{35}$Cl/$^{37}$Cl) 400.0/402.0 [M+H]$^+$.

PREPARATION 7

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanone Dissolve (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (30.0 g, 78.4 mmol) in THF (300 mL) and cool to −10° C. Add a 1.0 M solution of 4-chlorophenylmagnesium bromide in diethyl ether (157 mL, 157 mmol) drop wise and stir the mixture for 1 hr at room temperature. Cool to 0° C. and quench the reaction mixture by adding saturated aqueous ammonium chloride (50 mL) and EtOAc (200 mL). Separate the resulting organic layer and extract the aqueous layer with EtOAc (3×100 mL). Combine the organic extracts, wash with water (250 mL), and dry over sodium sulfate. Filter and remove the organic filtrate under reduced pressure to give a crude mixture. Purify via silica gel chromatography eluting with a gradient of 0-15% EtOAc/DCM to give the title compound as a white solid (30.1 g, 84% yield). ES/MS m/z ($^{35}$Cl/$^{37}$Cl) 434.0/436.0 [M+H]$^+$.

ALTERNATE PREPARATION 7

Dissolve (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (257.0 g, 617.7 mmol) in THF (2570 mL) and cool to −15° C. Add a 1.0 M solution of 4-chlorophenylmagnesium bromide in 2-methyltetrahydrofuran (1050 mL, 1050 mmol) drop wise and stir the mixture for 1 hr at −15° C. Quench the reaction mixture by adding saturated aqueous ammonium chloride (1000 mL) and water (500 mL). Separate the resulting organic layer and extract the aqueous layer with EtOAc (2×500 mL). Combine the organic extracts and dry over sodium sulfate. Filter and evaporate the filtrate under reduced pressure to give a white solid. Purify by recrystallization from EtOH (5300 mL) to give the title compound as a white solid (238.3 g, 87% yield). ES/MS m/z ($^{35}$Cl/$^{37}$Cl) 434.0/436.0 [M+H]$^+$.

PREPARATION 8

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-[4-(trifluoromethyl)phenyl]methanone Add drop wise 1-bromo-4-(trifluoromethyl)benzene (4.0 g, 18 mmol) to a 2.0 M solution of isopropylmagnesium chloride in THF (8 mL, 16 mmol) in additional THF (10 mL) at room temperature. Stir the mixture for 24 hr at room temperature. To this mixture, add a solution of (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (3.4 g, 8.9 mmol) in THF (14 mL) drop wise at room temperature and stir for 2 hr at room temperature. Cool to 0° C. and quench the reaction with a 10% solution of citric acid (100 mL). Add MTBE (200 mL) and stir the mixture for 20 min Separate the two phases and extract the aqueous layer with MTBE. Combine the organic extracts, wash with saturated aqueous ammonium chloride, water, and saturated aqueous sodium chloride. Dry the organic layer over sodium sulfate, filter, and remove the solvents under reduced pressure to give a residue. Purify the residue by silica gel chromatography eluting with a gradient of 0-50% EtOAc/hexanes to give the title compound (3.60 g, 87% yield) as a yellow foam. ES/MS m/z ($^{35}$Cl/$^{37}$Cl) 468.00/470.00 [M+H]$^+$.

PREPARATION 9

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-(3-chlorophenyl)methanone Dissolve 1-chloro-3-iodobenzene (0.42 g, 1.7 mmol) in THF (5 mL), and cool to 0° C. Add a 1.3 M in THF solution of isopropylmagnesium chloride-lithium chloride complex (1.23 mL, 1.6 mmol) drop wise over 10 min, and stir at 0° C. for 1 hr. Add a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-morpholino-methanone (0.5 g, 1.2 mmol) in THF (5 mL) at 0° C. After 1 hr of stirring at 0° C., quench the mixture by adding 1 N aqueous HCl (2 mL). Dilute the resulting mixture with EtOAc and wash the organic layer with water and saturated aqueous sodium chloride. Dry the organic layer over sodium sulfate, filter, and concentrate the filtrate under reduced pressure. Purify via silica gel chromatography eluting with a gradient of 0-25% EtOAc/hexanes over 20 min to give the title compound (0.35 g, 66% yield). ES/MS m/z ($^{35}$Cl/$^{37}$Cl) 434.2/436.2 [M+H]$^+$.

PREPARATION 10

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-(4-chloro-2-fluoro-phenyl)methanone Dissolve 4-chloro-2-fluoro-1-iodo-benzene (1.9 g, 7.5 mmol) in THF (50 mL), and cool to 0° C. Add a 1.3 M solution of isopropylmagnesium chloride-lithium chloride complex in THF (6.3 mL, 8.2 mmol), and stir at 0° C. for 1 hr. Add a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-morpholino-methanone (2.8 g, 6.8 mmol) in THF (10 mL) at 0° C. After 5 hr of stirring at 0° C., quench the mixture by adding 1 N aqueous HCl (9.09 mL, 9.09 mmol). Dilute the resulting mixture with EtOAc, and wash the organic layer with water and saturated aqueous sodium chloride. Dry the organic extracts over sodium sulfate, filter, and concentrate the filtrate under reduced pressure. Purify via silica gel chromatography eluting with a gradient of 0-50% EtOAc/hexanes to give the title compound (1.57 g, 51% yield). ES/MS m/z ($^{35}$Cl/$^{37}$Cl) 452.0/454.0/456 [M+H]$^+$.

PREPARATION 11

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-(3-ethylphenyl)methanone Add drop wise over 10 min a 0.5 M solution of 3-ethylphenylmagnesium bromide in THF (5.8 mL, 2.9 mmol) to a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-morpholino-methanone (1.0 g, 2.5 mmol) in THF (10 mL) at 0° C. Stir at 0° C. for 30 min and quench by adding 1 N aqueous HCl (3.9 mL, 3.9 mmol). Dilute with water, and extract the aqueous layer with EtOAc. Dry the organic extracts over sodium sulfate, filter, and evaporate the filtrate under reduced pressure. Purify the residue via silica gel chromatography eluting with a gradient of 0-100% EtOAc/hexanes over 30 min to give the title compound (0.98 g, 94% yield). ES/MS m/z ($^{35}$Cl/$^{37}$Cl) 428/430 [M+H]$^+$.

PREPARATION 12

4-[(3aR,4R,6S,6 aS)-4-(4-Chloropyrrolo[2,3-d]pyrimidin-7-yl)-2,2-dimethyl-3a,4,6,6a-tetrahydrofuro[3,4-d][1,3]dioxole-6-carbonyl]benzonitrile Dissolve 4-bromobenzonitrile (1.36 g, 7.40 mmol) in THF (10 mL) at 0° C. Add a 1.3 M solution of isopropylmagnesium chloride-lithium chloride complex in THF (6.6 mL, 8.53 mmol) and stir at 0° C. for 2 hr. Cannulate this mixture into a solution of (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (2.18 g, 5.68 mmol) in THF (14 mL) at 0° C. Warm to room temperature and stir 2 hr. Quench by adding 1 N aqueous HCl (9.09 mL) at 0° C. Dilute the reaction mixture with EtOAc and water. Separate the layers and extract the aqueous layer with EtOAc. Combine the organic extracts and wash with saturated aqueous bicarbonate and saturated aqueous sodium chloride. Dry the organic layer over magnesium sulfate, filter, and concentrate the filtrate under reduced pressure. Purify the residue via silica gel chromatography eluting with a gradient of 15-30% EtOAc in hexanes to give the title compound (1.49 g, 62% yield). ES/MS m/z ($^{35}$Cl/$^{37}$Cl) 425.0/427.0 [M+H]$^+$.

PREPARATION 13

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-(3,4-difluorophenyl)methanone Add 4-bromo-1,2-difluoro-benzene (2.21 g, 1.29 mL, 11.4 mmol) to a 2.0 M solution of isopropylmagnesium chloride in THF (6.05 mL, 12.1 mmol) at −15° C. and stir for 15 min Warm the reaction mixture and stir at 0° C. for 1 hr. Add this mixture to a solution of (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (1.25 g, 3.27 mmol) in THF (16.3 mL) at 0° C. After 15 min, quench by adding 1 N aqueous HCl (5 mL). Dilute the reaction mixture with EtOAc (30 mL) and vigorously stir the biphasic mixture at room temperature for 15 min Separate the layers and extract the aqueous layer with EtOAc (2×40 mL). Combine the organic extracts and wash with saturated aqueous bicarbonate and saturated aqueous sodium chloride. Dry the organic layer over magnesium sulfate, filter, and evaporate the filtrate under reduced pressure. Purify the residue via silica gel chromatography eluting with 4% EtOAc/DCM to give the title compound (1.12 g, 74% yield). ES/MS m/z ($^{35}$Cl/$^{37}$Cl) 436, 438 [M+H]$^+$.

PREPARATION 14

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanone Add 1-bromo-3,4-dichlorobenzene (1.04 g, 4.57 mmol) to a 2.0 M solution of isopropylmagnesium chloride-lithium chloride complex in THF (1.2 mL, 2.4 mL) at −15° C. After 15 min, warm the mixture to 0° C. and stir for 1 hr. Add this mixture to a solution of (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (0.50 g, 1.31 mmol) in THF (6.5 mL) at 0° C. and stir for 10 min Quench with 1 N aqueous HCl (5 mL), and add EtOAc (30 mL). Vigorously stir at room temperature for 15 min Separate the layers and extract the aqueous layer with EtOAc (2×40 mL). Combine the organic extracts and wash with saturated aqueous bicarbonate and saturated aqueous sodium chloride. Dry the organic layer over magnesium sulfate, filter, and remove the solvents under reduced pressure. Purify via silica gel chromatography eluting with a gradient of 10-20% EtOAc/hexanes to give the title compound (1.49 g, 62% yield). ES/MS m/z ($^{35}$Cl/$^{37}$Cl) 468/470 [M+H]$^+$.

PREPARATION 15

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-(p-tolyl)methanone Add a 1.0 M solution of p-tolylmagnesium bromide in THF (2.4 mL, 2.4 mmol) drop wise to a stirring solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-morpholino-methanone (500 mg, 1.22 mmol) in THF (6.1 mL) at −15° C. After 1 hr, quench with saturated aqueous ammonium chloride (15 mL) and extract with EtOAc (3×40 mL). Combine the organic extracts and wash with saturated aqueous bicarbonate and saturated aqueous sodium chloride. Dry the organic layer over magnesium sulfate, filter, and concentrate the filtrate under reduced pressure. Purify the residue via silica gel chromatography eluting with a gradient of 10-20% EtOAc/hexanes to give the title compound (405.3 mg, 80% yield). ES/MS m/z ($^{35}$Cl/$^{37}$Cl) 414/416 [M+H]$^+$.

PREPARATION 16

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-(4-fluorophenyl)methanone Add a 1.0 M solution of 4-fluorophenylmagnesium bromide in THF (9.8 mL, 9.8 mmol) to a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-morpholino-methanone (2.0 g, 4.90 mmol) in THF (20 mL) at 0° C. Stir for 15 min at 0° C., then at room temperature for 1.5 hr. Cool the mixture to 0° C. and add saturated ammonium chloride (12 mL). Add EtOAc (25 mL) and vigorously stir at room temperature for 15 min Separate the layers and extract the aqueous layer with EtOAc (2×25 mL). Combine the organic extracts and wash with saturated aqueous bicarbonate and saturated aqueous sodium chloride. Dry the organic layer over sodium sulfate, filter, and evaporate the filtrate under reduced pressure. Purify via silica gel chromatography eluting with a gradient of 2-10% EtOAc/DCM to give the title compound (1.76 g, 83% yield). ES/MS m/z ($^{35}$Cl/$^{37}$Cl) 418/420 [M+H]$^+$.

PREPARATION 17

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-(2-fluorophenyl)methanone Dissolve 1-bromo-2-fluorobenzene (2.39 g, 7.88 mmol) in THF (15 mL) at 0° C. Add a 1.3 M solution of isopropylmagnesium chloride-lithium chloride complex in THF (9.1 mL, 11.8 mmol) and stir at 0° C. for 1.5 hr. Cannulate this mixture into a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-morpholino-methanone (2.93 g, 7.17 mmol) in THF (30 mL) at 0° C. and stir for 45 min Allow the mixture to warm to room temperature and stir for 2 hr. Cool the reaction to 0° C. and quench by adding 1 N aqueous HCl (11.5 mL). Dilute the reaction mixture with EtOAc and water. Separate the layers and extract the aqueous layer with EtOAc. Combine the organic extracts and wash with saturated aqueous $NaHCO_3$ and saturated aqueous sodium chloride. Dry the organic layer over magnesium sulfate, filter, and concentrate the filtrate under reduced pressure. Purify the crude material via silica gel chromatography eluting with a gradient of 10-70% MTBE/hexanes to give the title compound (2.14 g, 71% yield). ES/MS m/z ($^{35}$Cl/$^{37}$Cl) 418.0/420.0 [M+H]$^+$.

PREPARATION 18

[(3aR,4R,6S,6aS)-4-(4-Chloropyrrolo[2,3-d]pyrimidin-7-yl)-2,2-dimethyl-3a,4,6,6a-tetrahydrofuro[3,4-d][1,3]dioxol-6-yl]-[2-(trifluoromethyl)phenyl]methanone Dissolve 2-bromobenzotrifluoride (2.97 g, 13.1 mmol) in THF (15 mL) at 0° C. Add a 1.3 M solution of isopropylmagnesium chloride-lithium chloride complex in THF (8.6 mL, 11.2 mmol) and stir at 0° C. for 1.5 hr. Warm the mixture to room temperature and stir for 30 min. Cool the mixture again to 0° C. and cannulate this mixture into a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-morpholino-methanone (3.05 g, 7.46 mmol) in THF (20 mL) at 0° C. and stir for 2.5 hr. Allow the mixture to warm to room temperature and stir for 1 hr. Cool the mixture to 0° C. and add 1 N aqueous HCl (14.9 mL). Dilute the mixture with EtOAc and water. Separate the layers and extract the aqueous layer with EtOAc. Combine the organic extracts and wash with saturated $NaHCO_3$ and saturated aqueous sodium chloride. Dry the organic layer over magnesium sulfate, filter, and concentrate the filtrate under reduced pressure. Purify via silica gel chromatography eluting with a gradient of 25-50% MTBE/hexanes to give the title compound (1.48 g, 42% yield). ES/MS m/z ($^{35}Cl/^{37}Cl$) 468.0/470.0 [M+H]$^+$.

PREPARATION 19

[(3aR,4R,6S,6aS)-4-(4-aminopyrrolo[2,3-d]pyrimidin-7-yl)-2,2-dimethyl-3a,4,6,6a-tetrahydrofuro[3,4-d][1,3]dioxol-6-yl]-[4-chloro-3-(cyclopropoxy)phenyl]methanone Stir a mixture of magnesium turnings (4.97 g, 204 mmol) and iodine (920 mg, 3.63 mmol) in THF (150 mL) for 10 min at room temperature. Slowly add a solution of 4-bromo-1-chloro-2-(cyclopropoxy)benzene (46.0 g, 186 mmol) in THF (400 mL) drop wise and reflux the mixture for 30 min Cool to 40° C. and slowly add this mixture drop wise to a solution of (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (35.0 g, 91.6 mmol) in THF (400 mL) over 10 min. Stir the resulting mixture for 30 min at room temperature. Cool to 0° C. and quench the reaction mixture by adding saturated aqueous ammonium chloride (200 mL) and MTBE (200 mL). Separate the resulting organic layer and extract the aqueous layer with MTBE (2×200 mL). Combine the organic extracts, wash with water (150 mL), saturated aqueous sodium chloride (100 mL) and dry over sodium sulfate. Filter and concentrate the filtrate under reduced pressure to give a crude mixture. Purify by trituration from MTBE (80 mL) and heptane (400 mL) to give the title compound (48.8 g, 89.9% yield). ES/MS m/z ($^{35}Cl/^{37}Cl$) 490.0/492.0 [M+H]t $^1$H NMR (300 MHz, $CDCl_3$) δ 0.85-0.89 (m, 4H), 1.44 (s, 3H), 1.69 (s, 3H), 3.74-3.83 (m, 1H), 5.46-5.48 (m, 2H), 5.68 (dd, J=2.2, 6.1 Hz, 1H), 6.39 (d, J=0.6 Hz, 1H), 6.59 (d, J=3.6 Hz, 1H), 7.34-7.42 (m, 3H), 7.65 (d, J=1.8 Hz, 1H), 8.45 (s, 1H).

PREPARATION 20

(1R)-1-[(3aR,4R,6S,6aR)-4-(4-Chloropyrrolo[2,3-d]pyrimidin-7-yl)-2,2-dimethyl-3a,4,6,6a-tetrahydrofuro[3,4-d][1,3]dioxol-6-yl]-1-(4-chlorophenyl)ethanol Dissolve [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanone (15.9 g, 36.6 mmol) in THF (175 mL) and cool to 0° C. Add a 3.4 M solution of methylmagnesium bromide in 2-methyltetrahydrofuran (21.53 mL, 73.3 mmol) drop wise and stir the mixture for 2 hr at 0° C. Quench the reaction mixture with saturated aqueous ammonium chloride (50 mL) and then add EtOAc (250 mL). Separate the resulting organic layer and extract the aqueous layer with EtOAc (3×100 mL). Combine the organic extracts, wash with water (100 mL), and dry over sodium sulfate. Filter and concentrate the filtrate under reduced pressure to give a white vitreous solid. Purify via silica gel chromatography eluting with a gradient of 10-15% EtOAc/hexanes to give the title compound (11.5 g, 70% yield). ES/MS m/z ($^{35}Cl/^{37}Cl$) 450.00/452.00 [M+H]$^+$.

PREPARATION 21

Diastereomer of 1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol Dissolve [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanone (0.50 g, 1.07 mmol) in THF (5.3 mL) and cool to 0° C. Slowly add a 3.0 M solution of methylmagnesium bromide in diethyl ether (0.53 mL, 1.60 mmol) and stir at 0° C. for 1 hr. Quench by adding saturated ammonium chloride (20 mL). Dilute with EtOAc (40 mL) and separate the layers. Extract the aqueous layer with additional EtOAc (3×40 mL). Combine the organic extracts and wash with saturated aqueous bicarbonate followed by saturated aqueous sodium chloride. Dry the organic layer over magnesium sulfate, filter, and concentrate the filtrate under reduced pressure. Purify via silica gel chromatography, eluting with a gradient of 25-30% MTBE/hexanes to give the title compound (342 mg, 66% yield). ES/MS m/z ($^{35}Cl/^{37}Cl$) 484/486 [M+H]$^+$.

PREPARATION 22

Diastereomer of 1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(2-fluorophenyl)ethanol Dissolve [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(2-fluorophenyl)methanone (0.685 g, 1.64 mmol) in THF (20 mL) and cool the mixture to 0° C. Add a 3 M solution of methylmagnesium bromide in diethyl ether (1.09 mL, 3.27 mmol) and stir for 2 hr at 0° C. Quench the reaction by adding 1 N aqueous HCl (3.44 mL). Dilute the reaction mixture with EtOAc and water. Separate the layers and extract the aqueous layer with EtOAc. Combine the organic extracts and wash with saturated aqueous $NaHCO_3$ and saturated aqueous sodium chloride. Dry the organic layer over magnesium sulfate, filter, and concentrate the filtrate under reduced pressure. Purify the material via silica gel chromatography eluting with a gradient of 10-75% MTBE in hexanes to give the title compound as a diastereomer (0.482 g, 68% yield). ES/MS m/z ($^{35}Cl/^{37}Cl$) 434.0/436.0 [M+H]$^+$.

PREPARATION 23

Diastereomer of 1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-[2-(trifluoromethyl)phenyl]ethanol Dissolve [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-[2-(trifluoromethyl)phenyl]methanone (0.434 g, 0.928 mmol) in THF (12 mL) and cool the mixture to 0° C. Add a 3.0 M solution of methylmagnesium bromide in diethyl ether (0.62 mL, 1.86 mmol) and stir for 30 min at 0° C. Quench the reaction by adding 1 N aqueous HCl (1.95 mL). Dilute the reaction mixture with EtOAc and water. Separate the layers and extract the aqueous layer with EtOAc. Combine the organic extracts and wash with saturated aqueous $NaHCO_3$ and saturated aqueous sodium chloride. Dry the organic layer over magnesium sulfate, filter, and concentrate the filtrate under reduced pressure. Purify the resulting residue via silica gel chromatography, eluting with a gradient of 10-50% MTBE in hexanes, to give the title compound as a diastereomer (0.202 g, 45% yield). ES/MS m/z ($^{35}Cl/^{37}Cl$) 484.0/486.0 $[M+H]^+$.

PREPARATION 24

1-[(3aR,4R,6S,6aR)-4-(4-Chloropyrrolo[2,3-d]pyrimidin-7-yl)-2,2-dimethyl-3a,4,6,6a-tetrahydrofuro[3,4-d][1,3]dioxol-6-yl]-1-[4-(trifluoromethyl)phenyl]ethanol Dissolve [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-[4-(trifluoromethyl)phenyl]methanone (0.425 g, 0.908 mmol) in THF (10 mL) and cool the mixture to 0° C. Add a 3.0 M solution of methylmagnesium bromide in diethyl ether (0.45 mL, 1.35 mmol) and stir for 1 hr at 0° C. Quench the reaction by adding 1 N aqueous HCl (1.45 mL). Dilute the mixture with EtOAc and water. Separate the layers and extract the aqueous layer with EtOAc. Combine the organic extracts and wash with saturated aqueous $NaHCO_3$ and saturated aqueous sodium chloride. Dry the organic layer over magnesium sulfate, filter, and concentrate the filtrate under reduced pressure. Purify the resulting residue via silica gel chromatography, eluting with a gradient of 10-25% MTBE in hexanes, to give the title compound as a mixture of diastereomers (0.348 g, 79% yield). ES/MS m/z ($^{35}Cl/^{37}Cl$) 484.0/486.0 $[M+H]^+$.

PREPARATION 25

(S)-[(3aR,4R,6R,6aR)-4-(4-Chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol Slowly add a 1.0 M solution of lithium tri-sec-butylborohydride solution in THF (19 mL, 19 mmol) to a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanone (6.5 g, 15 mmol) in THF (200 mL) at −78° C. Stir the mixture at −78° C. for 4 hr under $N_2$ and then quench with saturated aqueous ammonium chloride solution (50 mL). Add EtOAc (200 mL) and separate the organic phase. Extract the aqueous phase with EtOAc (3×70 mL). Combine the organic extracts, wash with water (100 mL), and dry the organic layer over sodium sulfate. Filter and concentrate the filtrate under reduced pressure to give a residue. Purify the resulting residue by silica gel chromatography, eluting with a gradient of 10-30% EtOAc in hexanes, to give the title compound (4.55 g, 70% yield). ES/MS m/z ($^{35}Cl/^{37}Cl$) 436.0/438.0 $[M+H]^+$.

PREPARATION 26

(R)-[(3aR,4R,6R,6aR)-4-(4-Chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol Suspend [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanone (4.77 g, 11.0 mmol) and (R,R)-Ts-DENEB™ (357 mg, 0.549 mmol) in 5:2 formic acid-triethylamine complex (45 mL). Stir the mixture 18 hr at room temperature. Dilute the mixture with water (300 mL) and DCM (75 mL). Separate the layers and extract the aqueous layer with DCM (3×75 mL). Combine the organic extracts and concentrate under reduced pressure. Purify the resulting residue via silica gel chromatography, eluting with a gradient of 30-60% of a 20% mixture of acetone/hexanes in hexanes, to give the title compound, (3.50 g, 73% yield). ES/MS m/z ($^{35}Cl/^{37}Cl$) 436.0/438.0/440.0 $[M+H]^+$.

ALTERNATE PREPARATION 26

Stir a mixture of $[Cp^*IrCl_2]_2$ (8.41 g, 10.45 mmol) and (R,R)-Ts-DEPEN (7.899, 20.91 mmol) in 1.33/1 water/DCM (3972 mL) at 50° C. for 45 min. Cool to room temperature and add ammonium formate (509.7 g, 7840 mmol). Stir the biphasic mixture at room temperature for 5 min and add [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanone (227.0 g, 522.7 mmol). Stir the mixture at room temperature for 1 hr. Separate the resulting organic layer and extract the aqueous layer with DCM (1000 mL). Combine the organic extracts and concentrate under reduced pressure to give an orange solid. Purify the resulting residue by recrystallization from EtOH (3400 mL) to give the title compound, (199.5 g, 86% yield). ES/MS m/z ($^{35}Cl/^{37}Cl$) 436.0/438.0/440.0 $[M+H]^+$.

PREPARATION 27

(R)-[(3aR,4R,6R,6aR)-4-(4-Chloropyrrolo[2,3-d]pyrimidin-7-yl)-2,2-dimethyl-3a,4,6,6a-tetrahydrofuro[3,4-d][1,3]dioxol-6-yl]-[4-chloro-3-(cyclopropoxy)phenyl]methanol Stir a mixture of $[Cp^*IrCl_2]_2$ (1.58 g, 1.95 mmol) and (R,R)-Ts-DEPEN (1.43 g; 3.90 mmol) in 1/1 water/DCM (860 mL) at 40° C. for 45 min Cool to room temperature and add ammonium formate (100 g, 1462 mmol). Stir the biphasic mixture at room temperature for 5 min and add drop wise a solution of [(3aR,4R,6S,6aS)-4-(4-aminopyrrolo[2,3-d]pyrimidin-7-yl)-2,2-dimethyl-3a,4,6,6a-tetrahydrofuro[3,4-d][1,3]dioxol-6-yl]-[4-chloro-3-(cyclopropoxy)phenyl]ethanone (48.8 g, 97.4 mmol) in DCM (100 mL) for 10 min Stir the mixture at room temperature for 1 hr. Separate the resulting organic layer and extract the aqueous layer with DCM (2×200 mL). Combine the organic extracts and wash with water (200 mL). Dry the organic extracts over sodium sulfate, filter, and concentrate the filtrate under reduced pressure. Purify the resulting residue via silica gel chromatography, eluting with a gradient of 5-10% EtOAc in DCM, to give the title compound (35.3 g, 70% yield). ES/MS m/z ($^{35}Cl/^{37}Cl$) 492.0/494.0 $[M+11]^+$. $^1H$ NMR (300 MHz, $d_6$-DMSO) δ 0.59-0.71 (m, 4H) 1.30 (s, 3H), 1.51 (s, 3H), 3.61-3.65 (m, 1H), 4.20-4.22 (m, 1H), 4.68 (t, J=4.9 Hz, 1H), 5.12-5.14 (m, 1H), 5.31-5.34 (m, 1H), 6.09 (d, J=4.7 Hz, 1H), 6.34-6.35 (m, 1H), 6.87-6.80 (m, 2H), 7.11 (s, 1H), 7.29 (d, J=8.1 Hz, 1H), 8.05 (d, J=3.7 Hz, 1H), 8.70 (s, 1H).

PREPARATION 28

[(R)-[(3aR,4R,6R,6aR)-4-(4-Chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methyl] 4-nitrobenzoate Stir a mixture of (S)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol, (10.3 g, 23.7 mmol), 4-nitrobenzoic acid (5.94 g, 35.5 mmol) and triphenylphosphine (9.32 g, 35.5 mmol) in THF (120 mL) at 0° C. under $N_2$. Add DIAD (7.19 g, 35.5 mmol) drop wise to the mixture and stir for 6 hr at room temperature. Add additional 4-nitrobenzoic acid (1.98, 11.8 mmol), triphenylphosphine (3.11 g, 11.8 mmol) and DIAD (2.40 g, 11.8 mmol) at room temperature and stir the mixture for 18 hr at room temperature under $N_2$. Cool the mixture to 0° C. and quench with water (100 mL). Add EtOAc (100 mL) and separate the resulting organic layer. Extract the aqueous layer with EtOAc (3×75 mL). Combine the organic extracts, wash with water (100 mL), and dry over sodium sulfate. Filter and concentrate the filtrate under reduced pressure to give a crude mixture. Purify via silica gel chromatography, eluting with a gradient of 10-15% EtOAc in hexanes, to give the title compound (10.1 g, 73% yield). ES/MS m/z ($^{35}$Cl/$^{37}$Cl) 585.00/587.00 [M+H]$^+$.

PREPARATION 29

Diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-(trifluoromethyl)phenyl]methanol Add a solution of 1.0 M lithium tri-sec-butylborohydride solution in THF (93.5 mL, 93.5 mmol) slowly to a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-[4-(trifluoromethyl)phenyl]methanone (35.0 g, 74.8 mmol) in THF (525 mL) at −78° C. Under a $N_2$ atmosphere, stir the mixture at −78° C. for 30 min and then warm to 0° C. Quench with saturated aqueous ammonium chloride. Add EtOAc and separate the organic phase. Extract the aqueous layer twice with EtOAc. Combine the organic extracts and wash with water and saturated aqueous sodium chloride. Dry the organic layer over sodium sulfate, filter, and concentrate the filtrate under reduced pressure to give a residue. Purify the residue by silica gel chromatography, eluting with a gradient of 0-50% EtOAc in hexanes, to give the title compound (22.0 g, 55% yield). ES/MS m/z ($^{35}$Cl/$^{37}$Cl) 470.00/472.00 [M+H]$^+$.

PREPARATION 30

Diastereomer of [[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-(trifluoromethyl)phenyl]methyl] 4-nitrobenzoate Dissolve diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-(trifluoromethyl)phenyl]methanol (21.0 g, 44.7 mmol), 4-nitrobenzoic acid (14.9 g, 89.4 mmol) and triphenylphosphine (23.45 g, 89.4 mmol) in THF (315 mL) and stir at 0° C. under $N_2$. Add DIAD (18.1 g, 89.4 mmol) drop wise to the mixture and stir for 3 hr at room temperature. Add additional 4-nitrobenzoic acid (7.50 g, 44.7 mmol), triphenylphosphine (11.8 g, 44.7 mmol), and DIAD (9.1 g, 44.7 mmol) at room temperature and stir the mixture for 2 hr at room temperature under $N_2$. Cool the mixture to 0° C., quench with water (100 mL), and dilute with EtOAc (200 mL). Separate the resulting organic layer and extract the aqueous layer with EtOAc (3×75 mL). Combine the organic extracts and wash with water (100 mL) and saturated aqueous sodium chloride. Dry over sodium sulfate, filter, and concentrate the filtrate under reduced pressure to give a residue. Purify the residue via silica gel chromatography, eluting with a gradient of 0-50% EtOAc in hexanes, to give the title compound (18.5 g, 60% yield). ES/MS m/z ($^{35}$Cl/$^{37}$Cl) 619.00/621.00 [M+H]$^+$.

PREPARATION 31

Diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3-chlorophenyl)methanol Slowly add a solution of 1.0 M lithium tri-sec-butylborohydride solution in THF (1.05 mL, 1.05 mmol) to a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(3-chlorophenyl)methanone (0.35 g, 0.81 mmol) in THF (10.7 mL) at −78° C. Stir the mixture at −78° C. for 10 min under $N_2$ and then add 1 N aqueous HCl (1.3 mL). Add EtOAc (50 mL), and wash the organic layer with water (10 mL) followed by saturated aqueous sodium chloride (10 mL). Dry the organic extract over sodium sulfate, filter, and concentrate the filtrate under reduced pressure to give a residue. Purify the residue via silica gel chromatography, eluting with a gradient of 10-30% EtOAc in hexanes, to give the title compound (0.22 g, 61% yield). ES/MS m/z ($^{35}$Cl/$^{37}$Cl) 436.2/438.2 [M+H]$^+$.

PREPARATION 32

Diastereomer of [[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3-chlorophenyl)methyl] 4-nitrobenzoate Stir diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3-chlorophenyl)methanol (0.100 g, 0.229 mmol), 4-nitrobenzoic acid (0.76 g, 0.46 mmol), and triphenylphosphine (0.12 g, 0.46 mmol) in THF (1 mL) at 0° C. under $N_2$. Add DIAD (0.95 g, 0.46 mmol) drop wise to the mixture and stir for 1.5 hr at room temperature. Add additional 4-nitrobenzoic acid (1.98 g, 11.8 mmol), triphenylphosphine (0.015 g, 0.057 mmol), and DIAD (0.012 g, 0.057 mmol) and stir the mixture for 18 hr at room temperature under $N_2$. Cool the mixture to 0° C. Add water (10 mL), EtOAc (10 mL), and separate the resulting organic layer. Extract the aqueous layer with EtOAc (2×10 mL). Combine the organic extracts, wash with water (100 mL), and dry the organic layer over sodium sulfate. Filter and concentrate the filtrate under reduced pressure. Purify the resulting residue via silica gel chromatography, eluting with a gradient of 10-15% EtOAc in hexanes, to give the title compound (0.11 g, 82% yield). ES/MS m/z ($^{35}$Cl/$^{37}$Cl) 585.0/587.0 [M+H]$^+$.

PREPARATION 33

Diastereomer of 4-[[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-hydroxymethyl]benzonitrile Dissolve 4-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxole-6-carbonyl]benzonitrile (1.33 g, 3.14 mmol)

and a 1.0 M solution in toluene of (S)-1-butyl-3,3-diphenylhexahydropyrrolo[1,2-c][1,3,2]oxazaborole (0.31 mL, 0.31 mmol) in THF (50 mL) and cool the mixture to −15° C. Add a 1.0 M solution of borane-THF complex in THF (2.07 mL, 2.07 mmol). Allow the reaction to warm to room temperature and stir the reaction for 17 hr. Cool the reaction mixture to 0° C. and quench by adding MeOH (5 mL). Dilute with saturated aqueous ammonium chloride (40 mL) and EtOAc (80 mL). Separate the layers and extract the aqueous layer with additional EtOAc. Combine the organic extracts, dry over magnesium sulfate, filter, and concentrate the filtrate under reduced pressure. Purify the resulting residue via silica gel chromatography, eluting with a gradient of 25-40% EtOAc in hexanes, to give the title compound (0.75 g, 58% yield). ES/MS m/z ($^{35}$Cl/$^{37}$Cl) 427.0/429.0 [M+H]$^{+}$.

PREPARATION 34

Diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol Dissolve [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanone (490.0 mg, 1.045 mmol) and a 1.0 M solution in toluene of (S)-1-butyl-3,3-diphenylhexahydropyrrolo[1,2-c][1,3,2]oxazaborole (0.10 mL, 0.10 mmol) in THF (20.9 mL) and cool the mixture to −15° C. Add a 1.0 M solution of borane-THF complex in THF (0.69 mL, 0.69 mmol). Allow the reaction to warm to room temperature and stir the reaction for 17 hr. Quench by adding MeOH (1 mL). Dilute with saturated aqueous ammonium chloride (40 mL) and EtOAc (40 mL). Separate the layers and extract the aqueous layer with additional EtOAc (2×40 mL). Combine the organic extracts and wash with saturated aqueous bicarbonate and saturated aqueous sodium chloride. Dry the organic extracts over magnesium sulfate, filter, and concentrate the filtrate under reduced pressure. Purify the resulting residue via silica gel chromatography, eluting with a gradient of 5-25% MTBE in hexanes, to give the title compound (246.8 mg, 50% yield). ES/MS m/z ($^{35}$Cl/$^{37}$Cl) 470/472 [M+H]$^{+}$.

PREPARATION 35

(R)-(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-phenyl-methanol Suspend [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-phenyl-methanone (0.866 g, 2.17 mmol) and (R,R)-Ts-DENEB™ (70.4 mg, 10.8 mmol) in 5:2 formic acid-triethylamine complex (15 mL), and stir for 4 hr at room temperature. Dilute the reaction mixture with water (60 mL). Extract the aqueous layer with DCM. Evaporate the organic extracts under reduced pressure. Purify the resulting residue via silica gel chromatography, eluting with a gradient of 15-30% acetone in hexanes over 20 min, to give the title compound (0.420 g, 48% yield). ES/MS m/z ($^{35}$Cl/$^{37}$Cl) 402.0/404.0 [M+H]$^{+}$.

PREPARATION 36

Diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chloro-2-fluoro-phenyl)methanol Suspend [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chloro-2-fluoro-phenyl)methanone (0.50 g, 1.0 mmol) and (R,R)-Ts-DENEB™ (30 mg, 0.05 mmol) in 5:2 formic acid-triethylamine complex (10 mL) and stir for 1 hr at room temperature. Dilute the reaction mixture with water (50 mL), and extract the aqueous layer with DCM. Dry the organic extracts over sodium sulfate, filter, and concentrate the filtrate under reduced pressure. Purify the resulting residue via silica gel chromatography, eluting with a gradient of 0-40% EtOAc in hexanes, to give the title compound (0.45 g, 95% yield). ES/MS m/z ($^{35}$Cl/$^{37}$Cl) 454.0/456.0/458.0 [M+H]$^{+}$.

PREPARATION 37

Diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3-ethylphenyl)methanol Suspend [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(3-ethylphenyl)methanone (0.975 g, 2.28 mmol) and (R,R)-Ts-DENEB™ (74 mg, 0.11 mmol) in 5:2 formic acid-triethylamine complex (22 mL), and stir 4 hr at room temperature. Dilute the reaction mixture with water (250 mL). Extract the aqueous layer with DCM. Dry the organic extracts over sodium sulfate, filter, and concentrate the filtrate under reduced pressure. Purify the resulting residue via silica gel chromatography, eluting with a gradient of 0-20% EtOAc in hexanes over 30 min, to give the title compound (0.37 g, 38% yield). ES/MS m/z ($^{35}$Cl/$^{37}$Cl) 430.2/432.2 [M+H]$^{+}$.

PREPARATION 38

Diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-difluorophenyl)methanol Add (R,R)-Ts-DENEB™ (93 mg, 0.143 mmol) to a mixture of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-difluorophenyl)methanone (1.12 g, 2.57 mmol) and 5:2 formic acid-triethylamine complex (10 mL) at room temperature. Flush the reaction vessel with $N_2$ and stir the mixture at room temperature for 1.5 hr. Dilute the resulting mixture with water (75 mL) and DCM (25 mL) and mix for 5 min Separate the layers and extract the aqueous layer with DCM. Combine the organic extracts and dry over magnesium sulfate. Filter and concentrate the filtrate under reduced pressure. Purify the resulting residue via silica gel chromatography, eluting with a gradient of 5-10% EtOAc in DCM, to give the title compound as a diastereomer (0.8 g, 69% yield). ES/MS m/z 438 [M+H]$^{+}$.

PREPARATION 39

Diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(p-tolyl) methanol Add 5:2 formic acid-triethylamine complex (4.0 mL) to a mixture of (R,R)-Ts-DENEB™ (31.8 mg, 0.048 mmol) and [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(p-tolyl)methanone (405.0 mg, 0.978 mmol) in 1,4-dioxane (4.0 mL) at room temperature. Stir at room temperature for 4 hr. Dilute with water (15 mL) and extract with EtOAc (3×40 mL). Combine the organic extracts and wash with saturated aqueous bicarbonate and saturated aqueous sodium chloride. Dry the organic layer over magnesium sulfate, filter, and concentrate the filtrate under reduced pressure. Purify the resulting residue via silica gel chromatography, eluting with a gradient of 10-30% MTBE in hexanes, to give the title compound (144 mg, 38% yield). ES/MS m/z ($^{35}Cl/^{37}Cl$) 416/418 $[M+H]^+$.

PREPARATION 40

Diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-fluorophenyl)methanol Add (R,R)-Ts-DENEB™ (242 mg, 0.372 mmol) to a mixture of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-fluorophenyl)methanone (1.41 g, 3.24 mmol) 5:2 formic acid-triethylamine complex (25 mL) and 1,4-dioxane (12 mL) and stir the reaction mixture at room temperature for 2 hr. Dilute the mixture with water (80 mL) and DCM (40 mL) and mix for 5 min. Separate the layers and extract the aqueous layer with additional DCM (2×40 mL). Combine the organic extracts and dry over sodium sulfate, filter, and concentrate the filtrate under reduced pressure. Purify the resulting residue via silica gel chromatography, eluting with a gradient of 4-10% EtOAc in DCM, to give the title compound (1.01 g, 73% yield). ES/MS m/z 420 $[M+H]^+$.

PREPARATION 41

(R)-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-phenyl-methanol Stir a mixture of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-phenyl-methanol (0.399 g, 0.993 mmol) and 7 N $NH_3$ in MeOH (15 mL, 105 mmol) in a sealed reaction vessel. Microwave the mixture at 100° C. for 8 hr. Cool the vessel to room temperature and evaporate the solvent under a stream of $N_2$. Purify the resulting residue via silica gel chromatography, eluting with a gradient of 50-100% of a 10% MeOH/MTBE mixture in hexanes 25 min, to give the title compound (0.295 g, 78% yield). ES/MS m/z 383.2 $[M+H]^+$.

PREPARATION 42

(R)-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol Add (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methyl] 4-nitrobenzoate (10.1 g, 17.3 mmol), ammonium hydroxide (28% in water, 50 mL) and 1,4-dioxane (50 mL) to a sealed vessel and heat at 110° C. for 18 hr. Cool the reaction to 0° C. and add water (50 mL) and EtOAc (100 mL). Separate the resulting organic layer and extract the aqueous layer with EtOAc (3×50 mL). Combine the organic extracts and dry over sodium sulfate. Filter and concentrate the filtrate under reduced pressure to give a residue. Purify the residue by filtration through a silica plug, eluting with an isocratic mixture of hexanes:EtOAc (1:1) to give the title compound (6.78 g, 75% yield) as a brown vitreous solid that is used without further purification.

ALTERNATE PREPARATION 42

Place a 300-mL seamless stainless steel tubular reactor (o.d.=⅛") inside a GC oven. Flush with 3:10 ratio ammonium hydroxide (28% in water)/dioxane at 10 mL/min over 40 min Apply a back pressure of $N_2$ (800 psig) to the outlet of the reaction system and set the temperature of the GC oven at 200° C. Pump a solution of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol (200.0 g, 458.41 mmol) in 3:10 ratio ammonium hydroxide (28% in water)/dioxane (1300 mL) through the reactor at 10 mL/min (30 min residence time) using a high-pressure 1 L Teledyne ISCO™ syringe pump. After consumption of this feed solution, flush the reactor with 3:10 ammonium hydroxide (28% in water):dioxane (600 mL) pumping at 10 mL/min Remove the solvents of the collected solutions under vacuum to ⅓ volume, add water (300 mL) and extract with EtOAc (3×150 mL). Combine the organic extracts, wash with saturated aqueous sodium chloride, dry over sodium sulfate, filter, and evaporate the filtrate under reduced pressure. Purify the resulting residue by trituration from hexane (200 mL) to give the title compound (189.0 g, 95% purity). ES/MS m/z ($^{35}Cl/^{37}Cl$) 416.0/418.0 $[M+H]^+$.

PREPARATION 43

(1R)-1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-(4-chlorophenyl)ethanol Dissolve (1R)-1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(4-chlorophenyl)ethanol (11.4 g, 25.3 mmol) in ammonium hydroxide (28% in water, 60 mL) and 1,4-dioxane (60 mL) in a sealed vessel and heat at 110° C. for 18 hr. Cool to room temperature and remove the solvents under reduced pressure. Add water (50 mL) and EtOAc (100 mL). Separate the resulting organic layer and extract the aqueous layer with EtOAc (3×100 mL). Combine the organic extracts, dry over sodium sulfate, filter, and evaporate the filtrate under reduced pressure to give the title compound (10.7 g, 96% yield) as a brown vitreous solid. ES/MS m/z ($^{35}$Cl/$^{37}$Cl) 431.00/433.20 [M+H]$^+$.

PREPARATION 44

Diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-[4-(trifluoromethyl)phenyl]methanol Dissolve diastereomer of [[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-(trifluoromethyl)phenyl]methyl] 4-nitrobenzoate (21 g, 33.9 mmol) in ammonium hydroxide (28 wt % in water, 100 mL) and 1,4-dioxane (100 mL) in sealed tube, and heat the mixture at 110° C. for 18 hr. Cool the tube to room temperature, collect the precipitated solid by filtration, and wash the filter cake with water. Dissolve the filter cake in EtOAc (300 mL). Wash the resulting organic layer with water and dry over sodium sulfate. Filter and concentrate the filtrate under reduced pressure to give a residue. Purify the residue by filtration through a silica gel plug, eluting with an isocratic mixture of hexanes:EtOAc (1:1) to give the title compound (13.5 g, 80% yield) as a diastereomer as colorless oil. ES/MS m/z 451.2/452.2 [M+H]$^+$.

PREPARATION 45

Diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(3-chlorophenyl)methanol Stir diastereomer of [[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3-chlorophenyl)methyl] 4-nitrobenzoate (0.105 g, 0.18 mmol), 1,4-dioxane (4 mL), and ammonium hydroxide (30 wt % in water, 6 mL) in a sealed reaction vessel. Heat the reaction to 85° C. After 24 hr at 85° C. cool to room temperature, add additional ammonium hydroxide (30 wt % in water, 6 mL), and stir at 95° C. for an additional 24 hr. Cool to room temperature and add water (50 mL). Extract with EtOAc. Combine the organic extracts, dry over sodium sulfate, filter, and concentrate the filtrate under reduced pressure. Purify the resulting residue via silica gel chromatography, eluting with a gradient of 50-100% EtOAc in hexanes, to give the title compound (0.053 g, 71% yield). ES/MS m/z ($^{35}$Cl/$^{37}$Cl) 417.2/419.2 [M+H]$^+$.

PREPARATION 46

Diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-chloro-2-fluoro-phenyl)methanol Stir a mixture of diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chloro-2-fluoro-phenyl)methanol (0.12 mg, 0.26 mmol), 1,4-dioxane (2 mL), and ammonium hydroxide (30 wt % in water, 4 mL) in a sealed reaction vessel. Heat the mixture to 80° C. After 12 hr, cool the tube to room temperature, and add additional ammonium hydroxide (30 wt % in water, 4 mL). Continue heating the sealed vessel at 80° C. for an additional 3 hr. Cool the reaction to room temperature, dilute with water, and extract with DCM (3×25 mL). Combine the organic extracts, dry over sodium sulfate, filter, and evaporate the filtrate under reduced pressure. Purify the resulting residue via silica gel chromatography, eluting with a gradient of 0-50% EtOAc in DCM over 30 min, to give the title compound (0.070 g, 61% yield). ES/MS m/z ($^{35}$Cl/$^{37}$Cl) 435.2/437.2 [M+H]$^+$.

PREPARATION 47

Diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(3-ethylphenyl)methanol Stir a mixture of diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3-ethylphenyl)methanol (0.370 g, 0.861 mmol), 1,4-dioxane (4 mL), and ammonium hydroxide (30 wt % in water, 6 mL) in a sealed reaction vessel. Heat the mixture to 80° C. for 12 hr. Cool the vessel to room temperature, dilute the mixture with water, and extract with EtOAc (3×25 mL). Combine the organic extracts, dry over sodium sulfate, filter, and evaporate the filtrate under reduced pressure. Purify the resulting residue via silica gel chromatography, eluting with a gradient of 0-100% EtOAc in DCM over 30 min, to give the title compound (0.240 g, 68% yield). ES/MS m/z 411.2 [M+H]$^+$.

PREPARATION 48

Diastereomer of 4-[[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-hydroxy-methyl]benzonitrile Dissolve diastereomer of 4-[[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-hydroxy-methyl]benzonitrile (0.765 g, 1.79 mmol) in 1,4-dioxane (4 mL) and ammonium hydroxide (28 wt % in water, 4 mL) in a sealed reaction vessel. Heat the reaction to 85° C. and stir for 18 hr. Cool the reaction to room temperature and concentrate under reduced pressure. Purify the resulting residue via silica gel chromatography, eluting with a gradient of 60-75% of a 9:1 mixture of 10% 7 N $NH_3$ in MeOH/MTBE in hexanes, to give the title compound (0.64 g, 88% yield). ES/MS m/z 408 [M+H]$^+$.

PREPARATION 49

Diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(3,4-difluorophenyl)methanol In a reaction vessel, dissolve diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-difluorophenyl)methanol (795.9 mg, 1.76 mmol) in 1,4-dioxane (4 mL) and add ammonium hydroxide (28 wt % in water, 6 mL). Seal the vessel and heat the mixture to 85° C. with stirring for 18 hr. Cool the vessel to room temperature and concentrate under reduced pressure. Dissolve the resulting solid in a solution of 2% MeOH in DCM and filter the solution through a plug of glass wool. Concentrate the filtrate to give the title compound (694.5 mg, 79% yield). ES/MS m/z 419 [M+H]$^+$.

PREPARATION 50

Diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol Dissolve diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl) methanol (245.0 mg, 0.520 mmol), in ammonium hydroxide (28 wt % in water, 2.0 mL) and 1,4-dioxane (2.0 mL) in a sealed reaction vessel. Heat the vessel to 85° C. and stir for 18 hr. Cool the mixture to room temperature and concentrate under reduced pressure. Purify the resulting residue via silica gel chromatography, eluting with a gradient of 10-50% of a mixture of 10% MeOH/MTBE in hexanes, to give the title compound (184.6 mg, 78% yield). ES/MS m/z ($^{35}$Cl/$^{37}$Cl) 451/453 [M+H]$^+$.

PREPARATION 51

Diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(p-tolyl) methanol Dissolve diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(p-tolyl)methanol (144 mg, 0.346 mmol) in ammonium hydroxide (28 wt % in water, 4.0 mL) and 1,4-dioxane (4.0 mL) in a sealed reaction vessel. Heat the reaction to 85° C. and stir for 18 hr. Cool the reaction to room temperature and concentrate under reduced pressure. Purify the resulting residue via silica gel chromatography, eluting with a gradient of 25-75% of a mixture of 10% MeOH/MTBE in hexanes, to give the title compound (119.4 mg, 87% yield). ES/MS m/z 397 [M+H]$^+$.

PREPARATION 52

Diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-fluorophenyl)methanol Charge two sealed vessels each with diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-fluorophenyl)methanol (505 mg, 1.20 mmol), ammonium hydroxide (28 wt % in water, 15 mL) and 1,4-dioxane (15 mL). Heat the mixtures to 85° C. and stir for 18 hr. Cool the mixtures to room temperature and add ammonium hydroxide (28 wt % in water, 8 mL). Heat both mixtures to 75° C. and stir for 60 hr. Combine the contents of both vessels, and concentrate to dryness under reduced pressure. Dissolve the resulting residue in a solution of 2% MeOH in DCM and filter through a plug of glass wool. Concentrate the filtrate to obtain a residue. Purify the residue via silica gel chromatography, eluting with a gradient of 5% MeOH in DCM, to give the title compound (909.6 mg, 93% yield). ES/MS m/z 401 [M+H]$^+$.

PREPARATION 53

Diastereomer of 1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol Dissolve diastereomer of 1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl) ethanol (150.0 mg, 0.309 mmol), ammonium hydroxide (28 wt % in water, 3.0 mL) and 1,4-dioxane (3.1 mL) in a sealed reaction vessel. Heat the reaction to 85° C. and stir for 18 hr. Cool the reaction to room temperature and concentrate under reduced pressure. Purify the resulting residue via silica gel chromatography, eluting with a gradient of 10-50% of a mixture of 10% MeOH/MTBE in hexanes, to give the title compound (110.9 mg, 77% yield). ES/MS m/z ($^{35}$Cl/$^{37}$Cl) 465/467 [M+H]$^+$.

PREPARATION 54

Diastereomer of 1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-(2-fluorophenyl)ethanol Dissolve diastereomer of 1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(2-fluorophenyl) ethanol (0.48 g, 1.1 mmol) in 1,4-dioxane (6 mL) and ammonium hydroxide (28 wt % in water, 4 mL) in a sealed reaction vessel. Heat the vessel to 85° C. and stir for 22 hr. Cool the mixture to room temperature and concentrate under reduced pressure. Purify the resulting residue via silica gel chromatography, eluting with a gradient of 25-75% of a 9:1 mixture of 10% 7 N $NH_3$ in MeOH/MTBE in hexanes, to give the title compound (0.35 g, 75% yield). ES/MS m/z 415.0 [M+H]$^+$.

PREPARATION 55

Diastereomer of 1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-[2-(trifluoromethyl)phenyl]ethanol Dissolve diastereomer of 1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-[2-(trifluoromethyl) phenyl]ethanol (0.18 g, 0.37 mmol) in 1,4-dioxane (3 mL) and ammonium hydroxide (28 wt % in water, 1 mL) in a sealed reaction vessel. Heat the vessel to 85° C. and stir for 22 hr. Cool the mixture to room temperature and concentrate under reduced pressure. Purify the resulting residue via silica gel chromatography, eluting with a gradient of 50-75% of a 9:1 mixture of 10% 7 N $NH_3$ in MeOH/MTBE in hexanes, to give the title compound (0.14 g, 84% yield). ES/MS m/z 465.0 [M+H]$^+$.

PREPARATION 56

Diastereomer of 1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-[4-(trifluoromethyl)phenyl]ethanol Dissolve 1-[(3aR,4R,6S,6aR)-4-(4-chloropyrrolo[2,3-d] pyrimidin-7-yl)-2,2-dimethyl-3a,4,6,6a-tetrahydrofuro[3,4- d][1,3]dioxol-6-yl]-1-[4-(trifluoromethyl)phenyl]ethanol (0.33 g, 0.68 mmol) in 1,4-dioxane (2 mL) and ammonium hydroxide (28 wt % in water, 3 mL) in a sealed reaction vessel. Heat the vessel to 85° C. and stir the contents for 22 hr. Cool the reaction to room temperature and concentrate under reduced pressure. Purify the resulting residue via silica gel chromatography, eluting with a gradient of 25-75% of a 9:1 mixture of 10% 7 N $NH_3$ in MeOH/MTBE in hexanes, to give the title compound (0.152 g, 48% yield). ES/MS m/z 465.0 $[M+H]^+$.

PREPARATION 57

(R)-[(3aR,4R,6R,6aR)-4-(4-Aminopyrrolo[2,3-d]pyrimidin-7-yl)-2,2-dimethyl-3a,4,6,6a-tetrahydrofuro[3,4-d][1,3]dioxol-6-yl]-[4-chloro-3-(cyclopropoxy)phenyl]methanol Place a 59-mL seamless stainless steel tubular reactor (o.d.=⅛") inside a GC oven. Flush with 1:6 ratio ammonium hydroxide (28% in water)/dioxane at 2.0 mL/min over 40 min Apply a back pressure of $N_2$ (1400-1500 psig) to the outlet of the reaction system and set the temperature of the GC oven at 200° C. Pump a solution of diastereomer of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-chloro-3-(cyclopropoxy)phenyl]methanol (35.3 g, 70.2 mmol) in a ⅙ mixture of ammonium hydroxide (28% in water)/dioxane (350 mL) through the reactor at 0.25 mL/min (30 min residence time) using a high-pressure 1 L Teledyne ISCO™ syringe pump. After consumption of this feed solution, flush the reactor with 1.6 ammonium hydroxide (28% in water):dioxane (89 mL) pumping at 2.0 mL/min Add water (1400 mL) and EtOAc (500 mL). Separate the resulting organic layer and extract the aqueous layer with EtOAc (200 mL). Combine the organic extracts and dry over magnesium sulfate. Filter and concentrate the filtrate under reduced pressure to obtain the title compound (34 g, 88.6% purity). ES/MS m/z ($^{35}Cl/^{37}Cl$) 473.1/475.1 $[M+H]^+$. $^1H$ NMR (300 MHz, $d_6$-DMSO) δ 0.73-0.63 (m, 4H), 1.30 (s, 3H), 1.49 (s, 3H), 4.10 (dd, J=1.6, 6.6 Hz, 1H), 4.66 (dd, J=4.3, 6.4 Hz, 1H), 5.11 (dd, J=1.8, 6.2 Hz, 1H), 5.33 (dd, J=3.3, 6.3 Hz, 1H), 6.12 (d, J=3.3 Hz, 1H), 6.30 (d, J=4.1 Hz, 1H), 6.64 (d, J=3.6 Hz, 1H), 6.86-6.90 (m, 1H), 6.93 (d, J=1.6 Hz, 1H), 7.14 (s, 2H), 7.28 (d, J=8.0 Hz, 1H), 7.39 (d, J=3.6 Hz, 1H), 8.09 (s, 1H).

PREPARATION 58

(1R)-1-[(3aR,4R,6S,6aR)-2,2-Dimethyl-4-(4-methylpyrrolo[2,3-d]pyrimidin-7-yl)-3a,4,6,6a-tetrahydrofuro[3,4-d][1,3]dioxol-6-yl]-1-(4-chlorophenyl)ethanol To a high pressure reaction vessel under $N_2$ atmosphere, add a 2.0 M solution of $Al(CH_3)_3$ in toluene (120 μL, 0.24 mmol) to a stirring mixture of (1R)-1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(4-chlorophenyl)ethanol (0.30 mg, 0.666 mmol), tetrakis (triphenylphosphine)palladium(0) (0.154 g, 0.016 mmol), and dry THF (8 mL). Seal the reaction vessel and heat the mixture to 70° C. After 6 hr at 70° C., cool the vessel to room temperature and carefully add 1 N aqueous HCl (15 mL). Dilute the mixture with water (15 mL) and extract with EtOAc (3×20 mL). Combine the organic extracts; wash with saturated aqueous sodium chloride, dry the organic layer over sodium sulfate, filter, and concentrate the filtrate under reduced pressure. Purify the resulting residue via silica gel chromatography, eluting with an isocratic mixture of 1:1 EtOAc:hexanes, to give the title compound (0.270 g, 89% yield). ES/MS m/z ($^{35}Cl/^{37}Cl$) 430.0/432.0 $[M+H]^+$.

PREPARATION 59

Diastereomer of [(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-(4-chloro-2-fluoro-phenyl)methanol To a high pressure reaction vessel under $N_2$ atmosphere, add a 2.0 M solution of $Al(CH_3)_3$ in toluene (120 μL, 2.4 mmol) to a stirring mixture of diastereomer of [(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chloro-2-fluoro-phenyl)methanol (0.271 mg, 0.597 mmol), tetrakis(triphenylphosphine)palladium(0) (0.138 mg, 0.119 mmol), and dry THF (2.2 mL). Seal the reaction vessel and heat the mixture to 80° C. After 6 hr at 80° C., cool the vessel to room temperature and carefully add 1 N aqueous HCl (10 mL). Dilute with water (15 mL), and extract with EtOAc (3×20 mL). Combine the organic extracts, wash with saturated aqueous sodium chloride, dry over sodium sulfate, filter, and evaporate the filtrate under reduced pressure to give the title compound (0.266 g, 83% yield). ES/MS m/z ($^{35}Cl/^{37}Cl$) 434.2/436.2 $[M+H]^+$.

PREPARATION 60

Diastereomer of 1-[(3aR,4R,6S,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-1-(3,4-dichlorophenyl)ethanol Add a 2.0 M solution of $Al(CH_3)_3$ in toluene (0.57 g, 1.41 mmol) to a mixture of diastereomer of 1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol (171.4 mg, 0.354 mmol), tetrakis (triphenylphosphine)palladium(0) (0.082 g, 0.071 mmol) in 1,4-dioxane (4.4 mL) at room temperature. Heat the mixture at 80° C. for 8 hr. Cool the mixture to room temperature and quench with saturated ammonium chloride (20 mL). Add EtOAc (40 mL) and extract the aqueous layer with EtOAc (4×30 mL). Combine the organic extracts and wash with saturated aqueous bicarbonate and saturated aqueous sodium chloride. Dry the organic extracts over magnesium sulfate, filter, and concentrate the filtrate under reduced pressure. Purify the resulting residue via silica gel chromatography, eluting with a gradient of 25-40% of a 9:1 mixture of 10% 7 N $NH_3$ in MeOH/MTBE in hexanes, to give the title compound (125.9 mg, 77% yield). ES/MS m/z ($^{35}Cl/^{37}Cl$) 451/453 $[M+H]^+$.

PREPARATION 61

(R)-[(3aR,4R,6R,6aR)-2,2-Dimethyl-4-(4-methylpyrrolo[2,3-d]pyrimidin-7-yl)-3a,4,6,6a-tetrahydrofuro[3,4-d][1,3]dioxol-6-yl]-(4-chlorophenyl)methanol To a high pressure reaction vessel under $N_2$ atmosphere, add a 2.0 M solution of $Al(CH_3)_3$ in toluene (120 μL, 0.24 mmol) to a stirring mixture of (R)-[(3aR,4R,6R,6aR)-4-(4- chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol (0.50 g, 1.15 mmol), tetrakis(triphenylphosphine)palladium(0) (0.266 g, 0.230 mmol), and dry THF (13.8 mL). Seal the reaction vessel and heat to 70° C. After 6 hr at 70° C., cool to room temperature and carefully quench with 1 N aqueous HCl (15 mL). Dilute with water (15 mL), and extract with EtOAc (3×20 mL). Combine the organic extracts; wash with saturated aqueous sodium chloride, dry over sodium sulfate, filter, and concentrate the filtrate under reduced pressure. Purify the resulting residue via silica gel chromatography, eluting with an isocratic mixture of 1:1 EtOAc:hexanes, to give the title compound (0.50 g, 95% yield). ES/MS m/z ($^{35}$Cl/$^{37}$Cl) 416.0/418.0 [M+H]$^+$.

EXAMPLE 1

(2R,3R,4S,5R)-2-(4-Aminopyrrolo[2,3-d]pyrimidin-7-yl)-5-[(R)-(4-chlorophenyl)-hydroxy-methyl]tetrahydrofuran-3,4-diol

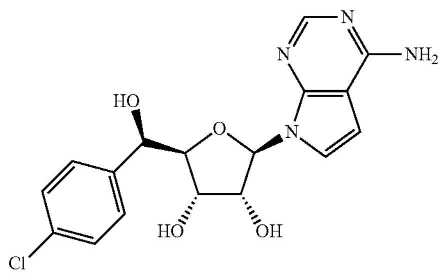 [SMILES: Nc1ncnc2c1ccn2[C@@H]1O[C@H]([C@H](O)c2ccc(Cl)cc2)[C@@H](O)[C@H]1O]

Dissolve (R)-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol, (6.78 g, 13.0 mmol) in TFA (90 mL) at 0° C. Add water (9 mL) and stir the mixture at room temperature for 1 hr. Remove the solvents under reduced pressure and take the residue up in MeOH (25 mL). Cool the mixture to 0° C. and add aqueous ammonium hydroxide (28 wt %) drop wise up to pH-10. Remove the solvent under reduced pressure to give a crude mixture. Purify by silica gel chromatography, eluting with a gradient of 0-2% MeOH in EtOAc, to give a residue. Dissolve the residue in EtOAc (50 mL) and remove the solvents under reduced pressure. Add the resulting light vitreous solid to water (about 50 mL) and stir the mixture overnight at room temperature. Filter the resulting white solid and wash with water (50 mL). Dry the solid to give the title compound (3.24 g, 66% yield). ES/MS m/z ($^{35}$Cl/$^{37}$Cl) 377.05/379.05 [M+H]$^+$. $^1$H NMR (300 MHz, $d_6$-DMSO) δ 4.01 (d, J=4.0 Hz, 2H), 4.63 (dd, J=5.3, 7.5 Hz, 1H), 4.81 (d, J=4.0 Hz, 1H), 5.01 (bs, 1H), 5.20 (bs, 1H), 5.91 (d, J=7.7 Hz, 1H), 6.59 (d, J=3.7 Hz, 1H), 6.69 (bs, 1H), 7.11 (bs, 2H), 7.32-7.45 (m, 5H), 8.05 (s, 1H).

ALTERNATE PREPARATION A EXAMPLE 1, CRYSTALLINE FORM I

Slurry (R)-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol (15.38 g, 0.037 mol) in 2-propanol (50 mL) at 0° C. Add a solution of 4.99 M in 2-propanolHCl (200 mL, 1000 mmol) and water (4 mL) and stir at room temperature for 18 hr. Add additional solution of 4.99 M in 2-propanol HCl (25 mL) and stir the mixture 24 hr at room temperature. Heat the mixture at 40° C. for 2 hr. Concentrate under reduced pressure and add EtOH (50 mL) and water (50 mL) to the resulting residue. Cool to 0° C. and add aqueous $NH_4OH$ (28% yield) drop wise to adjust the pH to ~10 and stir the mixture at room temperature for 2 hr. Concentrate under reduced pressure resulting in a pale yellow solid. Add water (50 mL) drop wise to the yellow solid, followed by the addition of $NH_4OH$ (28%, 2 mL) to adjust the pH to 9, and stir the mixture at room temperature for 3 hr. Collect the resulting precipitate by filtration, rinse the filter cake with water (50 mL), and dry under vacuum for 2 days to give the title compound (13.37 g, 96% yield).

ALTERNATE PREPARATION B, EXAMPLE 1

FLOW CHEMISTRY

Place a 200-mL, PTFE reactor (o.d.=⅛") inside a GC oven. Flush with EtOAc (300 mL). Set the temperature of the GC oven at 55° C. Using a 1 L Teledyne ISCO™ syringe pump, pump a solution of (R)-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol (186.0 g, 01.57 mmol) in 5:2:2 EtOH:MeOH:EtOAc (1674 mL) at 8.5 mL/min and combine in a T-mixer with a stream of 6 N aqueous HCl. Pump the mixture through the reactor at 1.5 mL/min with a peristaltic pump (giving a total residence time of 20 min) After consumption of this feed solution, flush the reactor with a 5:1 mixture EtOAc:6 N aqueous HCl (400 mL) at 10 mL/min Concentrate the collected solution under reduced pressure and cool the resulting aqueous solution to 10° C. in an ice/water bath. Add $NH_4OH$ (28%, 2 mL) drop wise to adjust to pH ~10 and stir the mixture with cooling at 10° C. for 35 hr. Collect the resulting solid, rinse with water (100 mL), and dry under vacuum for 2 days at 35° C., to give the anhydrous title compound (134.5 g; 89% yield).

Obtain the X-ray powder diffraction patterns of crystalline solids on a Bruker D4 Endeavor X-ray powder diffractometer, equipped with a CuKa source (λ=1.54060 Å) and a Vantec detector, operating at 35 kV and 50 mA. Scan the sample between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. Pack the dry powder on a quartz sample holder and obtain a smooth surface using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 35—National Formulary 30 Chapter <941> Characterization of crystalline and partially crystalline solids by X-ray powder diffraction (XRPD) Official Dec. 1, 2012-May 1, 2013. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. Adjust the crystal form diffraction patterns, collected at ambient temperature and relative humidity, based on NIST 675 standard peaks at 8.84 and 26.76 degrees 2-theta.

Crystalline Form 1

Characterize a prepared sample of Alternate Preparation A, Example 1, Form I, by an X-ray diffraction pattern using CuKa radiation as having diffraction peaks (2-theta values) as described in Table 1 below. Specifically the pattern contains a peak at 25.1° in combination with one or more of the peaks selected from the group consisting of 17.1°, 13.6°, 20.5°, 24.0°, and 14.5° with a tolerance for the diffraction angles of 0.2 degrees.

TABLE 1

X-ray powder diffraction peaks of crystalline Example 1, Form 1

| | Angle (° 2θ) | Intensity (% |
|---|---|---|
| 1 | 10.1 | 14 |
| 2 | 13.6 | 52 |
| 3 | 14.5 | 28 |
| 4 | 14.9 | 22 |
| 5 | 15.6 | 21 |
| 6 | 17.0 | 54 |
| 7 | 20.5 | 44 |
| 8 | 20.9 | 13 |
| 9 | 21.5 | 24 |
| 10 | 24.0 | 36 |
| 11 | 24.5 | 12 |
| 12 | 24.8 | 17 |
| 13 | 25.0 | 100 |
| 14 | 25.6 | 13 |
| 15 | 26.5 | 17 |
| 16 | 26.6 | 24 |
| 17 | 28.1 | 11 |
| 18 | 31.5 | 13 |

EXAMPLE 2

(2R,3R,4S,5R)-2-(4-Aminopyrrolo[2,3-d]pyrimidin-7-yl)-5[(R)-hydroxy(phenyl)methyl]tetrahydrofuran-3,4-diol

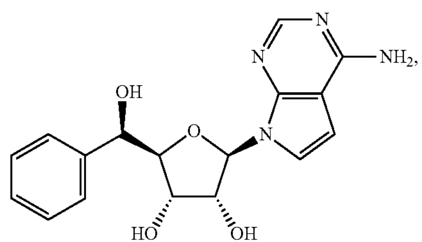 [SMILES: Nc1ncnc2c1ccn2[C@@H]1O[C@H]([C@H](O)c2ccccc2)[C@@H](O)[C@H]1O]

Stir a solution of (R)-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-phenyl-methanol (0.293 g, 0.766 mmol), 4 N HCl in 1,4-dioxane (9.6 mL), and water (3 drops) at room temperature. After 45 min at room temperature, concentrate the solution under reduced pressure. Purify the resulting residue via silica gel chromatography, eluting with a gradient of 50-100% acetone in hexanes over 25 min, to give the title compound (0.195 g, 74% yield). ES/MS m/z 343.0 $[M+H]^+$. $^1H$ NMR (400 MHz, $d_6$-DMSO) δ 4.04-4.06 (m, 2H), 4.55-4.67 (m, 1H), 4.81 (t, J=3.5 Hz, 1H), 4.95 (d, J=3.9 Hz, 1H), 5.19 (d, J=7.1 Hz, 1H), 5.92 (d, J=7.9 Hz, 1H), 6.60 (t, J=3.4 Hz, 2H), 7.11-7.13 (m, 2H), 7.24 (t, J=7.2 Hz, 1H), 7.32-7.35 (m, 3H), 7.42 (d, J=7.3 Hz, 2H), 8.06 (s, 1H).

EXAMPLE 3

(2R,3R,4S,5S)-2-(4-Aminopyrrolo[2,3-d]pyrimidin-7-yl)-5-[(1R)-1-(4-chlorophenyl)-1-hydroxy-ethyl]tetrahydrofuran-3,4-diol

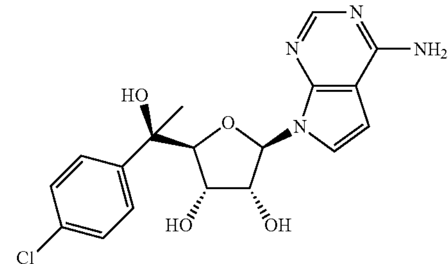 [SMILES: C[C@@](O)(c1ccc(Cl)cc1)[C@H]1O[C@@H](n2ccc3c(N)ncnc32)[C@H](O)[C@@H]1O]

Dissolve (1R)-1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-(4-chlorophenyl)ethanol (10.3 g, 23.9 mmol) in 2-propanol (100 mL) and stir at 0° C. Add a 4.99 M solution of HCl in 2-propanol (200 mL, 1000 mmol) and water (2 mL) drop wise and stir the mixture at room temperature for 6 hr. Remove the solvents under reduced pressure to give a residue. Dissolve the residue in EtOH (50 mL), cool the mixture to 0° C., and add aqueous ammonium hydroxide (28 wt % yield) drop wise up to pH ~10. Concentrate under reduced pressure to give a white vitreous solid. Add the solid to water (about 40 mL) and stir the mixture for 4 hr at room temperature. Filter and collect the resulting white solid, wash with water (50 mL) and air-dry to give the title compound (9.0 g, 96% yield). ES/MS m/z ($^{35}Cl/^{37}Cl$) 391.10/393.10 $[M+H]^+$. $^1H$ NMR (300 MHz, $d_6$-DMSO) δ 1.40 (s, 3H), 3.65-3.67 (m, 1H), 4.13 (s, 1H), 4.61-4.68 (m, 1H), 4.78 (d, J=3.7 Hz, 1H), 5.12 (d, J=7.0 Hz, 1H), 5.81 (d, J=8.1 Hz, 1H), 6.59 (d, J=3.7 Hz, 1H), 7.10 (bs, 1H), 7.19 (bs, 2H), 7.32 (d, J=3.3 Hz, 1H), 7.40 (d, J=8.8 Hz, 2H), 7.58 (d, J=8.8 Hz, 2H), 8.07 (s, 1H).

EXAMPLE 4

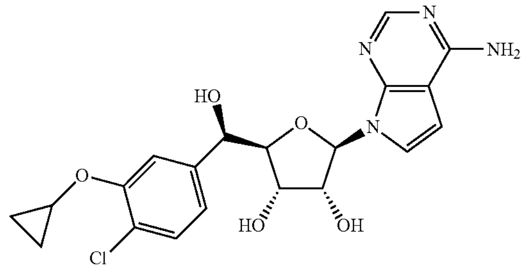 [SMILES: Nc1ncnc2c1ccn2[C@@H]1O[C@H]([C@H](O)c2ccc(Cl)c(OC3CC3)c2)[C@@H](O)[C@H]1O]

Diastereomer of (2R,3R,4S,5R)-2-(4-aminopyrrolo[2,3-d]pyrimidin-7-yl)-5-[(R)-[4-chloro-3-(cyclopropoxy)phenyl]-hydroxy-methyl]tetrahydrofuran-3,4-diol Place a 15-mL teflon coated SS reactor (o.d.=⅛") in a Vapourtec E-series equipment. Apply a back pressure regulator (4-5 bar) to the outlet of the reaction system and set the temperature and set the temperature at 82° C. Pump a solution of diastereomer of (R)-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-[4-chloro-3-(cyclopropoxy)phenyl]methanol (32.1 g, 60.1 mmol) in EtOH (317 mL) at 1.1 mL/min and combine this solution in a T-mixer with a stream of 4 N aqueous HCl solution and pump this mixture at 0.288 mL/min through the reactor (giving a total residence time of 10 min) at 82° C. After consumption of this feed solution, flush the reactor with a mixture EtOH/4 N aqueous HCl (400 mL) at 0.29 mL/min Treat the crude reaction mixture with activated carbon, Darco KB® (100 mesh; wet powder. 13 g) and filter through a short pad of diatomaceous earth. Repeat the treatment with activated carbon, Darco KB® (100 mesh; wet powder, 26 g) and filter through diatomaceous earth. Reduce the organic solvents of the collected solutions under vacuum up to ¼ volume, add water (150 mL) and aqueous $NH_4OH$ (28%, 40 mL) drop wise to adjust the pH to ~10, and extract with EtOAc (2×300 mL). Combine the organic extracts, wash with saturated aqueous sodium chloride, dry over magnesium sulfate, filter, and concentrate the filtrate under reduced pressure to give a residue (17 g). Additionally, rinse both diatomaceous earth pads with MeOH (1000 mL) and remove the organic filtrate washes under reduced pressure to afford additional residue (7.89 g). Combine both residues in 1:10 MeOH:EtOAc (300 mL) and evaporate the solvent under reduced pressure to give the title compound (17.45 g; 67% yield). ES/MS m/z ($^{35}Cl/^{37}Cl$) 433.0/435.0 $[M+H]^+$. $^1H$ NMR (300 MHz, $d_6$-DMSO) δ 0.73-0.81 (m, 4H), 3.77-3.83 (m, 1H), 4.00 (d, J=4.6 Hz, 1H), 4.04-4.09 (m, 1H), 4.67-4.73 (m, 1H), 4.81 (t, J=4.0 Hz, 1H), 5.04 (d, J=3.8 Hz, 1H), 5.21 (d, J=7.3 Hz, 1H), 5.91 (d, J=7.9 Hz, 1H), 6.58 (d, J=3.6 Hz, 1H), 6.65 (d, J=3.4 Hz, 1H), 7.01 (dd, J=1.5, 8.2 Hz, 1H), 7.10 (bs, 2H), 7.35 (d, J=1.6 Hz, 1H), 7.43 (d, J=1.4 Hz, 1H), 8.06 (s, 1H).

EXAMPLE 5

Diastereomer of (2R,3R,4S,5R)-2-(4-aminopyrrolo[2,3-d]pyrimidin-7-yl)-5-[hydroxy-[4-(trifluoromethyl)phenyl]methyl]tetrahydrofuran-3,4-diol

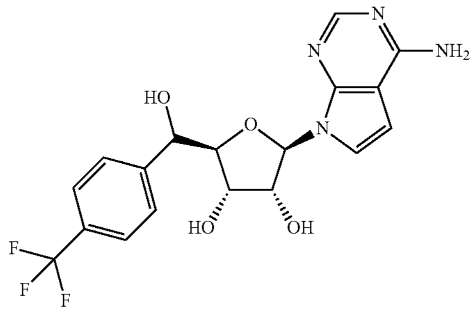 [SMILES: Nc1ncnc2c1ccn2[C@@H]1O[C@H](C(O)c2ccc(C(F)(F)F)cc2)[C@@H](O)[C@H]1O]

Dissolve diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-[4-(trifluoromethyl)phenyl]methanol (13.5 g, 27.0 mmol) in 2-propanol (50 mL) and stir at 0° C. Add a 4.99 M solution of HCl in 2-propanol (200 mL, 0.998 mol) and water (2 mL) drop wise to the mixture and stir at room temperature for 3 hr. Remove the solvent under reduced pressure to give a residue. Dissolve the residue in EtOH (50 mL) and cool the mixture to 0° C. Add aqueous ammonium hydroxide (28 wt %) drop wise u to pH ~10 and stir the mixture for 10 min Remove the solvent under reduced pressure to give a white vitreous solid. Purify by silica gel chromatography, eluting with a gradient of 80-100% EtOAc in hexanes, to give a foam. Suspend the foam in water (300 mL) and stir the mixture for 1 hr at room temperature. Filter the resulting white solid, wash the filter cake with water (50 mL), and dry to give the title compound (7.85 g, 71% yield) as a diastereomer. ES/MS m/z 411.10 $[M+H]^+$. $^1H$ NMR (300 MHz, $d_6$-DMSO) δ 4.02-4.07 (m, 2H), 4.65 (td, J=7.4, 5.1 Hz, 1H), 4.92 (t, J=3.6 Hz, 1H), 5.02 (d, J=3.8 Hz, 1H), 5.22 (d, J=7.1 Hz, 1H), 5.92 (d, J=8.0 Hz, 1H), 6.60 (d, J=3.6 Hz, 1H), 6.81 (d, J=3.3 Hz, H), 7.11 (s, 2H), 7.32 (d, J=3.8 Hz, 1H), 7.71-7.63 (m, 4H), 8.06 (s, 1H).

EXAMPLE 6

Diastereomer of (2R,3R,4S,5R)-2-(4-aminopyrrolo[2,3-d]pyrimidin-7-yl)-5-[(3-chlorophenyl)-hydroxymethyl]tetrahydrofuran-3,4-diol

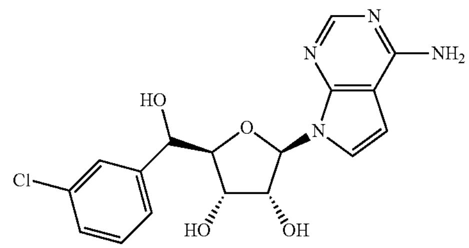 [SMILES: Nc1ncnc2c1ccn2[C@@H]1O[C@H](C(O)c2cccc(Cl)c2)[C@@H](O)[C@H]1O]

Mix diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(3-chlorophenyl)methanol (0.052 g, 0.124 mmol), 4 N HCl in 1,4-dioxane (5 mL) and MeOH (5 mL). Stir the mixture at room temperature. After 1 hr at room temperature, concentrate the solution under a stream of $N_2$ to remove the solvent. Dissolve in water (5 mL) and extract with EtOAc (2 mL). Add 1 N aqueous NaOH until solution is basic, and extract with DCM (4×3 mL). Combine the organic extracts, dry over sodium sulfate, filter, and concentrate the filtrate under reduced pressure. Purify via silica gel chromatography, eluting with a gradient of 50-100% EtOAc in hexanes, to give the title compound as a diastereomer (0.023 g, 49% yield). ES/MS m/z ($^{35}Cl/^{37}Cl$) 377.0/379.0 $[M+11]^+$. $^1H$ NMR (400 MHz, $d_6$-DMSO) δ 3.37 (bs, 1H), 4.04-4.08 (m, 2H), 4.63-4.69 (m, 1H), 4.85-4.88 (m, 1H), 5.07 (d, J=3.6 Hz, 1H), 5.26 (d, J=7.0 Hz, 1H), 5.96 (d, J=8.1 Hz, 1H), 6.64 (d, J=3.5 Hz, 1H), 6.76-6.74 (m, 1H), 7.15-7.18 (bs, 1H), 7.33-7.42 (m, 4H), 7.50-7.52 (m, 1H), 8.09 (s, 1H).

EXAMPLE 7

Diastereomer of (2R,3R,4S,5R)-2-(4-aminopyrrolo[2,3-d]pyrimidin-7-yl)-5-[(4-chloro-2-fluoro-phenyl)-hydroxy-methyl]tetrahydrofuran-3,4-diol hydrochloride

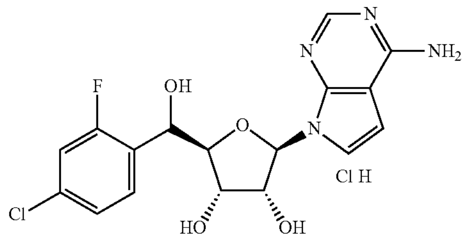

Stir a solution of diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-chloro-2-fluoro-phenyl)methanol (0.067 g, 0.154 mmol), 4 N HCl in 1,4-dioxane (5.0 mL), and MeOH (5.0 mL) at room temperature. After 1 hr at room temperature, concentrate the solution under a stream of $N_2$ to remove the solvent. Triturate the resulting residue with ACN to give the title compound as a diastereomer (0.046 g, 69% yield). ES/MS m/z ($^{35}Cl/^{37}Cl$) 395/397 $[M+H]^+$. $^1H$ NMR (400 MHz, $d_6$-DMSO) δ 3.97-4.00 (m, 1H), 4.09-4.11 (m, 1H), 4.44-4.49 (m, 1H), 4.92-4.96 (m, 1H), 6.06-6.09 (m, 1H), 6.98-7.00 (m, 1H), 7.26-7.28 (m, 1H), 7.32-7.35 (m, 1H), 7.51-7.56 (m, 1H), 7.65-7.66 (m, 1H), 8.35 (s, 1H),

EXAMPLE 8

Diastereomer of (2R,3R,4S,5R)-2-(4-aminopyrrolo[2,3-d]pyrimidin-7-yl)-5-[(2-fluorophenyl)-hydroxy-methyl]tetrahydrofuran-3,4-diol

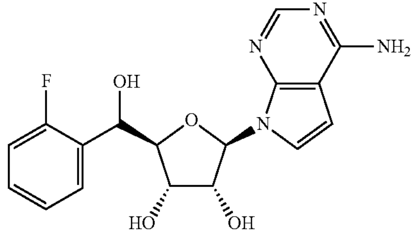 [SMILES: Nc1ncnc2c1ccn2[C@@H]1O[C@H](C(O)c2ccccc2F)[C@@H](O)[C@H]1O]

In a par vessel, evacuate a mixture of diastereomer of (2R,3R,4S,5R)-2-(4-aminopyrrolo[2,3-d]pyrimidin-7-yl)-5-[(4-chloro-2-fluoro-phenyl)-hydroxy-methyl]tetrahydrofuran-3,4-diol hydrochloride (0.036 g, 0.083 mmol), 10% Pd/C (0.010 mg, 0.009 mmol) and EtOH (2.0 mL) under reduced pressure. Charge the vessel with hydrogen gas to 10 psi. After stirring for 24 hr at 10 psi, add triethylamine (0.25 mg, 0.25 mmol) and additional 10% Pd/C (0.010 mg, 0.009 mmol). Evacuate the vessel, and charge to 10 psi with hydrogen. Stir at room temperature for an additional 24 hr. Filter the resulting mixture through diatomaceous earth, and concentrate under reduced pressure. Purify the resulting residue via reverse phase high pressure chromatography (PHENOMENEX® GEMINI®-NX) eluting with a gradient of 5-45% ACN in a mixture of 5% MeOH/10 mM ammonium bicarbonate, pH ~10, over 20 min, to give the title compound as a diastereomer (0.010 g, 33% yield). ES/MS m/z 361 $[M+H]^+$. $^1H$ NMR (400 MHz, $d_6$-DMSO) δ 4.01-4.03 (m, 2H), 4.63-4.64 (m, 1H), 4.97-5.01 (m, 1H), 5.19-5.21 (m, 1H), 5.89-5.93 (m, 1H), 6.56-6.57 (m, 1H), 6.85-6.89 (m, 1H), 7.31-7.32 (m, 5H), 7.60-7.61 (m, 1H), 8.02 (s, 1H).

EXAMPLE 9

Diastereomer of ((2R,3R,4S,5R)-2-(4-aminopyrrolo[2,3-d]pyrimidin-7-yl)-5-[(3-ethylphenyl)-hydroxy-methyl]tetrahydrofuran-3,4-diol hydrochloride

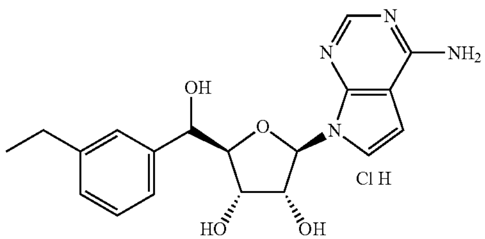

Stir a solution of diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(3-ethylphenyl)methanol (0.240 g, 0.585 mmol), 4 N HCl in 1,4-dioxane (5.0 mL), and MeOH (5.0 mL) at room temperature. After 1 hr at room temperature, concentrate the solution under a stream of $N_2$ to remove the solvent. Triturate the resulting residue with ACN to give the title compound as a diastereomer (0.160 g, 67% yield). ES/MS m/z 371 $[M+H]^+$. $^1H$ NMR (400 MHz, $d_6$-DMSO) δ 1.12 (t, J=7.6 Hz, 3H), 2.51-2.57 (q, J=7.6 Hz, 2H), 3.98-4.02 (m, 1H), 4.08-4.11 (m, 1H), 4.546-4.50 (m, 1H), 4.69-4.72 (m, 1H), 6.06 (d, J=7.7 Hz, 1H), 6.97 (d, J=3.7 Hz, 1H), 7.01-7.06 (m, 1H), 7.14-7.27 (m, 4H), 7.68 (d, J=3.6 Hz, 1H), 8.35 (s, 1H).

EXAMPLE 10

Diastereomer of 4-[[(2R,3S,4R,5R)-5-(4-aminopyrrolo[2,3-d]pyrimidin-7-yl)-3,4-dihydroxy-tetrahydrofuran-2-yl]-hydroxy-methyl]benzonitrile

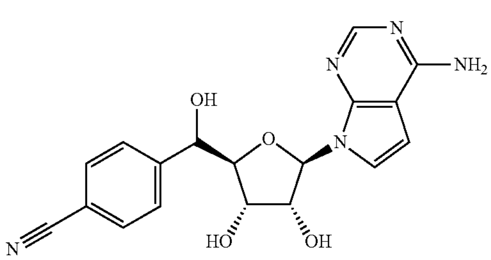 [SMILES: N#Cc1ccc(C(O)[C@H]2O[C@@H](n3ccc4c(N)ncnc43)[C@H](O)[C@@H]2O)cc1]

Mix TFA (3.5 mL) and water (0.5 mL) and cool to 0° C. Add this to diastereomer of 4-[[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-hydroxy-methyl]benzonitrile (0.50 g, 1.24 mmol) and stir at 0° C. After 1 hr, concentrate under reduced pressure and dissolve the resulting solid in MeOH. Elute through a SILICYCLE® Si-Carbonate column (70 mL, 5 g) using MeOH. Collect the appropriate fractions to give the title compound as a diastereomer (0.47 g, 100% yield). ES/MS m/z 368 $[M+H]^+$. $^1H$ NMR (400 MHz, $d_6$-DMSO) δ 3.33-3.41 (m, 2H), 4.04 (d, J=4.2 Hz, 2H), 4.61-4.65 (m, 1H), 4.91 (d, J=4.3 Hz, 1H), 5.06 (d, J=2.4 Hz, 1H), 5.22-5.26 (m, 1H), 5.94 (d, J=7.8 Hz, 1H), 6.65 (d, J=3.6 Hz, 1H), 6.71-6.79 (m, 1H), 7.31-7.35 (m, 2H), 7.39 (d, J=3.6 Hz, 1H), 7.62 (d, J=8.3 Hz, 2H), 7.80 (d, J=8.3 Hz, 2H), 8.10 (s, 1H).

EXAMPLE 11

Diastereomer of (2R,3R,4S,5R)-2-(4-aminopyrrolo[2,3-d]pyrimidin-7-yl)-5-[(3,4-difluorophenyl)-hydroxy-methyl]tetrahydrofuran-3,4-diol

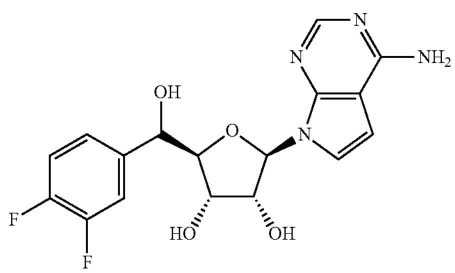 [SMILES: Nc1ncnc2c1ccn2[C@@H]1O[C@H](C(O)c2ccc(F)c(F)c2)[C@@H](O)[C@H]1O]

Mix diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(3,4-difluorophenyl)methanol (694 mg, 1.66 mmol), 1,4-dioxane (6 mL), water (2 mL), 4 M HCl in 1,4-dioxane (3 mL, 12 mmol) at 0° C. Stir the mixture for 18 hr and then add additional 4 M HCl in 1,4-dioxane (4 mL, 16 mmol). Stir the mixture for another 18 hr at room temperature. Add HCl (31 wt % in water, 0.5 mL). Stir the mixture for 4 hr at room temperature. Cool the mixture at 0° C., and slowly add saturated $NaHCO_3$ solution until pH ~7 is achieved. Extract with 2-4% MeOH in DCM. Dry the organic extracts over magnesium sulfate, filter, and concentrate the filtrate under reduced pressure to give a crude residue. Purify the residue via silica gel chromatography, eluting with an isocratic mixture of 77% DCM, 15% EtOAc, and 7% MeOH to give the title compound as a diastereomer (408 mg, 64% yield). ES/MS m/z 379 $[M+H]^+$. $^1H$ NMR (400 MHz, $d_6$-DMSO) δ 4.02-4.04 (m, 2H), 4.63 (td, J=7.3, 5.2 Hz, 1H), 4.82 (t, J=3.9 Hz, 1H), 5.03 (d, J=4.0 Hz, 1H), 5.22 (d, J=7.1 Hz, 1H), 5.92 (d, J=7.8 Hz, 1H), 6.61 (d, J=3.6 Hz, 1H), 6.73 (d, J=3.6 Hz, 1H), 7.11 (s, 2H), 7.27 (dd, J=4.0, 8.2 Hz, 1H), 7.34 (d, J=3.6 Hz, 1H), 7.39-7.46 (m, 2H), 8.06 (s, 1H).

EXAMPLE 12

Diastereomer of (2R,3R,4S,5R)-2-(4-aminopyrrolo[2,3-d]pyrimidin-7-yl)-5-[(3,4-dichlorophenyl)-hydroxy-methyl]tetrahydrofuran-3,4-diol

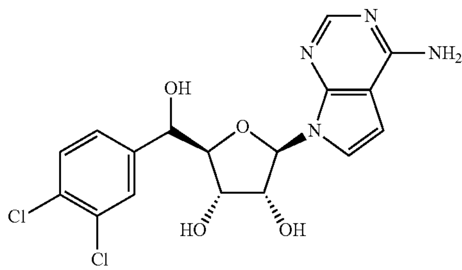 [SMILES: Nc1ncnc2c1ccn2[C@@H]1O[C@H](C(O)c2ccc(Cl)c(Cl)c2)[C@@H](O)[C@H]1O]

Mix diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol (180.0 mg, 0.398 mmol), water (0.20 mL) and TFA (2.0 mL) at room temperature. After 45 min, concentrate the mixture under reduced pressure and dissolve the resulting residue in MeOH. Elute the mixture through a SILICYCLE® Si-Carbonate column (70 mL, 5 g) using MeOH. Collect the appropriate fractions and concentrate in vacuo to give a crude residue. Purify the residue via silica gel chromatography, eluting with a gradient of a mixture of 10% $NH_3$/MeOH in $CHCl_3$ to give the title compound as a diastereomer (98.3 mg, 60% yield). ES/MS m/z ($^{35}Cl/^{37}Cl$) 411/413 $[M+H]^+$. $^1H$ NMR (400 MHz, $d_6$-DMSO) δ 4.01-4.03 (m, 2H), 4.62 (td, J=7.3, 5.0 Hz, 1H), 4.84 (t, J=4.0 Hz, 1H), 5.05 (d, J=3.9 Hz, 1H), 5.22 (d, J=7.1 Hz, 1H), 5.92 (d, J=7.8 Hz, 1H), 6.60 (d, J=3.6 Hz, 1H), 6.77 (d, J=3.6 Hz, 1H), 7.11 (s, 2H), 7.34 (d, J=3.6 Hz, 1H), 7.41 (dd, J=1.8, 8.4 Hz, 1H), 7.59 (d, J=8.3 Hz, 1H), 7.65 (d, J=1.8 Hz, 1H), 8.06 (s, 1H).

EXAMPLE 13

Diastereomer of (2R,3R,4S,5R)-2-(4-aminopyrrolo[2,3-d]pyrimidin-7-yl)-5-[hydroxy(p-tolyl)methyl]tetrahydrofuran-3,4-diol

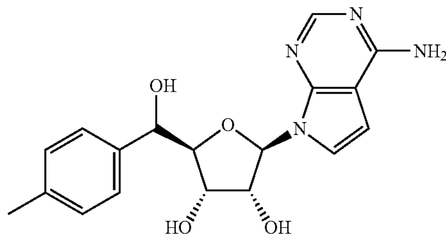 [SMILES: Cc1ccc(C(O)[C@H]2O[C@@H](n3ccc4c(N)ncnc43)[C@H](O)[C@@H]2O)cc1]

Mix diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(p-tolyl)methanol (115 mg, 0.290 mmol), water (0.15 mL) and TFA (1.5 mL) at room temperature. After 90 min, concentrate under reduced pressure and dissolve the resulting solid in MeOH. Elute through a SILICYCLE® Si-Carbonate column (70 mL, 5 g) using MeOH. Collect the appropriate fractions and evaporate to dryness under reduced pressure to give a residue. Purify the residue via silica gel chromatography, eluting with a gradient of 5-15% of a mixture of 10% 7 N $NH_3$/MeOH in DCMs to give the title compound as a diastereomer (50.2 mg, 49% yield). ES/MS m/z 357 $[M+H]^+$. $^1H$ NMR (400 MHz, $d_6$-DMSO) δ 2.29 (s, H), 4.62-4.67 (m, 1H), 4.77 (t, J=3.3 Hz, 1H), 4.93 (d, J=3.8 Hz, 1H), 5.18 (d, J=7.1 Hz, 1H), 5.90 (d, J=7.9 Hz, 1H), 6.58 (dd, J=3.4, 12.3 Hz, 2H), 7.11-7.15 (m, 3H), 7.29-7.33 (m, 3H), 8.06 (s, 1H).

EXAMPLE 14

Diastereomer of (2R,3R,4S,5R)-2-(4-aminopyrrolo[2,3-d]pyrimidin-7-yl)-5-[(4-fluorophenyl)-hydroxy-methyl]tetrahydrofuran-3,4-diol

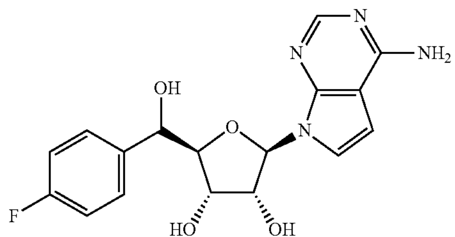 [SMILES: Nc1ncnc2c1ccn2[C@@H]1O[C@H](C(O)c2ccc(F)cc2)[C@@H](O)[C@H]1O]

Mix diastereomer of [(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-(4-fluorophenyl)methanol (158 mg, 0.394 mmol), 1,4-dioxane (3 mL), water (0.75 mL) and a 4 M solution of HCl in 1,4-dioxane (3 mL, 12 mmol) and stir the mixture at 0° C. for 5 min, then at room temperature for 1 hr. Concentrate under reduced pressure, then add EtOAc (30 mL) and concentrate again. Repeat this procedure of adding EtOAc and concentrating twice more. Purify the resulting residue via silica gel chromatography, eluting with an isocratic mixture of 7% MeOH in DCM to give the title compound as a diastereomer (103.5 mg, 73% yield). ES/MS m/z 361 $[M+H]^+$. $^1H$ NMR (400 MHz, $d_6$-DMSO) δ 4.03 (dd, J=4.3, 10.6 Hz, 2H), 4.63 (td, J=7.3, 5.2 Hz, 1H), 4.81 (t, J=3.7 Hz, 1H), 4.99 (d, J=3.9 Hz, 1H), 5.20 (d, J=7.1 Hz, 1H), 5.92 (d, J=7.8 Hz, 1H), 6.61 (dd, J=3.6, 9.5 Hz, 2H), 7.11-7.17 (m, 4H), 7.32 (d, J=3.6 Hz, 1H), 7.45 (dd, J=5.8, 8.5 Hz, 2H), 8.06 (s, 1H).

EXAMPLE 15

Diastereomer of (2R,3R,4S,5S)-2-(4-aminopyrrolo[2,3-d]pyrimidin-7-yl)-5-[1-(4-chlorophenyl)-1-hydroxy-propyl]tetrahydrofuran-3,4-diol

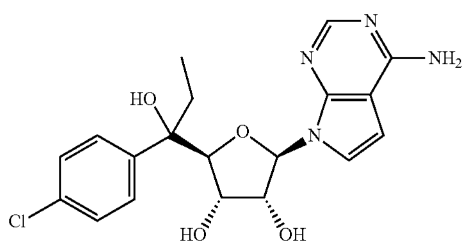 [SMILES: CCC(O)(c1ccc(Cl)cc1)[C@H]1O[C@@H](n2ccc3c(N)ncnc32)[C@H](O)[C@@H]1O]

Dissolve diastereomer of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanone (426.9 mg, 0.983 mmol) in THF (5 mL) and cool the mixture to 0° C. Add a 1.0 M solution of ethylmagnesium bromide in THF (1.97 mL, 1.97 mmol) over 1 min Stir for 15 min and warm to room temperature. After 1 hr, quench by adding 1 N aqueous HCl (2.48 mL). Dilute the reaction mixture with DCM (10 mL). Separate the layers and extract the aqueous layer with DCM (5 mL). Combine the organic extracts and evaporate under reduced pressure. Dissolve the residue in 7 M $NH_3$/MeOH (10 mL, 70 mmol) and heat in a microwave reactor at 100° C. for 6 hr. Evaporate the resulting mixture under a $N_2$ stream at 50° C. Dissolve the resulting residue in 4 N HCl in 1,4-dioxane (1.29 mL, 49.2 mmol) and add water (35 μL, 1.97 mmol). Stir the mixture at room temperature for 1.5 hr, and then concentrate the mixture under reduced pressure. Purify the resulting residue via reverse phase high pressure liquid chromatography (PHENOMENEX® GEMINI®-NX) eluting with a gradient of 13-48% ACN in a mixture of 5% MeOH/10 mM ammonium bicarbonate, pH ~10, to give the title compound as a diastereomer (97.8 mg, 25% yield). ES/MS m/z ($^{35}Cl/^{37}Cl$) 405.1/407.2 $[M+H]^+$. $^1H$ NMR (400 MHz, $d_6$-DMSO) δ 0.54 (t, J=7.4 Hz, 3H), 1.75-1.92 (m, 2H), 3.63 (d, J=5.0 Hz, 1H), 4.22 (s, 1H), 4.69 (dd, J=5.3, 7.6 Hz, 1H), 4.78-4.82 (m, 1H), 5.14-5.20 (m, 1H), 5.75 (d, J=8.1 Hz, 1H), 6.59 (d, J=3.5 Hz, 1H), 7.11 (s, 1H), 7.23 (s, 1H), 7.31 (d, J=3.6 Hz, 1H), 7.42 (d, J=8.7 Hz, 2H), 7.53-7.56 (m, 2H), 8.08 (s, 1H).

EXAMPLE 16

Diastereomer of (2R,3R,4S,5S)-2-(4-aminopyrrolo[2,3-d]pyrimidin-7-yl)-5-[1-(3,4-dichlorophenyl)-1-hydroxy-ethyl]tetrahydrofuran-3,4-diol

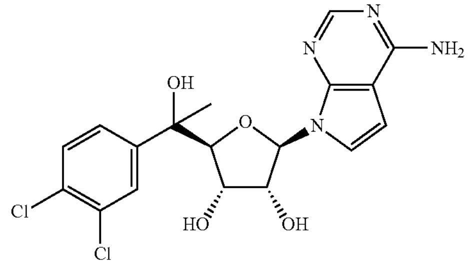 [SMILES: CC(O)(c1ccc(Cl)c(Cl)c1)[C@H]1O[C@@H](n2ccc3c(N)ncnc32)[C@H](O)[C@@H]1O]

Combine diastereomer of 1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol (101.2 mg, 0.217 mmol), water (0.1 mL) and TFA (1.0 mL) at room temperature. After stirring 1 hr, concentrate under reduced pressure and dissolve the resulting solid in MeOH. Elute through a SILICYCLE® Si-Carbonate column (70 mL, 5 g) using MeOH. Collect the appropriate fractions to give a residue. Purify the resulting residue via silica gel chromatography, eluting with a gradient pf 5-30% of a mixture of 10% 7 N $NH_3$ in MeOH/MeOH/chloroform (1:1:2, by volume) in $CHCl_3$ to give the title compound as a diastereomer (81.7 mg, 88% yield). ES/MS m/z ($^{35}Cl/^{37}Cl$) 426/428 $[M+H]^+$. $^1H$ NMR (400 MHz, $d_6$-DMSO) δ 1.42 (s, 3H), 3.66 (t, J=4.4 Hz, 1H), 4.15 (s, 1H), 4.56-4.65 (m, 1H), 4.85 (d, J=3.7 Hz, 1H), 5.14 (d, J=7.2 Hz, 1H), 5.83 (d, J=8.0 Hz, 1H), 6.61 (d, J=3.6 Hz, 1H), 7.20 (s, 2H), 7.27

(s, 1H), 7.33 (d, J=3.5 Hz, 1H), 7.55 (dd, J=2.0, 8.5 Hz, 1H), 7.62 (d, J=8.5 Hz, 1H), 7.81 (d, J=2.0 Hz, 1H), 8.08 (s, 1H).

EXAMPLE 17

Diastereomer of (2R,3R,4S,5S)-2-(4-aminopyrrolo[2,3-d]pyrimidin-7-yl)-5-[1-(2-fluorophenyl)-1-hydroxy-ethyl]tetrahydrofuran-3,4-diol

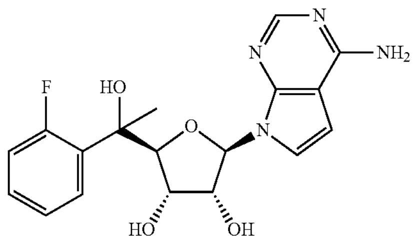 [SMILES: CC(O)(c1ccccc1F)[C@H]1O[C@@H](n2ccc3c(N)ncnc32)[C@H](O)[C@@H]1O]

Mix TFA (4 mL) and water (1 mL) and cool to 0° C. Add this to diastereomer of 1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-(2-fluorophenyl)ethanol (0.341 g, 0.823 mmol) and stir at 0° C. After 30 min, concentrate under reduced pressure and dissolve the resulting solid in MeOH. Elute through a SILICYCLE® Si-Carbonate column (70 mL, 5 g) using MeOH. Collect the appropriate fractions and further purify via silica gel chromatography, eluting with a gradient of 0-100% of a mixture of 10% 7 N $NH_3$/MeOH in DCM, to give the title compound as a diastereomer (0.271 g, 88% yield). ES/MS m/z 375.0 $[M+H]^+$. $^1H$ NMR (400 MHz, $d_6$-DMSO) δ 1.49 (s, 3H), 3.33 (s, 2H), 3.64 (t, J=4.4 Hz, 1H), 4.32 (s, 1H), 4.68 (td, J=7.5, 5.2 Hz, 1H), 4.80 (d, J=3.7 Hz, 1H), 5.13 (d, J=7.1 Hz, 1H), 5.83 (d, J=8.1 Hz, 1H), 6.61 (d, J=3.5 Hz, 1H), 7.15-7.27 (m, 4H), 7.31-7.35 (m, 3H), 7.81 (td, J=8.0, 1.6 Hz, 1H), 8.09 (s, 1H).

EXAMPLE 18

Diastereomer of (2R,3R,4S,5S)-2-(4-aminopyrrolo[2,3-d]pyrimidin-7-yl)-5-[1-hydroxy-1-[2-(trifluoromethyl)phenyl]ethyl]tetrahydrofuran-3,4-diol

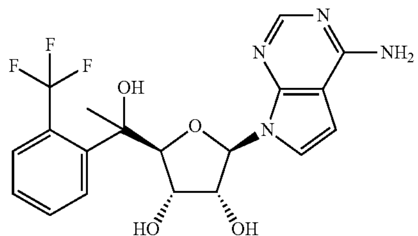 [SMILES: CC(O)(c1ccccc1C(F)(F)F)[C@H]1O[C@@H](n2ccc3c(N)ncnc32)[C@H](O)[C@@H]1O]

Mix TFA (3 mL) and water (1 mL) and cool to 0° C. Add this mixture to diastereomer of 1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-[2-(trifluoromethyl)phenyl]ethanol (0.137 g, 0.295 mmol) and stir at 0° C. After 20 min, concentrate the reaction mixture under reduced pressure and dissolve the resulting solid in MeOH. Elute the solution through a SILICYCLE® Si-Carbonate column (70 mL, 5 g) using MeOH. Collect the appropriate fractions and further purify via silica gel chromatography, eluting with a gradient of 0-100% of a mixture of 10% 7 N $NH_3$/MeOH in DCM, to give the title compound as a diastereomer (0.109 g, 87% yield). ES/MS m/z 425.0 $[M+H]^+$. $^1H$ NMR (400 MHz, $d_6$-DMSO) δ 1.52 (s, 3H), 3.76 (t, J=4.4 Hz, 1H), 4.38 (s, 1H), 4.64 (dd, J=7.6, 12.8 Hz, 1H), 4.80 (d, J=3.7 Hz, 1H), 5.14 (d, J=7.2 Hz, 1H), 5.86 (d, J=8.1 Hz, 1H), 6.61 (d, J=3.5 Hz, 1H), 6.93 (s, 1H), 7.17 (s, 2H), 7.38 (d, J=3.6 Hz, 1H), 7.48 (t, J=7.6 Hz, 1H), 7.65 (t, J=7.5 Hz, 1H), 7.81 (d, J=7.8 Hz, 1H), 7.87 (d, J=8.0 Hz, 1H), 8.06 (s, 1H).

EXAMPLE 19

Diastereomer of (2R,3R,4S,5S)-2-(4-aminopyrrolo[2,3-d]pyrimidin-7-yl)-5-[1-hydroxy-1-[4-(trifluoromethyl)phenyl]ethyl]tetrahydrofuran-3,4-diol

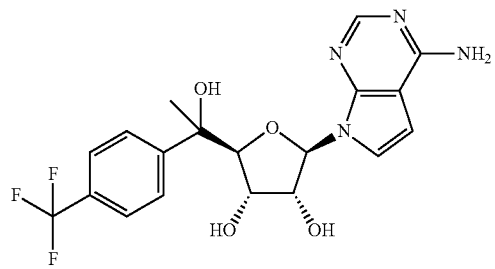 [SMILES: CC(O)(c1ccc(C(F)(F)F)cc1)[C@H]1O[C@@H](n2ccc3c(N)ncnc32)[C@H](O)[C@@H]1O]

Mix TFA (2 mL) and water (0.5 mL) and cool to 0° C. Add this to diastereomer of 1-[(3aR,4R,6S,6aR)-4-(4-aminopyrrolo[2,3-d]pyrimidin-7-yl)-2,2-dimethyl-3a,4,6,6a-tetrahydrofuro[3,4-d][1,3]dioxol-6-yl]-1-[4-(trifluoromethyl)phenyl]ethanol (0.136 g, 0.292 mmol) and stir at 0° C. After 45 min, concentrate under reduced pressure and dissolve the resulting solid in MeOH. Elute through a SILICYCLE® Si-Carbonate column (70 mL, 5 g) using MeOH. Collect the appropriate fractions and further purify via silica gel chromatography, eluting with a gradient of 10-25% of a mixture of 10% 7 N $NH_3$/MeOH in DCM, to give the title compound as a diastereomer (0.095 g, 76% yield). ES/MS m/z 425.0 $[M+H]^+$. $^1H$ NMR (400 MHz, $d_6$-DMSO) δ 1.44 (s, 3H), 3.66 (t, J=4.3 Hz, 1H), 4.20 (s, 1H), 4.67 (td, J=7.5, 5.2 Hz, 1H), 4.81 (d, J=3.7 Hz, 1H), 5.14 (d, J=7.2 Hz, 1H), 5.83 (d, J=8.1 Hz, 1H), 6.61 (d, J=3.6 Hz, 1H), 7.21 (s, 2H), 7.27 (s, 1H), 7.33 (d, J=3.6 Hz, 1H), 7.73 (d, J=8.4 Hz, 2H), 7.81 (d, J=8.2 Hz, 2H), 8.09 (s, 1H).

EXAMPLE 20

(2S,3S,4R,5R)-2-[(1R)-(1-(4-Chlorophenyl)-1-hydroxy-ethyl]-5-(4-methylpyrrolo[2,3-d]pyrimidin-7-yl)tetrahydrofuran-3,4-diol

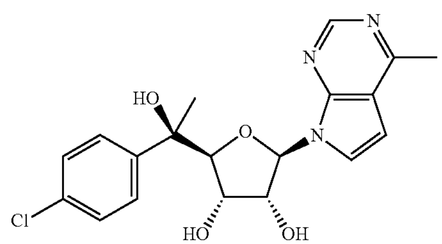 [SMILES: Cc1ncnc2c1ccn2[C@@H]1O[C@H]([C@](C)(O)c2ccc(Cl)cc2)[C@@H](O)[C@H]1O]

Stir a mixture of (1R)-1-[(3aR,4R,6S,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-1-(4-chlorophenyl)ethanol (0.265 g, 0.616 mmol), 4 N aqueous HCl in 1,4-dioxane (10 mL), and MeOH (10 mL) at room temperature. After 1 hr at room temperature, concentrate the solution under a stream of $N_2$ to remove the solvent. Add water (30 mL), neutralize to pH ~7 with saturated aqueous $NaHCO_3$, and extract with DCM (3×20 mL). Combine the organic extracts, dry over sodium sulfate, filter, and concentrate the filtrate under reduced pressure. Purify the resulting residue via silica gel chromatography, eluting with a gradient of 0-50% EtOAc in hexanes over 35 min, to give the title compound (0.180 g, 75% yield). ES/MS m/z ($^{35}Cl/^{37}Cl$) 390.02/392.2 $[M+H]^+$. $^1H$ NMR (400 MHz, $d_6$-DMSO) δ 1.39 (s, 3H), 2.46-2.48 (m, 5H), 3.30 (s, 1H), 2.65 (s, 3H), 3.68 (t, J=4.3 Hz, 1H), 4.08 (s, 1H), 4.51-4.54 (m, 1H), 4.84 (d, J=3.7 Hz, 1H), 5.15-5.17 (m, 1H), 6.07 (d, J=7.9 Hz, 1H), 6.18 (s, 1H), 6.76 (d, J=3.7 Hz, 1H), 7.37-7.39 (m, 2H), 7.53-7.56 (m, 2H), 7.79 (d, J=3.7 Hz, 1H), 8.64 (s, 1H).

EXAMPLE 21

Diastereomer of (2R,3S,4R,5R)-2-[(4-chloro-2-fluoro-phenyl)-hydroxy-methyl]-5-(4-methylpyrrolo[2,3-d]pyrimidin-7-yl)tetrahydrofuran-3,4-diol

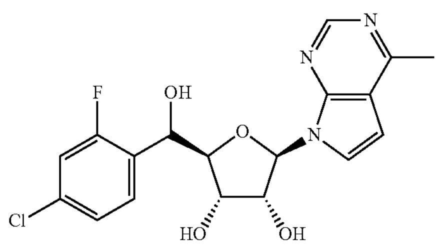 [SMILES: Cc1ncnc2c1ccn2[C@@H]1O[C@H](C(O)c2ccc(Cl)cc2F)[C@@H](O)[C@H]1O]

Stir a solution diastereomer of [(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-(4-chloro-2-fluoro-phenyl)methanol (0.220 g, 0.507 mmol), 4 N HCl in 1,4-dioxane (10.0 mL), and MeOH (10.0 mL) at room temperature. After 1 hr at room temperature, concentrate the solution under a stream of $N_2$ to remove the solvent. Partition the residue between DCM (25 mL), and water (25 mL). Neutralize to pH ~7 with saturated aqueous $NaHCO_3$, and extract with DCM (4×20 mL). Combine the organic extracts, dry over sodium sulfate, filter, and concentrate the filtrate under reduced pressure. Purify the resulting residue via silica gel chromatography, eluting with a gradient of 0-100% EtOAc in hexanes over 5 min, to give the title compound as a diastereomer (0.192 g, 96% yield). ES/MS m/z ($^{35}Cl/^{37}Cl$) 394.2/396.2 $[M+H]^+$. $^1H$ NMR (400 MHz, $d_6$-DMSO) δ 2.63 (s, 3H), 3.28-3.32 (m, 2H), 3.97-4.02 (m, 1H), 4.08-4.10 (m, 1H), 4.54-4.57 (m, 1H), 4.94-4.97 (m, 1H), 5.13-5.16 (m, 1H), 5.26-5.30 (m, 1H), 6.14 (d, J=7.7 Hz, 1H), 6.23 (d, J=4.5 Hz, 1H), 6.75 (d, J=3.7 Hz, 1H), 7.26 (dd, J=1.9, 8.3 Hz, 1H), 7.33 (dd, J=2.0, 10.2 Hz, 1H), 7.54 (t, J=8.2 Hz, 1H), 7.71 (d, J=3.9 Hz, 1H), 8.61 (s, 1H).

EXAMPLE 22

Diastereomer of ((2R,3S,4R,5R)-2-[(2-fluorophenyl)-hydroxy-methyl]-5-(4-methylpyrrolo[2,3-d]pyrimidin-7-yl)tetrahydrofuran-3,4-diol

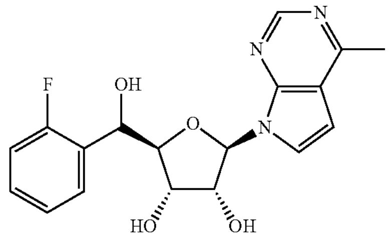 [SMILES: Cc1ncnc2c1ccn2[C@@H]1O[C@H](C(O)c2ccccc2F)[C@@H](O)[C@H]1O]

In a par vessel, evacuate a mixture of diastereomer of (2R,3S,4R,5R)-2-[(4-chloro-2-fluoro-phenyl)-hydroxy-methyl]-5-(4-methylpyrrolo[2,3-d]pyrimidin-7-yl)tetrahydrofuran-3,4-diol (0.090 g, 0.228 mmol), 10% Pd/C (0.025 g), triethylamine (0.069 g, 0.68 mmol), and EtOH (4.0 mL) under reduced pressure. Charge the vessel with hydrogen gas to 10 psi, and stir the resulting mixture at room temperature for 15 hr. Filter the resulting mixture through diatomaceous earth, and concentrate under reduced pressure. Purify the resulting residue via silica gel chromatography, eluting with a gradient of 0-100% EtOAc in hexanes over 5 min, to give the title compound as a diastereomer (0.082 g, 85% yield). ES/MS m/z 360.2 $[M+H]^+$. $^1H$ NMR (400 MHz, $d_6$-DMSO) δ 2.63 (s, 3H), 4.01-4.04 (m, 1H), 4.08-4.11 (m, 1H), 4.56-4.58 (m, 1H), 4.97-5.00 (m, 1H), 5.10 (d, J=4.2 Hz, 1H), 5.26 (d, J=7.1 Hz, 1H), 6.13-6.18 (m, 2H), 6.75 (d, J=3.7 Hz, 1H), 7.12-7.14 (m, 1H), 7.18-7.21 (m, 1H), 7.29-7.31 (m, 1H), 7.56-7.57 (m, 1H), 7.71-7.72 (m, 1H), 8.62 (s, 1H).

EXAMPLE 23

Diastereomer of (2S,3S,4R,5R)-2-[1-(3,4-dichlorophenyl)-1-hydroxy-ethyl]-5-(4-methylpyrrolo[2,3-d]pyrimidin-7-yl)tetrahydrofuran-3,4-diol

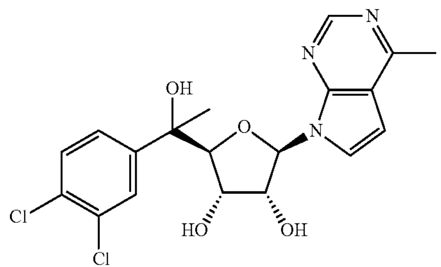 [SMILES: Cc1ncnc2c1ccn2[C@@H]1O[C@H](C(C)(O)c2ccc(Cl)c(Cl)c2)[C@@H](O)[C@H]1O]

Mix diastereomer of 1-[(3aR,4R,6S,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-1-(3,4-dichlorophenyl)ethanol (122.0 mg, 0.26 mmol), water (0.15 mL) and TFA (1.5 mL) at room temperature. After 1 hr, concentrate under reduced pressure and dissolve the resulting solid in MeOH. Elute through a SILICYCLE® Si-Carbonate column (70 mL, 5 g) using MeOH. Collect the appropriate fractions and concentrate to dryness under reduced pressure to give a residue. Purify the resulting residue via silica gel chromatography, eluting with a gradient of 10-50% of a mixture of 10% MeOH/MTBE in hexanes, to give the title compound as a diastereomer (62.8 mg, 56% yield). ES/MS m/z ($^{35}$Cl/$^{37}$Cl) 426/428 [M+H]$^+$. $^1$H NMR (400 MHz, $d_6$-DMSO) δ 1.45 (s, 3H), 2.69 (s, 3H), 3.73 (t, J=4.5 Hz, 1H), 4.14 (s, 1H), 4.52 (dd, J=7.4, 12.7 Hz, 1H), 4.92 (d, J=4.0 Hz, 1H), 5.19 (d, J=7.0 Hz, 1H), 6.12 (d, J=7.8 Hz, 1H), 6.32 (s, 1H), 6.80 (d, J=3.7 Hz, 1H), 7.55 (dd, J=2.0, 8.5 Hz, 1H), 7.63 (d, J=8.5 Hz, 1H), 7.80-7.81 (m, 2H), 8.68 (s, 1H).

EXAMPLE 24 AND EXAMPLE 25

(2R,3S,4R,5R)-2-[(R)-Hydroxy(phenyl)methyl]-5-pyrrolo[2,3-d]pyrimidin-7-yl-tetrahydrofuran-3,4-diol

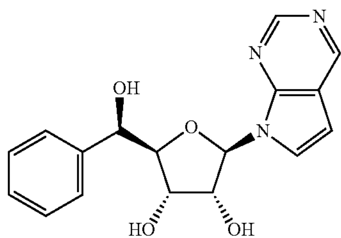 [SMILES: O[C@@H]1[C@H](O)[C@@H]([C@H](O)c2ccccc2)O[C@H]1n1ccc2cncnc21]

(2R,3S,4R,5R)-2-[(R)-(4-Chlorophenyl)-hydroxy-methyl]-5-pyrrolo[2,3-d]pyrimidin-7-yl-tetrahydro-furan-3,4-diol

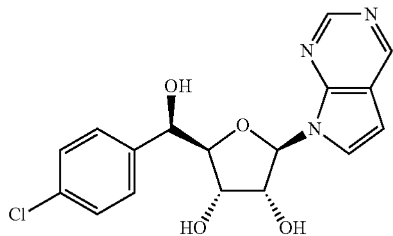 [SMILES: O[C@@H]1[C@H](O)[C@@H]([C@H](O)c2ccc(Cl)cc2)O[C@H]1n1ccc2cncnc21]

Dissolve (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol, (200.0 mg, 0.264 mmol) in EtOAc (30 mL). Hydrogenate the solution with a THALESNANO™ H-Cube flow system at room temperature (2000 kPa/1 mL per min/70 mm Pd/$Al_2O_3$ cartridge). Evaporate the resulting solution under reduced pressure, dissolve the resulting residue in EtOAc (20 mL), and repeat the hydrogenation with a new Pd/$Al_2O_3$ cartridge. Evaporate the resulting solution under reduced pressure. Dissolve the residue in 4 N HCl in 1,4-dioxane (5.73 mL, 22.9 mmol) and add water (3 drops). Stir the solution at room temperature for 45 min and evaporate under reduced pressure. Purify the resulting residue via reverse phase high pressure chromatography (PHENOMENEX® GEMINI®-NX) eluting with a gradient of 5-38% ACN in a mixture of 5% MeOH/10 mM ammonium bicarbonate, pH ~10, to give Example 23 and Example 24.

Example 24 (2R,3S,4R,5R)-2-[(R)-Hydroxy(phenyl)methyl]-5-pyrrolo[2,3-d]pyrimidin-7-yl-tetrahydrofuran-3,4-diol (15.0 mg, 9.11% yield). ES/MS m/z 328.1 [M+H)]. $^1$H NMR (400 MHz, $d_6$-DMSO) δ 3.18 (d, J=5.3 Hz, 3H), 4.05-4.15 (m, 3H), 4.62 (dd, J=5.2, 7.5 Hz, 1H), 4.80 (t, J=4.2 Hz, 1H), 5.10 (s, 1H), 5.22-5.30 (m, 1H), 6.22 (d, J=7.8 Hz, 1H), 6.74 (d, J=3.7 Hz, 1H), 7.24 (t, J=7.2 Hz, 1H), 7.32 (t, J=7.5 Hz, 2H), 7.41 (d, J=7.4 Hz, 2H), 7.87 (d, J=3.7 Hz, 1H), 8.81 (s, 1H), 9.04 (s, 1H).

Example 25 (2R,3S,4R,5R)-2-[(R)-(4-Chlorophenyl)-hydroxy-methyl]-5-pyrrolo[2,3-d]pyrimidin-7-yl-tetrahydro-furan-3,4-dio (51.9 mg, 28.8% yield). ES/MS m/z ($^{35}$Cl/$^{37}$Cl) 362.1/364.1 [M+H]$^+$. $^1$H NMR (400 MHz, $d_6$-DMSO) δ 3.18 (d, J=5.3 Hz, 3H), 4.01 (d, J=5.2 Hz, 1H), 4.08-4.14 (m, 2H), 4.61 (dd, J=7.2, 12.4 Hz, 1H), 4.81 (t, J=4.7 Hz, 1H), 5.14 (d, J=4.2 Hz, 1H), 5.31 (d, J=6.9 Hz, 1H), 8.81 (s, 1H), 6.06 (d, J=4.4 Hz, 1H), 6.21 (d, J=7.7 Hz, 1H), 6.74 (d, J=3.7 Hz, 1H), 7.35-7.43 (m, 4H), 7.88 (d, J=3.7 Hz, 1H), 9.04 (s, 1H).

EXAMPLE 26

(2R,3S,4R,5R)-2-[(R)-(4-Chlorophenyl)-hydroxy-methyl]-5-(4-methylpyrrolo[2,3-d]pyrimidin-7-yl) tetrahydrofuran-3,4-diol

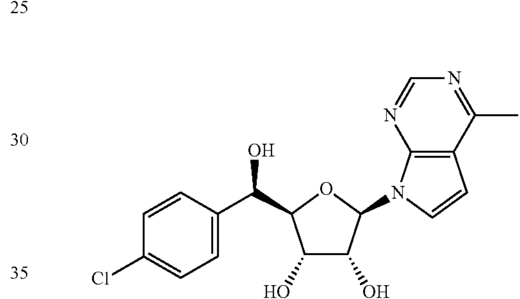

Stir a solution (R)-[(3aR,4R,6R,6aR)-2,2-dimethyl-4-(4-methylpyrrolo[2,3-d]pyrimidin-7-yl)-3a,4,6,6a-tetrahydro-furo[3,4-d][1,3]dioxol-6-yl]-(4-chlorophenyl)methanol (0.500 g, 1.08 mmol), 4 N HCl in 1,4-dioxane (50 mL), and MeOH (50 mL) at room temperature. After 1 hr at room temperature, concentrate the solution under a stream of $N_2$ to remove the solvent. To the residue add DCM (20 mL) and water (20 mL). Extract with DCM, and discard. Adjust the pH of the aqueous phase with saturated aqueous bicarbonate to pH ~10, and extract with DCM (4×20 mL). Combine the organic extracts, dry over sodium sulfate, filter, and concentrate the filtrate under reduced pressure. Dissolve the resulting residue in EtOAc, filter the solution through a pad of silica gel, and elute with EtOAc. Remove the filtrate under reduced pressure to give title compound (0.393 g, 97% yield). ES/MS m/z ($^{35}$Cl/$^{37}$Cl) 376.2/378.2 [M+H]$^+$. $^1$H NMR (400 MHz, $d_6$-DMSO) δ 2.63 (s, 3H), 3.95-3.97 (m, 1H), 4.05-4.08 (m, 1H), 4.53-4.59 (m, 1H), 4.75-4.79 (m, 1H), 5.09 (d, 1H, J=4.4 Hz), 5.25 (d, 1H, J=7.0 Hz), 6.07-6.13 (m, 2H), 6.75 (d, 1H, J=3.6 Hz), 7.31-7.34 (m, 2H), 7.36-7.40 (m, 2H), 7.76 (s, 1H, J=3.6 Hz), 8.62 (s, 1H).

The results of the following assays demonstrate evidence that the compounds exemplified herein are useful as PRMT5 inhibitors and may be useful in treating cancer.

PRMT5/MEP50 SPA Assay

The purpose of this assay is to measure the ability of a test compound to inhibit the enzyme activity of PRMT5 in vitro by inhibiting the catalytic activity of PRMT5/MEP50 complex, indicated by the transfer of radiolabeled methyl-$^3$H to a substrate peptide derived from the N-terminal sequence of the human histone H4.

Express the PRMT5/MEP50 enzyme complex using a baculovirus/Sf9 system and purify using anti-FLAG affinity chromatography, (essentially as described in preparations by Stephen Antonysamy, Zahid Bonday, Robert M. Campbell, Brandon Doyle, Zhanna Druzina, Tarun Gheyi, Bomie Han, Louis N. Jungheim, Yuewei Qian, Charles Rauch, Marijane Russell, J. Michael Sauder, Stephen R. Wasserman, Kenneth Weichert, Francis S. Willard, Aiping Zhang, and Spencer Emtage; Crystal structure of the human PRMT5:MEP50 complex, Proceedings of the National Academy of Sciences, 2012, Volume 109, pages 17960-17965.) Dilute purified enzyme to a working stock of 6.67 nM in assay buffer (50 mM TRIZMA® preset pH ~8.5, 1 mM DTT, 0.005% TWEEN® 80 0.01% HSA).

Add enzyme (15 μL/well) to a 384-well assay plate (CORNING® cat. #3706). Add test compounds from a 10 mM DMSO stock solution to the plate as serial dilutions in assay buffer to achieve a final test concentrations ranging from 50.0 μM to 25 nM. Create a reaction mix containing 1 μM Histone H4 biotinylated peptide substrate, H-SGRGK-GGKGLGKGGAKRHRKVLRDK-biotin (SEQ ID NO: 1), prepared by FastMoc chemistry with an ABI 431 peptide, and 4 μM $^3$H-SAM; 15 Ci/mmol, 0.366 mCi/mL, 37 μM, PERKIN-ELMER® cat. # NET155000MC) in assay buffer. To each plate well, add 5 μL of the peptide/$^3$H-SAM reaction mix to yield final assay conditions of 5 nM enzyme, 1 $^3$H-SAM, 250 nM peptide and 50 μM maximum test compound concentration with 0.5% DMSO, at a final volume of 20 μL. Incubate the assay for 2 hr at room temperature. Stop the reaction with the addition of guanidine HCl (5 M, 20 μL, Sigma cat. # G3272).

Suspend strepavidin YSI SPA scintillation beads (PERKIN-ELMER®, #RPNQ0012) at 1 mg/mL in pH ~8.5 Tris buffer containing 5 M guanidine HCl. To each well, add 20 μL of this bead suspension, agitate the resulting mixtures, and incubate for 1 hr at room temperature prior to measuring their radioactivity, using a microplate liquid scintillation counter as an indication of the formation of methylated peptide product.

Generate raw data from the radioactivity measurement as counts per min (CPM). Employ an uninhibited control (DMSO) and maximum inhibited control (250 μM dehydrosinefungin, (isolated essentially as described in Berry, D. R. & Abbott, B. J. Incorporation of carbon-14-labeled compounds into sinefungin (A9145), a nucleoside antifungal antibiotic. J. Antibiot. 1978 (31) 185-191 and references cited therein)). Calculate percent inhibition at each test compound concentration relative to controls as follows:

% inhibition=[Median CPM (uninhibited controls)−Median CPM (test compound)]/[Median CPM (uninhibited controls)−Median CPM (max inhibited controls)]*100

Plot the data using ActivityBase XE or Genedata software, as % Inhibition (y-axis) vs. Log test compound concentration (x-axis). Calculate the $IC_{50}$ values using a 4-parameter logistic curve fitting algorithm.

The results of this assay demonstrate that all of the exemplified compounds inhibit PRMT5/MEP50 catalytic activity with an $IC_{50}$ of less than 500 nM. Additionally, Examples 1-3 are tested essentially as described above and exhibit the following activity for PRMT5/MEP50 as shown in Table 1.

TABLE 1

| Example # | PRMT5/MEP50, $IC_{50}$ (nM) |
|---|---|
| 1 | 4.27 (±1.51, n = 7) |
| 2 | 9.51 (±5.73, n = 13) |
| 3 | 5.23 (±3.10, n = 3) |
| 4 | 5.2 (±1.51, n = 3) |

Mean ± SEM; SEM = standard error of the mean

Protocol Proliferation 7-day

The purpose of this assay is to measure the ability of test compounds to inhibit proliferation of cancer cells.

On day 1, plate A375 cells (ATCC, DMEM high glucose/10% Hi FBS) at 250 cells/well (100 μL/well) in a 96-well assay plate (BD Falcon 35-3219). Incubate the plates in a 37° C. incubator (5% $CO_2$) for 18-24 hr. On day 2, prepare and serially dilute test compounds in medium (1:2 10-point serial dilution) from compound stock solutions (10 mM in 100% DMSO). Add 10 μL of serial diluted test compounds to cell plates (0.2% DMSO final concentration). Add 10 μL of reference compound (Example 1) to column 1 of cell plates (20 μM final, 0.2% DMSO). Incubate cell plates at 37° C./5% $CO_2$ for 7 days. On day nine, thaw the CELL TITER-GLO® (Promega #G7571) buffer and equilibrate to room temperature prior to use. Also, equilibrate the lyophilized CELL TITER-GLO® substrate to room temperature prior to use. Transfer CELL TITER-GLO® buffer to an amber substrate bottle to reconstitute the lyophilized enzyme/substrate mixture to form the CELL TITER-GLO® reagent. Equilibrate the cell plate(s) to room temperature for 5-10 mM Gently remove media in cell plates by flicking and blotting on a stack of paper towels. Add CELL TITER-GLO® reagent (25 μL) to each well. Incubate plates for 10-20 mM at room temperature before reading. Measure luminescence using PERKIN-ELMER® ENVISION® Multi-label Plate Reader. Analyze this luminescence data by a 4-parameter curve fit using Activity Base, to yield cell proliferation $IC_{50}$ values.

The results of this assay demonstrate that Examples 1-3 have anti-proliferative effects on tumor cells, in accordance with their ability to inhibit PRMT5 activity. The resulting proliferation $IC_{50}$ values are shown in Table 2:

TABLE 2

| Example # | Proliferation $IC_{50}$ (nM) |
|---|---|
| 1 | 10.8 (±3.4, n = 3) |
| 2 | 31.5 (±7, n = 3) |
| 3 | 44.0 (n = 1) |

Mean ± SEM; SEM = standard error of the mean

MDM4 Exon5/6 qPCR Assay in A375 Tumor Cells

The purpose of this assay is to demonstrate the ability of test compounds to inhibit PRMT5 function in a cancer cell by measuring its ability to modulate the PRMT5-dependent alternative splicing of MDM4 in A375 melanoma cells, as measured by the ratio of MDM4 mRNA bearing exon 5 and 6 to that bearing solely exon 5.

Culture A375 tumor cells (ATCC), a melanoma cancer cell line, to 70%-90% confluence in T150 flasks with the growth medium (DMEM; HYCLONE™ #SH30022 with 10% FBS; GIBCO® 10082-147 or equivalent). Treat the cells with standard trypsin/EDTA treatment for 3 min and aspirate and wash with PBS to release the adherent cells from the culture flask. Seed the cells into a 96 well plate (Costar 3596) at 5000/well in growth medium (90 μL). Incubate the plate overnight at 37° C. and 5% $CO_2$ and treat the cells with test compound at serial dilutions (20, 6.67, 2.22, 0.74, 0.247, 0.082, 0.027, 0.009, 0.003, 0.010 μM, final DMSO addition of 0.2% yield) for 72 hr. Measure activity relative to maximum (2.0 μM of Example 2 and minimum (0.2% DMSO) controls.

On Day 5 after incubation, remove the medium from the culture plates and wash the cells twice with cold PBS (150 μL/well). Prepare Lysis Working Reagent from the TAQ-MAN® Gene Expression Cells-to-CT Kit (INVITROGEN™ cat. # AM1729) by dilution of DNAse 1 into Lysis Solution at 1/100. Add Lysis Working Reagent (50 μL/well) to the cell plates, mix well, and incubate at room temperature for 5 min Add kit stop solution (5 μL) to each well, mix the wells, and incubate for 2 min at room temperature. Prepare Reverse Transcriptase Master Mix in the following volume ratios; RT buffer: Nuclease-free water: RT Enzyme at 62.5: 31.25:6.25. Add RT mix (48 μL/well) to each well of a 96-well NUNC™ plate (THERMO SCIENTIFIC™ #260860). Add RT mix (20 μL) and each cell lysate sample (5 μL) into a 384 PCR plate (Clear Optical Reaction Plate, cat. #4309849, APPLIED BIOSYSTEMS®) quadrant 1 and add a second addition of RT Mix and cell lysate to quadrant 3. For the RT reaction, seal the plates and then place them in a thermal cycler set at 37° C. for 60 min; 95° C. for 5 min; stop at 4° C. For qPCR, prepare MDM4 exon 5 primers (Life Technologies Hs00967240-ml) and exon 6 primers (Life Technologies Hs00967242-ml) separately in the following volume ratios of RT mix: $H_2O$: exon probe at 10:6:1. Add Exon 5 (17 μL) to odd columns of a 384 PCR plate and add exon 6 (17 μL) to the even columns. Add cDNA (3 μL, from the RT plate) by quadrant stamping to each well of the qPCR plate containing the 17 μL exon primer solution. In this manner, perform qPCR for both exons on cDNAs from a single RT reaction on an individual cell lysate. Seal the plates, spin, and place on a real-time PCR instrument (Life Technologies ViiA7 Real-Time PCR). Run the TAQMAN® reaction in the following staged cycles: stage 1 (50° C., 2 min), stage 2 (95° C., 10 min), stage 3 (95° C., 15 seconds), stage 4 (60° C., 60 seconds) with stages 3 and 4 repeated for 40 cycles.

Retrieve CT data from the real-time PCR reader and perform the following calculations, where "CPD" is the value from compound-treated samples, and "DMSO" is the minimum control sample, using an Excel template:

(Exon 6 CT CPD−Exon 6 CT DMSO)−(Exon 5 CT CPD−Exon 5 CT DMSO)=ΔCT $2^{(-\Delta CT)}$=Fold Change Using Genedata software, plot the data as Fold Change (y axis) versus Log test compound concentration (x-axis) and calculate the $EC_{50}$ values using a 4-parameter logistic fit.

This assay demonstrates that all of the exemplified compounds tested in this assay inhibit PRMT5 mediated regulation of the splicing of MDM4, as indicated by the ratio of produced mRNA bearing exon 6 versus mRNA bearing exons 5 and 6.

For example, the resulting $EC_{50}$ values for the ability of Examples 1, 2, and 3 to modulate the splicing of MDM4 are shown in Table 3.

TABLE 3

| Example # | MDM4 Exon5/6 $EC_{50}$ (nM) |
|---|---|
| 1 | 16.79 (±1.63, n = 10) |
| 2 | 36.72 (±3.24, n = 16) |
| 3 | 42.38 (±9.08, n = 2) |
| 4 | 1038 (±45, n = 2) |

Mean ± SEM; SEM = standard error of the mean

Combination with BCL2 Inhibitor ABT-199 in AML Cell Lines (4-day and 7-day Cell Proliferation Assay)

The purpose of this assay is to demonstrate the synergistic inhibitory effect on the proliferation of AML cell lines when PRMT5 inhibitor is combined with BCL2 inhibitor, ABT-199 (Abbot Laboratories).

On day 1, plate GDM-1 [ATCC®, maintained throughout in GDM-1 assay medium: RPMI-1640 medium/20% heat-inactivated FBS (GIBCO®)] and EOL-1 cells [ATCC®, maintained throughout in EOL-1 assay medium: RPMI-1640 medium/10% heat-inactivated FBS (GIBCO®)] at 4000 and 10000 cells/well (100 μL/well) respectively, in a 96-well assay plate (BD FALCON® 35-3219). Incubate the plates in a 37° C. incubator (5% $CO_2$) for 18-24 hr. On day 2, prepare 2.0% DMSO with assay medium (as indicated above or RPMI-1640/20% heat-inactivated FBS and RPMI-1640/10% FBS for GDM-1 and EOL-1, respectively) and add 100 μL to columns 3-12 in a preparation plate. Prepare test compounds ABT-199 at 10 μM in 2% DMSO and PRMT5 inhibitor Example 1 at 25 μM in 2% DMSO and dispense into wells A2 and B2, respectively, followed by serial dilution (1:3, 10 points) to wells A11 and B11, respectively. For combinational treatment, serially dilute test compound examples at 1:2 in assay medium (as indicated above or RPMI-1640/20% heat-inactivated FBS and RPMI-1640/10% FBS for GDM-1 and EOL-1, respectively) in wells C2-C11 (0.1 μM) to H2-H11, then serially dilute test compound ABT-199 1:3 from C2-H2 (1.0 μM) to C11-H11. Prepare 20 μM Staurosporine (available at Sigma) in 2% DMSO as a reference compound in wells A1 to HE Add 11 μL of serial diluted compounds to 100 μl cell-containing wells in the cell plates. The final start concentrations in the cell plates are as follows: for single compound, 2.5 μM for PRMT5 inhibitor Example 1 and 1 μM for ABT-199; for the combination of the two compounds, starting concentrations are 0.01 μM for PRMT5 inhibitor Example 1 and 0.1 μM for ABT-199; final DMSO concentration is 0.2%. Incubate cell plates at 37° C./5% $CO_2$ for four or seven days. On day six or nine (for testing four-day or seven-day treatment, respectively), thaw the CELL TITER-GLO® (Promega #G7571) buffer and equilibrate to room temperature prior to use. Also, equilibrate the lyophilized CELL TITER-GLO® substrate to room temperature prior to use. Transfer CELL TITER-GLO® buffer to an amber substrate bottle to reconstitute the lyophilized enzyme/substrate mixture to form the CELL TITER-GLO® reagent. Equilibrate the cell plates to room temperature for 5-10 min. Add CELL TITER-GLO® reagent (100 μL) to each well. Incubate plates for 10-15 min at room temperature before reading. Measure luminescence using the PERKIN-ELMER® ENVISION® Multi-Label Reader. Analyze data with Medium Throughput Dorsal, to yield cell proliferation $IC_{50}$ values and inhibition combination indices based on Chou-Talalay analysis. [Chou T C, Talalay P. Analysis of combined drug effects: a new look at a very old problem. Trends Pharmacol Sci 1983; 4:450-4.]

The results of this assay demonstrate that a combination of BCL2 inhibitor ABT-199 and PRMT5 inhibitor Example 1 has a synergistic inhibitory effect on cancer cell proliferation. The resulting proliferation absolute $IC_{50}$ values and combination index values are shown in Table 4:

TABLE 4

| Cell Line | Absolute $IC_{50}$ PRMT5 Ex 1 | Abs $IC_{50}$ ABT-199 | Abs $IC_{50}$ Combination | Combination Index | Treatment Duration |
|---|---|---|---|---|---|
| GDM-1 | 0.224 μM (+/−0.0191) | 0.007 μM (+/−0.001) | 0.00014 μM (+/−0.00009) | <0.5, Synergistic | 4 Days |
| EOL-1 | 0.006 μM (+/−0.001) | 0.030 μM (+/−0.001) | 0.000003 μM (+/−0.000001) | <0.5, Synergistic | 7 Days |

Mean ± standard error of the mean

Mouse A375 Xenograft Tumor MDM4 Exon5/6 RNA Splicing Assay

The purpose of this assay is to measure the ability of a test compound to inhibit PRMT5-mediated retention of exon 6 in the processed MDM4 mRNA in A375 tumor cells in a mouse tumor xenograft model. This assay represents the effect of a test compound on specific PRMT5-mediated splicing events in tumors in an animal model.

Grow A375 cells in medium (DMEM high glucose/10% Hi FBS) at 37° C. in an incubator (5% $CO_2$) for 18-24 hr. Mix the cells with MATRIGEL® (1:1) and implant the cells ($5\times10^6$/animal) subcutaneously into the rear flank of the mice (female nude mice, Harlan). The implanted tumor cells grow as solid tumors. Measure the tumor volume and body weight twice a week with a caliper. After tumor volume reaches approximately 200-250 $mm^3$ (about 20 days after implant), randomize the animals, and group them into compound treatment groups. Administer the test compounds (formulated in SWFI with 1% HEC/0.25% TWEEN® 80/0.05% Antifoam) by oral gavage. Test compound doses are in the range of 3 to 100 mg/kg. Sacrifice mice 4 hr after the last dose (4 days of dosing).

Harvest tumor tissues and homogenize as described below. Place tumor samples in a bowl and add 1 mL of liquid $N_2$. Squash the tumor in the bowl. Transfer small pieces of tumor (about 20 mg each) into 2 lysing matrix D tubes (MPBIO cat. #6913-250). Use one tube for RNA processing and the other for protein lysate preparation. For RNA processing, homogenize the tumor tissues in an RNEASY® Mini Kit (QIAGEN-74104) extraction buffer (0.5 mL each) for 30 seconds using a Bio101 FastPrep FP120 homogenizer (setting 6). Total RNA is purified with QUARTZY® RNEASY® Mini Kit −50 (QIAGEN-74104, RNEASY® Mini Handbook, Fourth Edition, June 2012). Check the RNA concentration to ensure OD 260/280 nM≥1.9. For cDNA synthesis use A&B APPLIED BIOSYSTEMS®, High Capacity cDNA Reverse Transcription Kit (cat. #4368813). Use 1 μg total RNA (10 μL) in each RT reaction volume of 20 μL, containing 10×RT Buffer—2.0 μL; 25×dNTP Mix (100 mM)—0.8 μL; 10×RT Random Primers—2.0 μL; MULTISCRIBE™ Reverse Transcriptase—1.0 μL; Nuclease-free $H_2O$—4.2 pt. Optimize these conditions (thermal cycler from APPLIED BIOSYSTEMS®) for use with the High Capacity cDNA Reverse Transcription Kits: Step 1—Temperature 25° C./Time 10 mM; Step 2—Temperature 37° C./Time 120 mM; Step 3—Temperature 85° C./Time 5 mM; Step 4 Temperature 4° C. until further use.

Next, run the thermal cycler program for the TAQMAN® qPCR reaction in a 20 μL total volume containing 10 μL of 2×PCR mix, 1 μL of probes, 3 μL of prepared cDNA (20 ng) and water (6 μL). [AB solute blue QPCR ROX Mix (2×) from THERMO SCIENTIFIC™ cat. #: AB-4139; MDM4 (exon 5 and exon 6) Probes from APPLIED BIOSYSTEMS®, cat. #: Hs00967240-ml and cat. #: Hs00967242-ml respectively; GAPDH Probe from APPLIED BIOSYSTEMS®, cat. #: Hs02758991-g1; CDKN1A (P21) Probe from APPLIED BIOSYSTEMS®, cat. #: Hs02758991-g1]. The samples are run on the ViiA7 TAQMAN® thermal cycle machine (APPLIED BIOSYSTEMS®).

Mouse A375 Tumor Xenograft MDM4 and SmD1-me2S Western Blot Assay

For western blotting, homogenize the tumor tissues as performed above in 500 μL of kit XY lysis buffer including protease inhibitor cocktail complete Mini (Roche, cat. #: 11 836 170 001) [this cocktail contains 10 mg/mL Leupeptin Hemisulfate (Sigma cat. # L2884); 10 mg/mL Trypsin-Chymotrypsin Inhibitor (Sigma cat. # T9777); 10 μg/mL TPCK (Sigma cat. # T4376); 10 μg/mL Aprotinin (Sigma cat. # A1153); 60 mM Beta-Glycerophosphate disodium salt hydrate (Sigma cat. # G9891); 1% TRITON™ X-100 (Sigma cat. # T9284); 25 mM Tris pH ~7.5 (INVITROGEN™ cat. #15567-027); 2.5 mM sodium pyrophosphate dibasic (Fluka cat. #71501); 300 mM $NaCl_2$ (Mallinckrodt cat. #7581); 2 mM TAME (Sigma cat. # T4626); 15 mM pNPP (pNPP disodium salt hexahydrate, Sigma cat. #P4744); 5 mM benzamidine hydrochloride hydrate (Sigma cat. #B6506); 10 mM sodium fluoride (Sigma cat. #S-7920); 1 mM sodium metavanadate anhydrous (Sigma cat. #59088); 5 g. 1 mM DTT (Sigma cat. # D9779); 15 mM EDTA pH ~8.0 (INVITROGEN™ cat. #15575020); 5 mM EGTA pH ~8.0 (Sigma cat. #E3889); 1 mM Microcystin-LR (Fisher/Axxora cat. # A350012m001); 0.25 mM Pefa Bloc (Sigma cat. #76307). Spin the protein lysates down at 8,000 rpm for 10 min and transfer supernatants to 1.5 mL tubes for sonication (amplitude 25% yield) for 15 seconds. Spin the lysates down again at 15,000 rpm for 10 min From the supernatant, take 60 μg of each protein lysate, mix with SDS-PAGE sample loading buffer [15 μL of protein lysate; 5 μL of 4× sample buffer (Bio-Rad cat. #161-0791); 2.25 μL10× sample reducing agent (INVITROGEN™ cat. # NP0004); boil samples at 100° C. for 10 min] and run in SDS-PAGE using 4-20% Tris-Glycine gel-1.5 mm×15 well (INVITROGEN™). Once the dye front reaches the bottom of the gel, stop the electrophoresis and transfer the proteins from the gel to nitrocellulose membrane for western blotting with the following primary antibodies: anti-MDM4 clone 8c6, mouse monoclonal from Millipore, cat. #04-1555, anti-SmD1-me2S [mouse monoclonal, 2.14 mg/mL] and with rabbit anti-GAPDH antibody (CAT: AB9485 Abcam). Anti-SmD1-me2S monoclonal antibodies are generated at Eli Lilly in NZB/W mice (The Jackson Laboratory). Five 6 weeks old female mice are immunized subcutaneously with 75 μg of a mixture of two peptides conjugated to KLH in complete Freund's adjuvant (see below).

```
                                          (SEQ ID NO: 2)
CREAVAGR*GR*GR*GR*GR*GGPRR

                                          (SEQ ID NO: 3)
REAVAGR*GR*GR*GR*GR*GGPRRC
```

The asterisk indicates symmetric dimethyl-Arg. KLH is conjugated with the Cys amino acid (C). After priming, mice are injected subcutaneously every 3 weeks with 50 μg of the mixture of the two peptides conjugated to KLH in incomplete Freund's adjuvant. Ten days after the third boost, blood is collected using a retro-orbital procedure to measure antibody titers in serum. Spleen cells from positive mice are isolated and fused with the myeloma cell line P3X63Ag8.653 (ATCC® CRL-1580) at a ratio (1:4) using PEG as described by Harlow (Antibodies: a laboratory manual. Cold Spring Harbor, N.Y., 2004). Fused cells are seeded in 96 well plates and after 1 week in selection media containing HAT and supernatants are tested for binding to SmD1-me2S peptides by ELISA. Specificity is tested by ELISA with unmethylated peptides and a SmD3-symmetric dimethyl-Arg peptide. ELISA positive hybridoma cells are subcloned by serial dilutions and the antibodies are purified by affinity chromatography with the above peptide antigens.

Once transfer is complete, block the membrane with blocking buffer (Odyssey blocking buffer, LI-COR Biosciences cat. #927-40000 with 0.05% TWEEN®-20, Biorad cat. #161-0781) and then treat the membrane overnight at 4° C. with anti-MDM4 clone 8c6, mouse monoclonal from Millipore, cat. #04-1555 diluted 1:500, anti-SmD1-me2S (mouse monoclonal in-house 2.14 mg/ml), dilute 1:300 and with rabbit anti-GAPDH antibody (CAT: AB9485 Abcam) dilute 1:1000 in blocking buffer. Wash the membranes 3 times with TBS TWEEN® (0.05% yield), each time for 10-15 min [10×TBS (Sigma cat. #170-6435)]. Next incubate the membranes for 1.5 hr at room temperature with the following secondary antibodies at the following dilutions in blocking buffer: IRDye 680LT, Goat anti-rabbit, LICOR® cat. #926-68021, Lot# C10314-03, dilute 1:6000 and IRDye 800CW, goat anti-mouse IgG (H+L), LICOR® cat. #926-32210, lot# C10131-01, dilute 1:6000. Wash the membranes 3× (10 min each) with TBS TWEEN®. Develop the membranes for scanning with a LICOR® ODYSSEY® imaging system to measure detected Western blot band intensity. Calculate the percent inhibition of test compound treated groups relative to the vehicle treated group samples as minimum inhibition groups using the following equation:

% inhibition=[Median band intensity (uninhibited controls)−median band intensity (test compound)]/[Median band intensity(uninhibited controls)−Median band intensity (maximum inhibited controls)]*100 where the maximum inhibited control sample is chosen to be from the A375 tumors taken ex vivo from tumor bearing mice following 4 days of oral administration of Example 1, 10 mg/kg BID.

Calculate $ED_{50}$ from a dose response study as the dose necessary to achieve 50% effect at this time point.

For the described assays, (Mouse A375 xenograft tumor MDM4 exon5/6 RNA splicing assay and Mouse A375 tumor xenograft MDM4 and SmD1-me2S Western blot assay) the compounds of Examples 1, 2 and 3 achieve 50% effect following doses ≤30 mg/kg PO given QD or BID. These results demonstrate that the exemplified compounds of Examples 1, 2, and 3 inhibit PRMT5 activity in vivo as indicated by their effects on PRMT5 substrates and associated consequent molecular cell biology endpoints.

Xenograft Tumor Models

The purpose of this assay is to measure in a mouse model of cancer the reduction in tumor volume in response to test compound administration.

Grow A375 (melanoma) cells in DMEM/High glucose (HYCLONE™ cat. # SH30022) with 10% HI FBS (GIBCO® cat. #10082-147). Grow Will-2 (DLBCL) cells in RPMI 1640 with L-glutamine and 20% heat inactivated FBS. Grow Namalwa (Burkitt's lymphoma) cells (ATCC) in RPMI 1640 media supplemented with L-glutamine, 25 mM HEPES (GIBCO® 22400-089), 1 mM sodium pyruvate and 7.5% FBS. Grow Molt 4 cells in RPMI 1640 with L-glutamine, 25 mM HEPES [GIBCO 22400-089], 1 mM sodium pyruvate, and 10% FBS. Harvest cells and inject subcutaneously onto the rear flank of nude mice (A375: $5\times10^6$ cells/animal, mixed 1:1 with MATRIGEL®; Will-2; $1\times10^7$ cells/animal; Namalwa: $2\times10^6$ cells/animal; Molt 4: : $5\times10^6$ cells/animal, mixed 1:1 with MATRIGEL®). When tumors are established (approximately 200 $mm^3$, 7-21 days after implant), randomize animals, and group them into control and test groups. Formulate the test compound in 1% HEC/0.25% TWEEN®-80/0.05% Antifoam. Administer test compound and vehicles by oral gavage. Determine tumor response by tumor volume measurement (caliper) performed twice a week during the course of treatment and report as the percent inhibition of tumor volume versus the vehicle control group.

Example 1 demonstrates dose dependent anti-tumor activity in all three xenograft tumor models. For example, in the melanoma model (A375), when dosed at 10 mg/kg QD on a 4-day-on and 3-day-off schedule for 26 days), 64% inhibition is achieved; when dosed at 15 mg/kg on the same schedule, 71% inhibition is achieved. In the DLBCL tumor model (WILL-2), when dosed at 2 mg/kg (BID for 14 days), 50% regression is achieved; when dosed at 5 mg/kg (QD for 14 days) 74% inhibition is achieved. In the lymphoma tumor model (Namalwa), when dosed at 2 mg/kg (BID for 14 days) 74% inhibition is achieved; when dosed at 5 mg/kg (QD for 14 days), 61% inhibition is achieved. This data demonstrates that Example 1 inhibits tumor xenograft growth in the above 3 tumor models.

Example 4 in an acute lymphoblastic leukemia model (Molt 4), when dosed 60 mg/kg (BID for 30 days), −75% inhibition is achieved. This data demonstrates that Example 4 inhibits tumor xenograft growth in the above tumor model.

The compounds of the present invention are preferably formulated as pharmaceutical compositions administered by a variety of routes. Most preferably, such compositions are for oral or intravenous administration. Such pharmaceutical compositions and processes for preparing same are well known in the art. See, e.g., REMINGTON: THE SCIENCE AND PRACTICE OF PHARMACY (D. Troy, et al., eds., 21st ed., Lippincott Williams & Wilkins, 2005).

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the daily range of about 0.05-1000 mg. Preferably such doses fall within the daily range of 0.1-500 mg. More preferably such doses fall within the daily range of 0.5-100 mg. In some instances dosage levels below the lower limit of the aforesaid ranges may be more than adequate, while in other cases still larger doses may be employed without causing any harmful side effect, and therefore the above dosage ranges are not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of the formula:

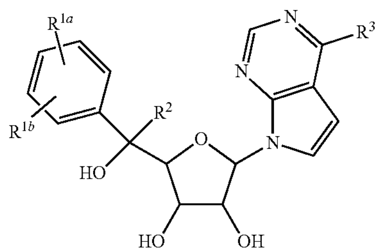

wherein:

$R^{1a}$ is cyclopropoxy;

$R^{1b}$ is chloro;

$R^2$ is hydrogen; and $R^3$ is amino; or a pharmaceutically acceptable salt thereof.

2. The compound or salt thereof according to claim 1 wherein the configuration of the chiral carbon to which the $R^2$ substituent is attached is R, S or a mixture thereof.

3. The compound according to claim 1 which is

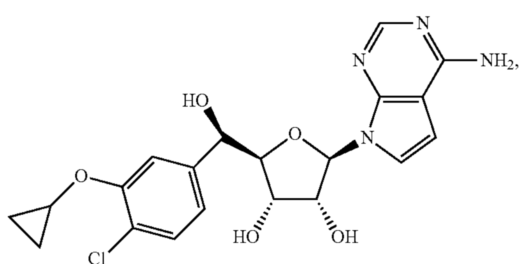 [SMILES: Nc1ncnc2c1ccn2[C@@H]1O[C@H]([C@H](O)c2ccc(Cl)c(OC3CC3)c2)[C@@H](O)[C@H]1O]

or a pharmaceutically acceptable salt thereof.

4. A pharmaceutical composition comprising a compound of the formula:

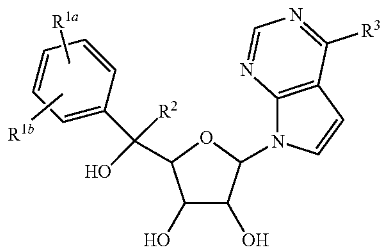

wherein:

$R^{1a}$ is cyclopropoxy;

$R^{1b}$ is chloro;

$R^2$ is hydrogen; and $R^3$ is amino; or a pharmaceutically acceptable salt thereof, with a pharmaceutically acceptable excipient, carrier, or diluent.

5. A method of treating cancer wherein the cancer is selected from the group consisting of glioblastomas, melanoma, sarcomas, gastric cancer, pancreatic cancer, cholangiocarcinoma, bladder cancer, breast cancer, non-small cell lung cancer, leukemias including acute myeloid leukemia, and lymphomas, in a patient in need of such treatment comprising administering the patient an effective amount of a compound of the formula:

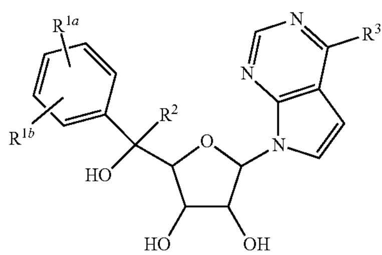
wherein:
$R^{1a}$ is cyclopropoxy;
$R^{1b}$ is chloro;
$R^2$ is hydrogen; and
$R^3$ is amino; or a pharmaceutically acceptable salt thereof.
6. The pharmaceutical composition according to claim 4 wherein the compound is
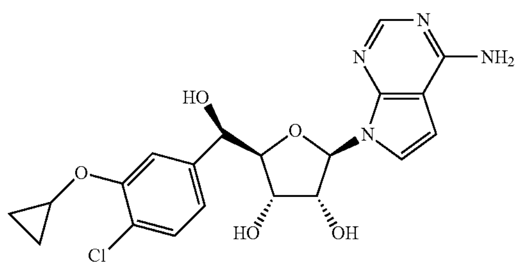 [SMILES: Nc1ncnc2c1ccn2[C@@H]1O[C@H]([C@H](O)c2ccc(Cl)c(OC3CC3)c2)[C@@H](O)[C@H]1O]
or a pharmaceutically acceptable salt thereof.
7. The method according to claim 5 wherein the compound is:
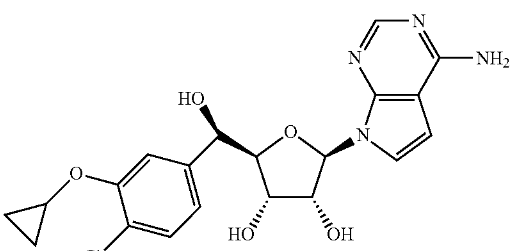
or a pharmaceutically acceptable salt thereof.
* * * * *